US011263568B2

(12) United States Patent
Kanukurthy et al.

(10) Patent No.: US 11,263,568 B2
(45) Date of Patent: Mar. 1, 2022

(54) INTELLIGENT SAFETY MONITORING AND ANALYTICS SYSTEM FOR PERSONAL PROTECTIVE EQUIPMENT

(71) Applicant: 3M INNOVATIVE PROPERTIES COMPANY, St. Paul, MN (US)

(72) Inventors: Kiran S. Kanukurthy, Cottage Grove, MN (US); Steven R. Digre, St. Paul, MN (US); Darcey L. Holloway, Stillwater, MN (US); Eric C. Lobner, Woodbury, MN (US); Ted K. Madison, St. Paul, MN (US); Philip J. Savoie, Chanhassen, MN (US); Pageen S. Smith, Cadillac, MI (US); Lauraine L. Wells, Loveland, CO (US); Michael G. Wurm, Waukesha, WI (US); Cameron J. Fackler, Indianapolis, IN (US); James D. Brown, Bloomington, IN (US); Matthew J. Blackford, Hastings, MN (US); Steven T. Awiszus, Woodbury, MN (US); Elliott H. Berger, Indianapolis, IN (US)

(73) Assignee: 3M Innovative Properties Company, St. Paul, MN (US)

( * ) Notice: Subject to any disclaimer, the term of this patent is extended or adjusted under 35 U.S.C. 154(b) by 118 days.

(21) Appl. No.: 16/077,541

(22) PCT Filed: Mar. 7, 2017

(86) PCT No.: PCT/US2017/021118
§ 371 (c)(1),
(2) Date: Aug. 13, 2018

(87) PCT Pub. No.: WO2017/155968
PCT Pub. Date: Sep. 14, 2017

(65) Prior Publication Data
US 2019/0073618 A1    Mar. 7, 2019

Related U.S. Application Data

(60) Provisional application No. 62/304,644, filed on Mar. 7, 2016.

(51) Int. Cl.
*G06Q 30/00* (2012.01)
*G06Q 10/06* (2012.01)
(Continued)

(52) U.S. Cl.
CPC ....... *G06Q 10/06315* (2013.01); *G06F 9/542* (2013.01); *G06F 17/18* (2013.01);
(Continued)

(58) Field of Classification Search
CPC .. G06Q 10/06315; G06Q 30/00; G06Q 10/06; G06Q 10/0635; G06Q 50/22;
(Continued)

(56) References Cited

U.S. PATENT DOCUMENTS 917,738 A    4/1909 Opsal
2,497,632 A    2/1950 Shacht
(Continued)

FOREIGN PATENT DOCUMENTS

CN    106037755    10/2016
DE    03611625    10/1987
(Continued)

OTHER PUBLICATIONS

Le et al., App-based system diagnosis using mobile information systems, https://ieeexplore.ieee.org/stamp/stamp.jsp?tp=& arnumber= 7005150, Proceedings of the 2014 IEEE Emerging Technology and Factory Automation (ETFA) (Year: 2014).*
(Continued)

*Primary Examiner* — Patricia H Munson
*Assistant Examiner* — Uche Byrd
(74) *Attorney, Agent, or Firm* — Steven A. Bern; Christopher D. Karlen

(57) ABSTRACT

In some examples, a system includes an article of hearing protection assigned to a worker, and a portable computing device assigned to the worker; a remote computing device
(Continued)

communicatively coupled to the portable computing device, the remote computing device configured to receive sound level data that indicate different sound levels at different, respective locations of a work environment; determine, based on location data received from the portable computing device, an amount of sound received by the worker over a period of time; identify an updated location in the work environment having a sound level that is different from a current location, based at least in part on the article of hearing protection, the amount of sound, and the sound level data that indicates different sound levels at different, respective locations; and generate a notification that instructs the worker to move from the current location to the updated location.

14 Claims, 41 Drawing Sheets

(51) Int. Cl.
    *G16H 40/67*    (2018.01)
    *G06F 9/54*    (2006.01)
    *G06F 17/18*    (2006.01)
    *G08B 21/02*    (2006.01)

(52) U.S. Cl.
    CPC ......... *G06Q 10/06* (2013.01); *G06Q 10/0635* (2013.01); *G08B 21/02* (2013.01); *G16H 40/67* (2018.01)

(58) Field of Classification Search
    CPC .. G06Q 10/105; G06Q 30/0255; G06F 17/18; G06F 9/542; G08B 21/02
    See application file for complete search history.

(56) References Cited

U.S. PATENT DOCUMENTS

| | | |
|---|---|---|
| 3,473,199 A | 10/1969 | Rohland |
| 3,474,559 A | 10/1969 | Hunt |
| 3,636,594 A | 1/1972 | Faivre |
| 3,751,835 A | 8/1973 | Smith |
| 4,139,956 A | 2/1979 | Sharrow |
| 4,242,777 A | 1/1981 | Bourard |
| 4,512,096 A | 4/1985 | Heidecker |
| 4,553,633 A | 11/1985 | Armstrong |
| 4,612,719 A | 9/1986 | de Jong |
| 5,584,133 A | 12/1996 | Motooka |
| 5,758,443 A | 6/1998 | Pedrazzini |
| 5,832,761 A | 11/1998 | Chen |
| 5,914,913 A | 6/1999 | Shriqui |
| 5,973,559 A | 10/1999 | Alberty |
| 6,105,715 A * | 8/2000 | Knauer ................ A61F 11/08 181/135 |
| 6,144,301 A | 11/2000 | Frieden |
| 6,239,737 B1 | 5/2001 | Black |
| 6,276,179 B1 | 8/2001 | Janssen |
| 6,314,183 B1 | 11/2001 | Pehrsson |
| 6,346,886 B1 | 2/2002 | De La Huerga |
| 6,568,354 B1 | 5/2003 | Wasserman |
| 6,666,170 B1 | 12/2003 | Hilpert |
| 6,693,543 B1 | 2/2004 | Stephenson |
| 6,747,562 B2 | 6/2004 | Giraldin |
| 6,810,406 B2 | 10/2004 | Schlabach |
| 6,823,617 B2 | 11/2004 | Schweikert |
| 6,853,303 B2 | 2/2005 | Chen |
| 6,897,374 B2 | 5/2005 | Garber |
| 6,965,866 B2 | 11/2005 | Klein |
| 7,002,526 B1 | 2/2006 | Adams |
| 7,152,035 B1 | 12/2006 | Suhy, Jr. |
| 7,191,097 B1 | 3/2007 | Lee |
| 7,194,415 B2 | 3/2007 | Hamada |
| 7,263,379 B1 | 8/2007 | Parkulo |
| 7,319,399 B2 | 1/2008 | Berg |
| 7,363,193 B2 | 4/2008 | Jacobs |
| 7,398,097 B2 | 7/2008 | Parkulo |
| 7,464,001 B1 | 12/2008 | Adams |
| 7,487,098 B2 | 2/2009 | Takagi |
| 7,621,846 B2 | 11/2009 | Ainsworth |
| 7,633,387 B2 | 12/2009 | Carmichael |
| 7,652,571 B2 | 1/2010 | Parkulo |
| 7,654,453 B2 | 2/2010 | Mochizuki |
| 7,764,173 B2 | 7/2010 | Yamagiwa |
| 7,768,409 B2 | 8/2010 | Parias |
| 7,817,803 B2 | 10/2010 | Goldstein |
| 7,978,861 B2 | 7/2011 | Michael |
| 7,983,426 B2 | 7/2011 | Schuler |
| 8,150,043 B2 | 4/2012 | Goldstein |
| 8,170,228 B2 | 5/2012 | Goldstein |
| 8,170,884 B2 | 5/2012 | Vaudrey et al. |
| 8,199,919 B2 | 6/2012 | Goldstein |
| 8,249,266 B2 | 8/2012 | Michael |
| 8,294,580 B2 | 10/2012 | Witwer |
| 8,848,929 B2 | 9/2014 | Schiller |
| 9,319,812 B2 | 4/2016 | Banerjee |
| 9,411,994 B2 | 8/2016 | Alan |
| 9,554,733 B2 | 1/2017 | Henriksen |
| 2001/0056359 A1 | 12/2001 | Abreu |
| 2002/0022969 A1 | 2/2002 | Berg |
| 2002/0026537 A1 | 2/2002 | Schlabach |
| 2002/0188593 A1 | 12/2002 | Moser |
| 2003/0158796 A1 | 8/2003 | Balent |
| 2003/0226010 A1 | 12/2003 | Arima |
| 2004/0004547 A1 | 1/2004 | Appelt |
| 2004/0190729 A1 | 9/2004 | Yonovitz |
| 2004/0229730 A1 | 11/2004 | Ainsworth |
| 2005/0114154 A1 | 5/2005 | Wolkowicz |
| 2005/0155887 A1 | 7/2005 | Bazany |
| 2005/0261938 A1 | 11/2005 | Silverbrook |
| 2006/0026017 A1 | 2/2006 | Walker |
| 2006/0048998 A1 | 3/2006 | Wolner |
| 2006/0087440 A1 | 4/2006 | Klein |
| 2006/0117619 A1 | 6/2006 | Costantini |
| 2006/0119525 A1 | 6/2006 | Cohen |
| 2006/0184376 A1 | 8/2006 | Graves |
| 2006/0217995 A1 | 9/2006 | Sagnak |
| 2007/0006494 A1 | 1/2007 | Hayes |
| 2007/0021971 A1 | 1/2007 | McKinney |
| 2007/0022576 A1 | 2/2007 | Christanio |
| 2007/0067227 A1 | 3/2007 | Ikeda |
| 2007/0124155 A1 | 5/2007 | White |
| 2007/0124972 A1 | 6/2007 | Ratcliffe |
| 2008/0015463 A1 | 1/2008 | Goldstein |
| 2008/0018472 A1 | 1/2008 | Dasilva |
| 2008/0021717 A1 | 1/2008 | Kaartinen |
| 2008/0021718 A1 | 1/2008 | Kaartinen |
| 2008/0021905 A1 | 1/2008 | Kaartinen |
| 2008/0021919 A1 | 1/2008 | Kaartinen |
| 2008/0106088 A1 | 5/2008 | Rohlf |
| 2008/0106398 A1 | 5/2008 | Rohlf |
| 2008/0108261 A1 | 5/2008 | Swan |
| 2008/0125672 A1 | 5/2008 | Burrows |
| 2008/0159547 A1 | 7/2008 | Schuler |
| 2009/0283596 A1 | 11/2009 | Grummett |
| 2010/0119074 A1 | 5/2010 | Devianant |
| 2010/0135502 A1 | 6/2010 | Keady |
| 2010/0142725 A1* | 6/2010 | Goldstein ............... G10L 19/00 381/92 |
| 2011/0006894 A1* | 1/2011 | Witwer .................. G06Q 10/06 340/539.11 |
| 2012/0305329 A1* | 12/2012 | Keady ..................... A61F 11/10 181/135 |
| 2013/0094658 A1 | 4/2013 | Holter |
| 2013/0179359 A1 | 7/2013 | Burns |
| 2014/0156032 A1 | 6/2014 | Jenkins |
| 2014/0307076 A1 | 10/2014 | Deutsch |
| 2016/0148132 A1* | 5/2016 | Aqlan ................. G06Q 10/0635 705/7.16 |

(56) References Cited

U.S. PATENT DOCUMENTS

| | | | | |
|---|---|---|---|---|
| 2016/0199241 A1* | 7/2016 | Rapoport | ............ | A61F 7/0053 600/22 |
| 2016/0364456 A1 | 12/2016 | Trenchard | | |

FOREIGN PATENT DOCUMENTS

| | | | | |
|---|---|---|---|---|
| DE | 03932066 | | 11/1990 | |
| DE | 19816396 | | 11/1999 | |
| DE | 19842366 | | 3/2000 | |
| DE | 10008048 | | 9/2001 | |
| EP | 0692774 | | 1/1996 | |
| EP | 0788069 | | 8/1997 | |
| FR | 2593219 | | 7/1987 | |
| FR | 2704604 | | 11/1994 | |
| FR | 2801998 | | 6/2001 | |
| GB | 2398454 | | 8/2004 | |
| JP | S62-003625 | | 1/1987 | |
| JP | H06299799 | | 10/1994 | |
| JP | 2004-185476 | | 7/2004 | |
| JP | 2004-033651 | | 11/2004 | |
| JP | 2004-343834 | | 12/2004 | |
| KR | 20160096803 | | 8/2016 | |
| RU | 10387 | U1 | 7/1999 | |
| WO | WO 1996-012523 | | 5/1996 | |
| WO | WO 1996-012524 | | 5/1996 | |
| WO | WO 1997-016963 | | 5/1997 | |
| WO | WO 1998-035243 | | 8/1998 | |
| WO | WO 1999-019851 | | 4/1999 | |
| WO | WO 2001-043827 | | 6/2001 | |
| WO | WO 2001-080198 | | 10/2001 | |
| WO | WO 2002-002191 | | 1/2002 | |
| WO | WO 2002-085106 | | 10/2002 | |
| WO | WO 2004-008900 | | 1/2004 | |
| WO | WO 01/58064 | | 7/2005 | |
| WO | WO 2006-123134 | | 11/2006 | |
| WO | WO 2009-032417 | | 3/2009 | |
| WO | WO 2009-051896 | | 4/2009 | |
| WO | WO 2010-030889 | | 3/2010 | |
| WO | WO-2010030889 | A1* | 3/2010 | ............ H04R 29/00 |
| WO | WO 2011/050401 | | 5/2011 | |
| WO | WO 2016-168486 | | 10/2016 | |

OTHER PUBLICATIONS

"2-Piece Assembly Ratchet Rivets", ITW Fastex, URL<http://www.itw-fastex.com/catalog/026>, 2 pages (known of prior to Jun. 2006).

"'Brand' New-Imperial College London learns the benefits of Safetrak", 1 page (known of prior to Jun. 2006).

"DBI Sala—User Instruction Manual—Self Retracting Lifelines", DB Industries, 2007, 40 pages.

"Electronic ID", Allflex USA, [retrieved from internet on Jun. 3, 2006], URL <http://www.allflexusa.com/eid/eid.php>, 6 pages.

"HandiGrimpe—Traceability Tools", BEAL, [retrieved from the internet on May 24, 2007], URL <http://www.beal-intervention.com>,6 pages (known of prior to Jun. 2006).

"Low Frequency RFID Evaluation Kit—Reference Guide", Texas Instruments, Sep. 2002, 4 pages.

"Pervidi™", Techs4Biz Corporation, 2006, URL<http://www.pervidi.com>, 11 pages.

"Pocket Jobsite® Inspector", 2002, URL<http://www.pdage.com>, 1 pages.

"Sealed Self Retracting Lifeline—50 ft. cable 3403400", Capital Safety, 2007 URL<http://www.capitalsafety.com>, 1page.

"Tags", Safetrak, 2007, URL<www.safetrack.com>, 3 pages (known of prior to Jun. 2006).

"The Tracker", French Creek Production, 2002, URL<http://www.frenchcreekproduction.com/tracker.htm>, 2 pages.

"Harnesses", Safetrak, URL<www.safetrak.com>, 2007, 4 pages.

"HDX High Performance Ultra EID Tag—ISO Compliant, 2006, Allflex®", URL<http://www.allflexusa.com>, 2 pages.

"Notice of Use—Beal Software", Beal Services, 2001, 18 pages.

"ReefPoint Technology", HOA Inspector™, URL<http://www.reefpt.com>, 4 pages (known of prior to Jun. 2006).

"RFID Tracking Solutions" and 4 on-line brochures, Infochip Systems Inc, 2003, URL<http://www.infochip.com>, 13 pages.

"Safety Management Systems—Safetrak", Scafftag Safety Systems, 2007, URL<http://www.scafftag.com>, 7 pages.

"Safety Management Systems—Unitag", Scafftag Safety Systems, 2007, URL<http://www.scafftag.com>, 5 pages.

Kitamura, "Using Ubiquitous Networks to Create New Services Based on the Commercial and Public Infrastructure". Sep. 1, 2002, Nomura Research Institute, No. 54, pp. 01-12.

Portal for safety and security, Git-Sicerheit.de, 2011, 1page.

SAFETRAK, "Harnesses", 1page.

Scafftag® Press Release, "Micro tag® Makes Harnesses Safer", 2007, 1 page.

Scafftag® Press Release, "Scafftag® Limited—The Past, Present and Future", Scafftag, Jun. 2007, 1 page.

Solo™ Occupational DBMS, Benson Medical, 2pages.

Swedberg, "Safety harnesses get smart", RFID Journal, 2006, pp. 01-02.

Tool Hound brochure, URL<http://www.toolhound.com>, 1 page. (known of prior to Jun. 2006).

Tool Watch Products, Tool Watch, URL<http://www.toolwatch.com/accessorieslabelstags>, 2 pages.

Zgraggen, "Tool Loss: Seeing Red???", Construction Business Owner, Mar. 2006, pp. 10-12 and 14.

International Search report for PCT International Application No. PCT/US2017/021118 dated Apr. 21, 2017, 5 pages.

* cited by examiner

300

| Hearing Conservation ▼ | Program Guide | Task Manager | ⌂ Overview |
|---|---|---|---|
| Setup  Measure  Noise Control  Audiometric Testing  Hearing Protection  Training  Evaluation |

Setup Describe your program goals and workplace.

GOALS

Capture in words the goals of your HLCP program.

| | |
|---|---|
| Company | Acme Inc. |
| Program Goals | Acme is adopting a hearing conservation program to help reduce the noise exposure od our workers. |
| Country | Select ▼ |
| Regulatory Body | Select ▼ |
| Exposure Limit | Select ▼  Type ▼ |

⎯⎯ 302

ADMINISTRATION

Describe who is responsible for the administration of the program

| | | |
|---|---|---|
| Professional Supervisor | Select ▼ | Security Level ▼ |
| Audiometric Technician | Select ▼ | Security Level ▼ |
| Noise Survey Technician | Select ▼ | Security Level ▼ |
| Physician | Select ▼ | Security Level ▼ |
| Nurse | Select ▼ | Security Level ▼ |

WORKER GROUPS
Create groups for your workers. These should be logical groupings.

Shift A
Shift B
Welders
Engine Room

[ + Add Worker Group ]  ⎫
                        ⎬ 402
                        ⎭

WORKERS
Add workers and then click on their workgroups and areas.

| worker | area | | | | ⎫ |
|---|---|---|---|---|---|
| Able, B. | Assembly | CNC Shop | Loading Dock | Shop Floor | Shift A | Shift B | Welders | Engine Room |
| Bartsal, T. | Assembly | CNC Shop | Loading Dock | Shop Floor | Shift A | Shift B | Welders | Engine Room |
| Cunning, H. | Assembly | CNC Shop | Loading Dock | Shop Floor | Shift A | Shift B | Welders | Engine Room |
| Everet, E. | Assembly | CNC Shop | Loading Dock | Shop Floor | Shift A | Shift B | Welders | Engine Room |
| Falway, D. | Assembly | CNC Shop | Loading Dock | Shop Floor | Shift A | Shift B | Welders | Engine Room |
| Harbaugh, J. | Assembly | CNC Shop | Loading Dock | Shop Floor | Shift A | Shift B | Welders | Engine Room |

(columns at right braced as 404)

[ + Add Worker ]   ⊕ Import Workers from a File

PERSONNEL PROTECTIVE EQUIPMENT IN-USE
Define the PPE types in use at your company.

Earplugs
Earmuffs
Custom Earplug

[ + Add PPE Type ]  ⎫
                    ⎬ 406
                    ⎭

[ Back ]   [ Next ]

| Hearing Conservation ▼ | Program Guide | Task Manager |

Setup  Noise Control  Audiometric Testing  Hearing Protection  Training  Evaluation ⊞ Overview

Measure  Describe the sources of noise and noise measurements obtained in this area.

NOISE SOURCES
Describe the noise sources in the workplace.

EQUIPMENT
CNC Mulberry 8200
Conveyor System

AREA
[CNC Shop ▼]
[Select Area ▼]

[+ Add Noise Sources]

AREA NOISE EVALUATIONS
Describe the sound level meters used and the area noise measurements obtained in this area.

| AREA | MEASUREMENT GOALS | LATEST MEASUREMENT | USING INSTRUMENT | | |
|---|---|---|---|---|---|
| Shop Floor | Measure Monthly ▼ | 68 dBA, 14 days ago ᵈᵇ | Sound Meter | Smart Phone | ■ |
| CNC Shop | Measure Yearly ▼ | 86 dBA, 45 days ago ᵈᵇ | SE-400 | Octave Band | ■ |
| Assembly | Custom ▼ | 76 dBA, 27 days ago ᵈᵇ | 62X Series | Sound Level Meter | ■ |

[+ Add Noise Sources]

*FIG. 5A*

NOISE EXPOSURE EVALUATIONS

Describe the noise measurement equipment being worn and the samples obtained in this area.

| WORKER/GROUP | HAS HEARING SHIFT | LAST MEASUREMENT | DOSE | USING INSTRUMENT |
|---|---|---|---|---|
| Max, T. | ☒ | 95 dBA 21 days ago | 200% | Axis 3700B Dosimeter |
| Welder Group | ☐ | 86 dBA 14 days ago | 85% | Meter Pro Sound Level Meter |
| Wencel, M. | ☒ | 91 dBA 1 day ago | 110% | Axis 3700B Dosimeter |

[ + Add Personnel Noise Measurements ]

HISTORY

Area Measurement History

Baseline 80 dBA Jun-1-2015

| 76 dBA | 79 dBA | 78 dBA | 92 dBA |
| Jul-11-2015 | Jul-21-2015 | Sep-7-2015 | Oct-28-2015 |
| Noise Pro by | Smart Phone | Noise Pro by | Noise Pro |
| Smith, J. | Smith, J. | Smith, J. | by Mark Mueller |

Maintenance History

| Activity | Notes | Date | User |
|---|---|---|---|
| Equipment Installation | Installation Completed | Dec-22-2014 | Bart Randolf |
| Calibration | Equipment calibrated | Apr-20-2015 | John Aybar |
| Replace Part | Noise measurements in CNC Shop were out of range, determined the nozzle needed replacement | May-22-2015 | Bart Randolf |

FIG. 6

| AREA ADMINISTRATIVE CONTROLS | TYPE AND AREA | | LIMITS | POLICY |
|---|---|---|---|---|
| Describe the admin controls and capture policy information | Work group ▼ | CNC Shop ▼ | Time/Date Limits ▼ | 2 hours per day max  edit |
| | Process ▼ | Assembly ▼ | Procedural Limits ▼ | Turn off the crusher when in the area  edit |
| | Work group ▼ | Shop Floor ▼ | Time/Date Limits ▼ | Cap hours of exposure at 8 hrs  edit |

EQUIPMENT HISTORY

Maintenance History

| Activity | Notes | Date | User |
|---|---|---|---|
| Equipment Installation | Equipment completed | Jan-22-2015 | Bart Randolf |
| Quarterly Maintenance | First maintenance No issues found | Apr-20-2015 | John Aybar |
| Replaced Part | Noise measurements were out of range determined the nozzle needed replacement | May-22-2015 | Bart Randolf |
| Quarterly Maintenance | No issues | Jul-18-2015 | John Aybar |
| Quarterly Maintenance | No issues Equipment operating properly | Oct-3-2015 | John Aybar |

+ add entry

Close

MAINTENANCE RECORDS

Maintenance History for the Noise dBA Saver

| Date | Activity | Notes | Person |
|---|---|---|---|
| Feb-02-2015 | Initial Install | Installed barrier between wall and machine to reduce refracted noise. | Hearing Solutions Inc. |
| Apr-16-2015 | Quarterly Maintenance | Followed manufacturer recommendations on cleaning and measurement. | Jane Smith |
| Jul-08-2015 | Quarterly Maintenance | No issues. Measurement taken in CNC Lab. | Jane Smith |
| Jul-29-2015 | Configuration | Moved the sound barrier to improve noise reduction between CNC1 and 2. | Bill Buxton |

+ add New Maintenance Entry

Cancel   Save

Audiometric Testing
In this section we edit the schedule for worker audiometric testing and results.

Schedule | Workers

SCHEDULE
Here we set the schedule for audiometric testing.

| AREA | ADDITIONAL CONTROLS | LAST GROUP MEASUREMENT | NEXT TEST DATE |
|---|---|---|---|
| CNC Shop | Measure Quarterly ▼ | 4 days ago | 86 days |
| CNC Shop | Measure Yearly ▼ | 8 months ago | 4 months |
| Assembly | Measure Yearly ▼ | 13 months ago | TBD |

⟩ 1102

WORKERS WITH A HEARING SHIFT
Workers with a hearing shift and measurement information.

| WORKER | HAS HEARING SHIFT | OSHA RECORDABLE | HEARING PROTECTION | LAST MEASUREMENT | AUDIOGRAM |
|---|---|---|---|---|---|
| Ruckheim, H. | ☒ | ☒ | None | 94 days ago | ılı. |
| Smith, T. | ☒ | ☐ | Earplugs | 4 days ago | ılı. |
| Travers, P. | ☒ | ☒ | Earmuffs | 7 day ago | ılı. |

⟩ 1104

+ Add Worker with Hearing Shift

Setup  Measure  Noise Control  Hearing Protection  Training  Evaluation

Hearing Conservation ▼  Program Guide  Task Manager  Audiometric Testing  ⌂ Overview

*FIG. 11A*

UPCOMING AUDIOMETRIC TESTS

Audiometric tests that are coming up by area.

| DATE | AREA | PROVIDER | REVIEWER |
|---|---|---|---|
| In 7 Days | Shop Floor B | Plant Nurse ▾ | Tim Zorn ▾ |
| In 2 Weeks | Shipping | ABC Mobile Test ▾ | Mary Smith ▾ |
| In 3 Weeks | Assembly A | Plant Nurse ▾ | Tim Zorn ▾ |

AUDIOMETRIC RETESTS

Audiometric tests that are coming up by area.

| DATE | AREA | PROVIDER | REVIEWER |
|---|---|---|---|
| ● In 2 days | Shop Floor A | Plant Nurse ▾ | Tim Zorn ▾ |

+ Schedule Audiometric Re-Test

TRAINING MATERIALS

Additional training materials are available on the training tab

▲ Audiometric Testing Guide
3:32 min

▲ What to Expect When Taking Your First Audiometric Test
2:02 min

▲ Understanding Your Audiogram Results
4:06 min

View all Training Materials

Back    Next

HEARING PROTECTION PRODUCTS

Hearing protection products that can be implemented in your workplace.

| Yellow Foam Earplug NRR 25 dB | Easy Earmuff NRR 25 dB | Washable earplug NRR 25 dB | Orange Earplug NRR 33 dB | No Roll earplug NRR 24 dB |

Snug Earplugs NRR 29 dB

Swirl Earplug NRR 33 dB

Search

+ Add Product

Back | Next

Hearing Conservation ▼ | Program Guide | Task Manager

Setup  Measure  Noise Control  Audiometric Testing  Hearing Protection  Training  Evaluation        ⌂ Overview

Training Schedule and track training sessions and worker surveys.

Schedule  Library

TRAINING
SCHEDULE

These are the
training sessions that
are scheduled.

| COURSE | INSTRUCTOR | INVITED |
|---|---|---|
| Employee Hearing Protection | Smith, J. | 146 |
| Personal Sound Measurement Devices | Smith, J. | 152 |
| When and Where to Wear | Smith, J. | 151 |
| + Schedule Training | | |

{ 1402        { 1404

HISTORY

These are the
training sessions that
are scheduled.

| COURSE | DATE | ATTENDEES | ABSENT | RESULTS |
|---|---|---|---|---|
| Hearing Protection Refresher Course | Jul-15-2015 | 152 | 0 | View |
| Care and Maintenance (follow-up) | May-29-2015 | 3 | 0 | View |
| Care and Maintenance | May-22-2016 | 149 | 3 | View |
| Sound Barrier Installation Impact | May-1-2016 | 146 | 6 | View |

Back        Next

| ⌒ Hearing Conservation ▼ | Program Guide | Task Manager |

Setup    Measure    Noise Control    Audiometric Testing    Hearing Protection    Training    Evaluation    ⊡ Overview

Training Results Capture your comments on this training session and schedule a follow-up for absent attendees.                       ⎫
                                                                                                                                      ⎬ 1602
EAR PROTECTION REFRESHER COURSE                                                                                                        ⎭

Date  Jul-15-2015

Attendees  152
Absent     0

Training Results Comments and Notes
These notes will appear in the permanent history

Follow-up Training
☐ Schedule Follow-up
[mm/dd/yyyy] 📅
☐ Send schedule email to attendees

[Back]  [Next]

| Hearing Conservation ▼ | Program Guide | Task Manager | | | | | ⛓ Overview |
|---|---|---|---|---|---|---|---|
| Setup | Measure | Noise Control | Audiometric Testing | Hearing Protection | Training | Evaluation | |

Evaluation Evaluate your program and survey workers on the effectiveness of your program Dashboard  <u>Surveys</u>

1802 ⎵  1804 ⎵

Sound Protection Survey
A survey of all workers and whether they need training for their admin controls.

ACTIVE SURVEYS
Survey's that are in progress.

| Started | Ends | Taken | Pending | Follow-ups | Results and Actions |
|---|---|---|---|---|---|
| 23 days ago | 1 day | 112 | 24 | 12 | |

Preview the Survey

SURVEY HISTORY
Recent worker and staff surveys

| Survey | Completion Date | Participants | Results |
|---|---|---|---|
| Satisfaction Survey | Jul-15-2015 | 152 | View |
| Testing Days Survey | May-22-2015 | 149 | View |
| Performance Review | May-1-2015 | 156 | View |
| Survey about Surveys | Apr-15-2015 | 153 | View |
| Another Survey for Workers | Apr-3-2015 | 123 | View |

TRENDS THIS YEAR

AUDIOGRAMS
8% ▼ worse

STS CASES
4 ▲ new

WORKERS
21 with hearing shift

TRAINING
75% training completed 12/17-2015

Add a Custom Tile

Back    Done

*FIG. 18*

Survey Results  Capture your comments on this survey

Hearing Protection Survey
A survey given to all workers on their training status and follow-up action.

Survey Ongoing Ends in 1 day

Participants   112 Complete
               24 Pending

Question 1   Are you satisfied with the hearing protection that you are provided by Acme Inc?
Yes 86%
No 14%

Question 2   Have you received training for your hearing protection?
Yes 92%
No 8%

Question 3   Would you like the training staff to contact you about additional training?
Yes 99%
No Setup   Measure   Noise Control   Audiometric Testing   Hearing Protection   Task Manager Hearing Conservation | Program Guide | Task Manager Training   Evaluation   Overview 1900
1902

FIG. 19A

Survey Results Comments and Notes
Notes and follow-up training schedule.

Follow-up Training
☑ Schedule Follow-up
mm/dd/yyyy 🗓
☐ Send schedule email to attendees

1904

Save
Close

FIG. 19B

| Hearing Conservation ▼ | Program Guide | Task Manager |

Task Manager
The task manager provides a go-to reference for important tasks and activities.

② Notifications

Noise Survey data received today — View / Import
Training Report received from ABC Mobile Test — View / Import

MARCH

SCHEDULE TASKS
- Schedule an Area Measurement
- Create a New Task for a Worker
- Schedule Training

⑧ Tasks Due This Week

⚠ Mary, B. for STS follow-up - 5 Days Late
⚠ Shop Floor Measurement - 1 DAy Late
● Thomas, J. is overdue for a hearing test — Schedule Test
Jones, J. hearing loss OSHA log entry - due in 2 days

*FIG. 20A*

Other Tasks Due This Month

Jimmy, S. due for fit testing 03/12/2016

Sandy, B. due for Audiogram due 03/12/2016

CNC Shop crew employee hearing conservation training due 03/21/2016

2004

Due This Quarter

Assembly Area work group due for fit testing May 2016

CNC Shop work area Noise Mapping due May 2016

INTELLIGENT SAFETY MONITORING AND ANALYTICS SYSTEM FOR PERSONAL PROTECTIVE EQUIPMENT

TECHNICAL FIELD

The present application relates generally to the field of safety management. More specifically, the present application relates to an intelligent safety system.

BACKGROUND

Maintaining the safety and health of workers is a concern across many industries. Various rules and regulations have been developed to aid in addressing this concern. Such rules provide sets of requirements to ensure proper administration of personnel health and safety procedures. To help in maintaining worker safety and health, some individuals may be required to don, wear, carry, or otherwise use a personal protective equipment (PPE) article, if the individuals enter or remain in work environments that have hazardous or potentially hazardous conditions.

Known types of PPE articles include, without limitation, respiratory protection equipment (RPE), e.g., for normal condition use or emergency response; protective eyewear, such as visors, goggles, filters or shields; protective headwear, such as hard hats, hoods or helmets; hearing protectors; protective shoes; protective gloves; other protective clothing, such as coveralls and aprons; protective articles, such as sensors, safety tools, detectors, global positioning devices, mining cap lamps and any other suitable gear.

One determination a worker may make with respect to a PPE is whether or not it remains functional and effective given the amount of use that it has undergone. Amount of use can include the amount of time the PPE was worn, whether the PPE was properly worn for that time period, the amount of time the PPE was powered or otherwise actively used, and the level of exposure in the environment to which the PPE is subjected.

SUMMARY

This disclosure is directed to techniques and systems that provide intelligent monitoring and analytics for workers and personal protective equipment data in relation to work environments based on real-time and historical data. Specifically, techniques and systems of this disclosure may provide for end-to-end recommendation, notification, trend analysis, anomaly analysis, and control of workers and personal protective equipment in a work environment. By detecting, for example, different hazards in a work environment, such as sound hazards, techniques and systems of the present disclosure may recommend personal protective equipment that improves or maintains a worker's safety. In some examples, the techniques and systems may notify or alert workers and/or other users on a per-location basis based on real-time and/or historical location detection of the worker in relation to the hazards. The techniques may further determine whether worker health is changing in response to hazards in a work environment, and may determine such changes across similarly or differently situated worker populations. In some instances, the techniques and systems may recommend that workers move to different locations in a work environment throughout the day to optimize and/or improve worker safety with respect to hazards to which the workers are exposed. Systems and techniques of this disclosure may further identify articles of machinery that require maintenance based on abnormal sound, temperature or other detected characteristics of the articles of machinery. These and other techniques and systems of this disclosure may improve the accuracy and response-time for detecting the impact of hazards on worker health in a work environment, and in some instances with respect to personal protective equipment assigned to workers.

The details of one or more examples are set forth in the accompanying drawings and the description below. Other features, objects, and advantages of the disclosure will be apparent from the description and drawings, and from the claims.

BRIEF DESCRIPTION OF THE DRAWINGS

FIGS. 3A-3B illustrate a user interface that may be generated and output for display by an application, in accordance with one or more techniques of this disclosure.

FIG. 4 illustrates a user interface that may be generated and output for display by an application, in accordance with one or more techniques of this disclosure.

FIGS. 5A-5B illustrate a user interface that may be generated and output for display by an application and that includes set up options related to noise information in accordance with one or more techniques of this disclosure.

FIG. 6 illustrates a user interface that may be generated and output for display by an application and that includes noise measurement information related to an area in accordance with one or more techniques of this disclosure.

FIGS. 8A-8B illustrate a user interface that may be generated and output for display by an application and that includes noise controls and administrative controls for various areas in accordance with one or more techniques of this disclosure.

FIGS. 9A-9B illustrate a user interface that may be generated and output for display by an application and that includes worker administrative controls, training materials and equipment history in accordance with one or more techniques of this disclosure.

FIG. 10 illustrates a user interface that may be generated and output for display by application and that includes maintenance records in accordance with one or more techniques of this disclosure.

FIGS. 11A-11B illustrate a user interface that may be generated and output for display by application and that includes information related to audiometric testing in accordance with one or more techniques of this disclosure.

FIGS. 13A-13B illustrate a user interface that may be generated and output for display by an application and that includes information related to hearing protection products and workers using hearing protection in accordance with one or more techniques of this disclosure.

FIG. 14 illustrates a user interface that may be generated and output for display by an application and that includes information relating to training schedules and training history in accordance with one or more techniques of this disclosure.

FIG. 16 illustrates a user interface that may be generated and output for display by application and that includes training results in accordance with one or more techniques of this disclosure.

FIG. 18 illustrates a user interface that may be generated and output for display by an application and that includes evaluation information such as active surveys and survey history in accordance with one or more techniques of this disclosure.

FIGS. 19A-19B illustrate a user interface that may be generated and output for display by application and that includes survey results in accordance with one or more techniques of this disclosure.

FIGS. 20A-20B illustrate a user interface that may be generated and output for display by an application and that includes task manager information in accordance with one or more techniques of this disclosure.

DETAILED DESCRIPTION

Figure 1A:
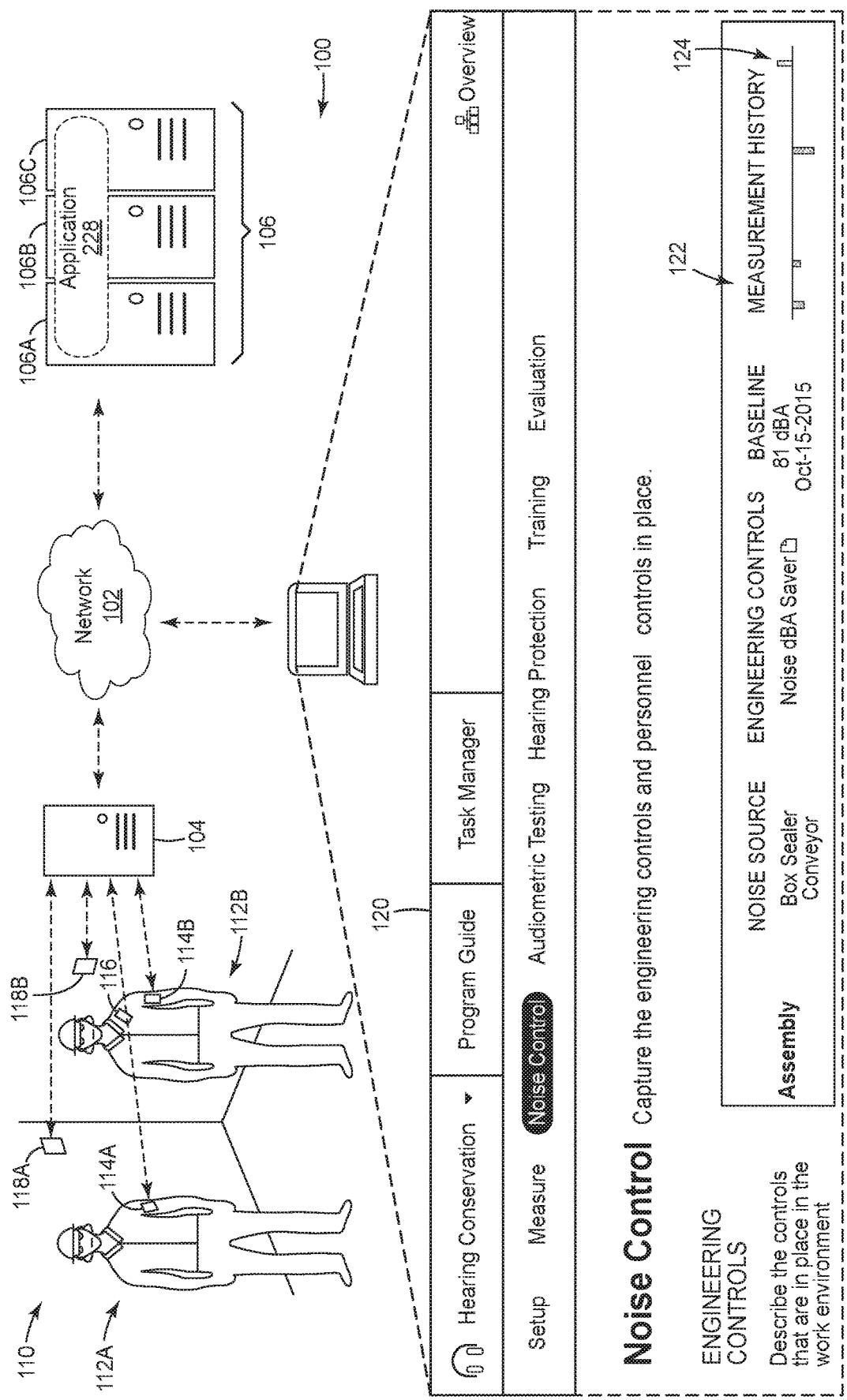
FIG. 1A is a block diagram illustrating an example intelligent safety system, in accordance with techniques of this disclosure.

FIG. 1A is a block diagram illustrating an example intelligent safety system 100, in accordance with techniques of this disclosure. As shown in FIG. 1A, system 100 includes a network 102, worksite computing device 104, data center computing devices 106A-106C, and user computing device 108. FIG. 1A further illustrates a work site 110 in which workers 112A and 112B may perform various tasks. Examples of work site 110 may include a mine, factory, manufacturing site, construction site, disaster site, airfield, railroad, shipping yard, or pharmaceutical laboratory to name only a few examples. Such work sites may expose workers various types of hazards including elevated noise levels, which may present hearing hazards to workers 112. In some examples of this disclosure, "noise" and "sound" may be used interchangeably. In some examples of this disclosure, "work site" and "work environment" may be used interchangeably.

Safety system 110 may implement a safety program, such as a hearing conservation program for workplaces that provide the potential for human hearing damage or loss, tinnitus, and associated disorders. Specifically, safety system 110 may map noise or hearing hazards to various locations, control the exposure to hearing protection (e.g., hearing protection device), validate hearing protection, and perform monitoring and alerting based on the safety program to name only a few examples. As further described in this disclosure, safety system 100 may provide end-to-end integration of information from worksite devices to data center computing devices 106, which implement analytical techniques to detect and automatically respond to potential human hearing loss events. Although systems and techniques of this disclosure are described with respect to a hearing conservation program to prevent and manage hearing loss, such systems and techniques may also be applied to other types of worker safety. For instance, systems and techniques of this disclosure may be adapted to fall protection PPE; head, eye, or face PPE; welding PPE; respiratory PPE, or any other suitable types of PPE. In this way, safety system 110 may be extended to support any number of different types of PPE in the same or similar manner as described with respect to hearing conservation and safety in the examples of this disclosure.

In the example of FIG. 1A, workers 112A-112B ("workers 112") may be individually "fit-tested" with hearing protection prior to entering worksite 110. Hearing protection may include inner ("insert") ear hearing protection and outer (or "circumaural") ear protection. Inner ear protection may include earplugs or any other protection that is inserted at least partially into the ear canal. Outer ear protection may include earmuffs or any other protection that covers or surrounds the ear of the worker. Fit-testing may include equipping a worker with hearing protection and testing a level or the amount of noise reduction that the worker receives from the hearing protection. For instance, a fit-testing system (not shown) may provide a variety of audible outputs to a worker while hearing protection is worn and noise levels may be measured by the fit-testing system using a microphone array. In some examples, the microphone may measure sound levels both inside the worker's ear canal and outside the hearing protection worn by the worker. The fit-testing system may determine, on a per-worker or per-ear basis, the level of noise reduction that the worker receives from the hearing protection device as it was worn by the worker.

In the example of FIG. 1A, the fit-testing system may perform fit-testing for hearing protection worn by each of workers 112A and 112B. In some examples, the fit-testing system may be communicatively coupled (via wired and/or wireless communication) or otherwise integrated with data center computing devices 106, such that noise levels measured by the fit-testing system and/or any values generated based on the noise levels are stored in one or more of data center computing devices 106. In some examples, the type of hearing protection worn for the fit-testing, the identity of the worker engaged in the fit-testing, and any other information associated with the fit-testing may be sent by the fit-testing system to data center computing devices 106 for storage. In this way, application 228 may access such fit-testing information when performing techniques of this disclosure. In some examples, an operator of the fit-testing equipment may access a user interface provided by application 228 to submit such fit testing information to data center computing devices 106.

Once a worker has been fit-tested, the worker may enter worksite 110 with the hearing protection for which the worker was fit-tested. To measure noise levels in worksite 110, one or more workers, such as worker 112B, may be equipped or otherwise fitted with a sound level monitor 116 that is proximate to or attached to worker 112B. Although a sound level monitor is referred to in the example of FIG. 1A, the term "sound level monitor" may be interchangeably used or refer to as a noise dosimeter in accordance with techniques of this disclosure. In other examples, a sound level monitor may be a device that measures sound intensity at a particular point in time. In some examples, sound intensity may refer to sound pressure, or alternatively, sound exposure or sound dose. In some examples, a sound level monitor includes the functionality of a dosimeter. A noise dosimeter may measure noise level values, such as dose, peak, upper limit (UL), run time, threshold, exposure, $L_{avg}/L_{eq}$ (where L is level), max noise level, projected dose, min noise level, to name only a few examples. Sound level monitor 116 may send such noise level values to worksite computing device 104 (or directly to data center computing devices 106) on a real-time, periodic, or asynchronous basis. Worksite computing device 104 (or sound level monitor 116) may send noise level values to data center computing devices 106 via network 102.

Figure 1B:
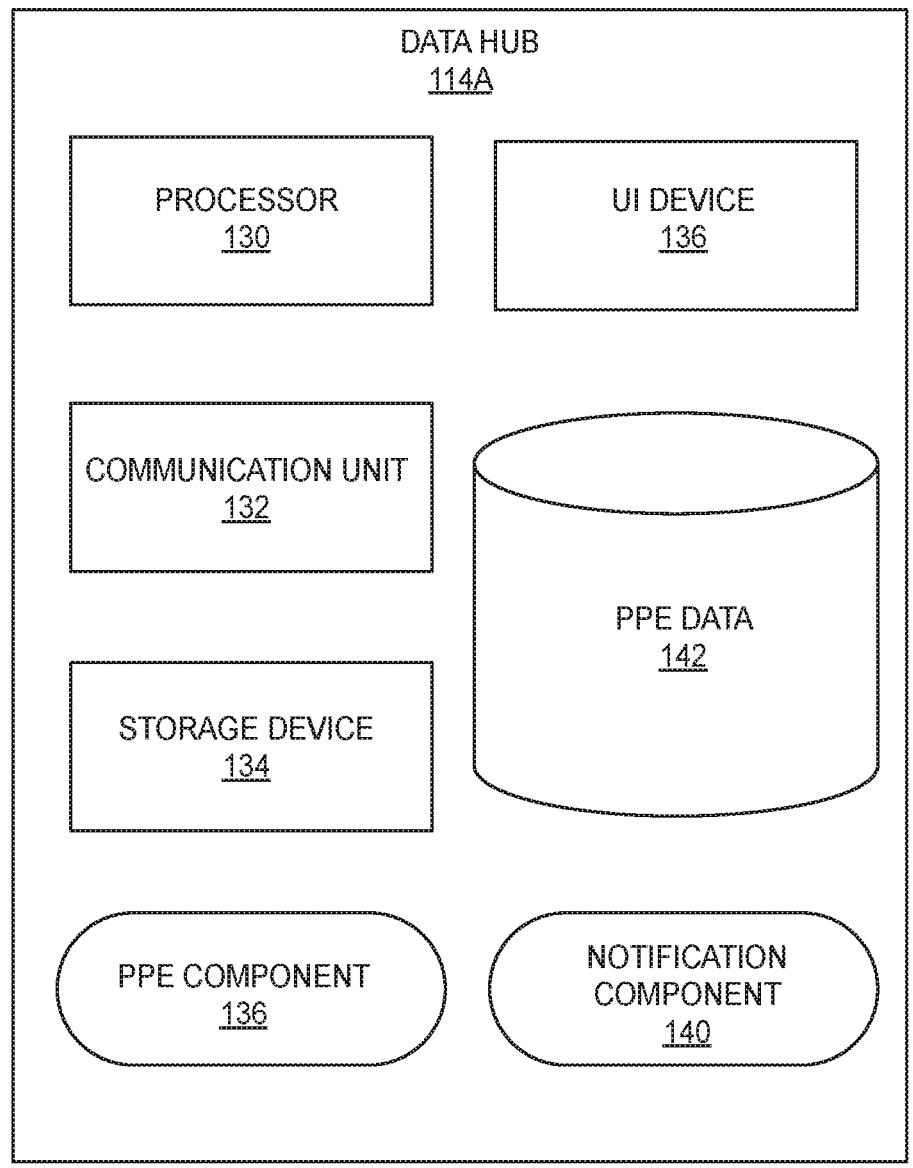
FIG. 1B illustrates a data hub as shown in FIG. 1A, in accordance with techniques of this disclosure.

In some examples, each of workers 112A and 112B may instead or additionally each be equipped or otherwise fitted with portable computing devices 114A and 114B (further described in FIG. 1B). Portable computing device 114A may communicate with any one or more of portable computing device 114B, worksite computing device 104 and/or data center computing devices 106. Portable computing device 114A may determine geolocation information (or relative or absolute location in a work environment) of worker 112A, other portable computing devices proximate to computing device 114B, worksite identification information, or any other information relating to worksite 110 or other workers wearing portable computing devices, such as worker 112B. By providing information to data center computing devices 106 that is captured or generated at worksite 110 by portable computing devices 114, application 228 may determine based on one or more of geolocation, proximity information, and/or worksite identification information, that worker 114A is being exposed to the same or similar noise levels as worker 114B, although worker 114A is not equipped with a dosimeter.

Portable computing devices 114A and 114B may also communicate with other electronic or communication devices, such as Bluetooth beacon devices that include computing or memory components and Bluetooth communication capabilities. Portable computing devices 114A and 114B may also communicate with smart tags, including active or passive RFID tags as described in WO2009/051896 to Insley et al., incorporated herein by reference. Smart tags may also include optical or acoustic wave tags that provide data through visual or audio medium. Such smart tags or other electronic or communication devices may be attached to, associated with, or part of personal protective equipment (PPE), for example, hearing protection including active or passive earmuffs or insert hearing protectors. A smart tag may include data such as but not limited to: an identifier that uniquely identifies the article of PPE to which the tag is associated or attached, data descriptive of the operation of the article of PPE, a unique identifier of the user of the article of PPE or any other suitable data.

In some instances, smart tags or other electronic or communication devices may be attached to other types of PPE, including, without limitation, respiratory protection equipment, protective eyewear, such as visors, goggles, filters or shields, protective headwear, such as hard hats, hoods or helmet, protective shoes, protective gloves, other protective clothing such as coveralls and aprons, protective articles, such as sensors, safety tools, detectors, global positioning devices, mining cap lamps and any other suitable gear. Safety system 100 may include such types of PPE and may track information related to PPE.

In some instances, portable computing device may communicate with environmental sensors 118A and 118B. Environmental sensors may detect information about the area or work environment where workers 112A and 112B are present. For example, environmental sensors 118A and 118B may be a dosimeter and may detect noise information as described herein. In some instances, environmental sensors may detect other types of information about an environment such as hazardous information including electromagnetic radiation, ionizing radiation, nuclear radiation, chemicals, biological analyst, particulates, heat, motion as well as others, as described in WO 2009/032417 to Holler et al., incorporated herein by reference. In some examples, environmental sensors 118A and 118B could be RFID readers or other readers communicatively coupled to worksite computing device 104. When workers 112 enter and exit worksite 110, environmental sensors 118 may detect the entry and exit of the workers based on communication with portable computing devices 114 or other equipment. Environmental sensors 118 may also provide location information. For instance, environmental sensor 118*s* may be beacons or other devices that provides a location that may be detected by a computing device, such as portable computing devices 114. Any data generated by environmental sensors may be received by portable computing devices 114, worksite computing devices 104, and/or data center computing devices 106, and used by application 228 in accordance with techniques of this disclosure.

In the example of FIG. 1A, workers 112A and 112B may perform tasks at worksite 110 as a team and therefore operate in substantial proximity to one another, for example, within a threshold distance of one another. Example threshold distances may include 5 meters, 10 meters, 20 meters, or 50 meters. Example threshold distances may be included within a range of 5-10 meters, 5-10 meters, or 5-50 meters. When entering worksite 110, entry of workers 112A and 112B to worksite 110 may be indicated using a badge, portable computing device 114, or any other identifying device. For instance, worksite 110 may include one or more readers, beacons, or other computing devices that may detect the worker's badge, portable computing device 114A, or any other identifying device. Alternatively, portable computing device 114A may detect the readers, beacons, or other computing devices. In either case, portable computing device 114A or a reader, beacon, or other identifying device may send a set of data to worksite computing device 104 or data center computing devices 106. Worksite computing device 104 may send the set of data to data center computing devices 106. The set of data may include, but is not limited to, a worksite identifier, a timestamp, and a unique worker identifier. Application 228 may later use such sets of data in accordance with techniques of this disclosure.

While workers 112A and 112B are operating within worksite 110, sound level monitor 116 may detect noise levels and store information representing noise levels. Sound level monitor 116 may send the information representing noise levels to worksite computing device 104, which sends the information to data center computing devices 106. Alternatively, sound level monitor 116 may send the information representing noise levels directly to data center computing devices 106. In some examples, sound level monitor 116 may send the information representing noise levels to portable computing device 114B, and device 114B may send the information to one or more of computing devices 104 and/or 106. In some examples, portable computing devices 114 and/or sound level monitor 116 may detect location information within the worksite, such that information representing noise levels is accompanied by location information.

When a worker, such as worker 112B, exits worksite 110, portable computing device 114B or a reader, beacon, or other identifying device may send a set of data to worksite computing device 104 or data center computing devices 106 that indicates worker 112A is exiting worksite 110. The set of data may include, but is not limited to, a worksite identifier, a timestamp, a unique worker identifier, information representing noise levels, and location information corresponding to noise levels. As such, application 228 may have access to such information when performing techniques of this disclosure.

As shown in FIG. 1A, application 228 may perform one or more techniques of this disclosure. For instance, application 228 may recommend one or more types of hearing protection devices based on at least one or more of: worksite noise data, results or personal attenuation ratings for individual or groups of workers, and/or noise-reduction ratings for various different types of hearing protection. As an example, a user may operate computing device 108 to access a user interface provided by application 228. The user may provide a user input to the user interface that specifies a worksite. The user may also provide a user input to the user interface that specifies an identity of a worker. Application 228 may determine noise level information for the specified worksite and noise levels measured by the fit-testing system for various types of hearing protection devices for the particular user. Application 228 may determine, for one or more of the respective types of hearing protection devices, whether the noise level information for the specified worksite exceeds a protection maximum measured by the fit testing system for a particular model of hearing protection as worn by the worker, the personal attenuation rating, or noise reduction data measured by the fit-testing system for a particular type of hearing protection device. In some examples, application 228 may, based on such determinations, recommend one or more options of types of hearing protection devices for which the noise level of the specified worksite does not exceed the attenuation capabilities of the types of specified hearing protection devices or protection maximum measured by the fit testing system for a particular type of hearing protection as worn by the worker. In some examples, a different type of hearing protection may be a different model, sound attenuation rating, or any other distinguishing characteristic between two different types of hearing protection.

In some examples, portable computing devices 114 and/or sound level monitor 116 may detect and store information about user interactions with portable computing devices 114 and/or sound level monitor 116. Such interactions may include determining which features of portable computing devices 114 and/or sound level monitor 116 are or are not selected by the worker, how often the features are or are not selected, at what times or in what environments the features are or are not selected by the worker, or any other interactions performed or not performed by the worker with respect to functionality of portable computing devices 114 and/or sound level monitor 116. Portable computing devices 114 and/or sound level monitor 116 may send data indicating such interactions to worksite computing device 104 (which sends the data to data center computing devices 106) or directly to data center computing devices 106.

Application 228 may generate statistics of which features of portable computing devices 114 and/or sound level monitor 116 are or are not selected by the worker, how often the features are or are not selected, at what times or in what environments the features are or are not selected by the worker, or any other interactions performed or not performed by the worker with respect to functionality of portable computing devices 114 and/or sound level monitor 116. Based on these statistics, application 228 may generate one or more ordered lists, sets, or selections of features and/or functionality for portable computing devices 114 and/or sound level monitor 116 that are used by the worker. As an example, application 228 may create a list of functions provided by sound level monitor 116, which are ordered by how often a set of one or more workers selects or otherwise uses the particular function. Application 228 may output the ordered list for display in a user interface at computing device 108, such that a user may identify the frequency with which the functions of sound level monitor 116 are used by workers. In some examples, application 228 may automatically send one or more alerts to one or more users who are registered with application 228 when one or more of the generated statistics satisfy a threshold (e.g., are greater than or equal to, or are less than or equal to the threshold). Such users may include supervisors of worksites, safety managers of worksites, or management individuals who are responsible for worksites. An alert may be a text message, email, phone call or any other suitable notification. Such feature tracking may enable such users to determine whether various features and/or functionality of equipment are or are not being used by workers, in the event that such features and/or functionality are not operating correctly or are not useful or desirable to the worker.

In some examples, application 228 may identify Standard Threshold Shifts (STSs), which may be a change in a hearing threshold for an individual relative to a baseline audiogram. As such application 228 may correlate STSs on particular workers to the fact that the worker worked in a particular area having a particular noise level. In such examples, it may be inferred that that noise level may have caused the STS. In some examples, application 228 may output for display a user interface 120 that includes a visualization 122 of changes noise levels over a historical time frame. In some examples, visualization 122 may highlight or otherwise signify a noise level that satisfies a threshold with one or more indicators and/or format changes in color, size, location or any other visual property. For instance, graphical indicator 124 indicates a change in noise level above a threshold, which is illustrated in visualization 122. If application 228 identifies a change in a noise level for an individual that satisfies a threshold (e.g., are greater than or equal to, or are less than or equal to the threshold), application 228 may send an alert to one or more registered users of application 228. In some examples, the alert may specify one or more of a worker identifier, worksite identifier, noise level information, date and/or time of change in noise level that satisfies the threshold, location within the worksite corresponding to date and/or time of change in noise level that satisfies the threshold, hearing protection device identifier, or any other information relating to the change in noise level. In some examples, application 228 may identify a noise source (e.g., a machine, loading/unloading area, or any other source that generates noise) based on data indicating a location within the worksite that corresponds to a date and/or time of change in noise level that satisfies a threshold. For instance, application 228 may access location data within data center computing devices 106 that indicate locations of noise sources within worksites.

In response to detecting a change in noise level for a particular worker, application 228 may identify any noise sources that are within a threshold distance from the location of the particular worker. For instance application 228 may determine the location of the particular worker at the time of the detected change in noise level, and may identify the locations of any noise sources that are within a threshold distance of the location of the particular worker. Upon detecting one or more noise sources, application 228 may send one or more alerts to one or more registered users. The one or more alerts may indicate, but are not limited to, the location of the particular worker at the time of the detected change in noise level, locations of any noise sources that are within a threshold distance of the location of the particular worker, the level of noise, the change in the level of noise, and/or identifying information of the noise source (e.g., a name or identifier of a machine, a loading area, etc.).

In some examples, a type of noise source may also be associated with the location and/or name of the noise source in data center computing devices 106. Application 228 may provide a recommendation in the alert based on the type of noise source. The recommendation may be based on a rule stored by application 228, where the rule comprises a condition and an action. Application 228 may execute the action when the condition is satisfied. For instance, application 228 may determine that if the condition for the type of noise source is 'machine', the action may include sending an alert with a recommendation to perform maintenance on the noise source (i.e., the machine). Application 228 may include such a rule because a machine that requires maintenance or has experienced an unexpected problem may emit a noise at a louder level than normal operation. In another example, a recommendation may be based on a rule, where the condition for the rule determines whether the current amount of noise reduction provided by the level of hearing protection devices for a worker experiencing the change in a noise level satisfies a threshold. The action for this rule may include determining one or more types of hearing protection devices that provide greater noise reduction and sending a recommendation to the worker and/or one or more registered users to use the one or more types of hearing protection devices. In this way, application 228 may proactively notify the worker and/or one or more registered users to reduce or prevent noise-induced hearing loss of the worker. If application 228 determines that the worker is not presently wearing hearing protection (e.g., based on detecting the worker at the worksite, detecting that the user was not previously fit-tested or assigned hearing protection, and/or a portable computing device attached or proximate to the user indicates that the user is not wearing hearing protection), then application 228 may send an alert to the worker and/or one or more other users with a recommendation that the user wear hearing protection that provides adequate noise reduction for the noise level. In some examples, application 228 may determine that the worker is wearing multiple different types of PPE. If a first type of PPE resulted in the generation of an alert (e.g., worker not wearing hearing protection), application 228 may send the notification to a second, different type of article of PPE (e.g., purified air powered respirator head top) worn by the worker that is also wearing the PPE that resulted in the generation of the alert.

In some examples, application 228 may identify a worker location and duration patterns in worksites with noisy areas to determine if workers need hearing protection. If the workers already wear protection, application 228 may determine whether the hearing protection is adequate for the duration. For instance, application 228 may access predefined duration data that specifies a maximum duration that a worker may be exposed to a particular noise level. If the worker exceeds the maximum duration at the particular noise level for the particular hearing protection device used, the worker may be at risk for hearing damage or loss. Application 228 may, based on worksite data sent from worksite computing device 104 and/or devices of the workers themselves, determine how long a worker has been exposed to various noise levels. If a worker operates with inner earplugs at a worksite at a particular noise level for a particular duration, application 228 may monitor the duration, noise level, and type of hearing protection worn by the user, and determine whether the amount of noise over the duration exceeds a threshold, and if so, provide an alert. As one example scenario, a worker may work at a first worksite for eight hours with a particular type of hearing protection device that is rated for the worksite noise level for eight hours per day. If the worker later begins work in the same day at a second worksite with similar or higher noise levels, application 228 may determine that the worker has exceeded the threshold amount of noise for the hearing protection device in a single day. Accordingly, application 228 may send an alert to the worker and/or one or more other users that specifies a different or supplemental form of hearing protection.

In some examples, application 228 may identify outliers or anomalies via abnormal pattern analysis. One worker from a group with similar work roles and similar areas may have an STS that is abnormal when compared to rest of the group and hence causes of the STS might be non-work/occupation related. Application 228 may, for example, determine a set of workers that have worked together within a threshold distance of one another over a time duration. As described above, application 228 may also include fit-testing data that indicates noise reduction or protected exposures measured for particular workers wearing particular hearing protection. Based on the fit-testing data, application 228 may determine that a subset of one or more workers in an overall set of workers working within a threshold distance of one another are experiencing an STS that is abnormal when compared with fit-testing data for other workers. An STS may satisfy a threshold (e.g., are greater than or equal to, or are less than or equal to the threshold). In response to detecting an STS, application 228 may send an alert to each worker in the overall set of workers and/or one or more other users of application 228. In this way, the alerted workers and/or other users may further investigate the cause for the STS in only a subset of the overall set of workers that worked within a threshold distance of one another.

In some examples, one or more types of hearing protection may include one or more sensors and/or computing devices, which provide for detection of whether a worker is wearing hearing protection. For instance, the hearing protection may include a touch sensor or tension sensor that indicates whether the hearing protection is currently being worn by the worker. In some examples, the hearing protection may include one or more smart tags or RFID sensors to provide for location triangulation, such that a set of remote readers may determine whether the hearing protection is in use on the worker's head. Other techniques are also possible for determining whether hearing protection is in use on the worker's head. In any case, data indicating whether hearing protection is in use on the worker's head may be sent to data center computing devices 106 directly or via worksite computing device 104, personal computing devices 114, or the hearing protection equipment itself. Based on determining whether hearing protection is in use on the worker's head, application 228 may determine wear time durations of when and/or how long the work is wearing the particular hearing protection device. Application 228 may correlate the wear time data with STSs identify whether an STS is the result of a worker not using hearing protection correctly in specified areas where noise levels require hearing protection.

FIG. 1B illustrates a data hub as shown in FIG. 1A, in accordance with techniques of this disclosure. FIG. 1B illustrates components of data hub 114A including processor 130, communication unit 132, storage device 134, user-interface device 136, PPE component 138, notification component 140, and PPE data 142. FIG. 1B illustrates only one particular example of data hub 114A. Many other examples of data hub 114A may be used in other instances and may include a subset of the components included in example data hub 114A or may include additional components not shown example data hub 114A in FIG. 1B. In some examples, data hub 114A may be an intrinsically safe computing device, smartphone, wrist- or head-worn computing device, or any other computing device that may include a set, subset, or superset of functionality or components as shown in data hub 114A. Communication channels may interconnect each of the components in data hub 114A for inter-component communications (physically, communicatively, and/or operatively). In some examples, communication channels may include a hardware bus, a network connection, one or more inter-process communication data structures, or any other components for communicating data between hardware and/or software.

One or more processors 130 may implement functionality and/or execute instructions within data hub 114A. For example, processor 130 may receive and execute instructions stored by storage devices 404. These instructions executed by processor 130 may cause data hub 114A to store and/or modify information, within storage devices 134 during program execution. Processors 130 may execute instructions of components, such as PPE component 138 and notification component 140 to perform one or more operations in accordance with techniques of this disclosure. That is, PPE component 138 and notification component 140 may be operable by processor 130 to perform various functions described herein.

Data hub 114A may include one or more user-interface devices 136 to receive user input and/or output information to a user. One or more input components of user-interface devices 136 may receive input. Examples of input are tactile, audio, kinetic, and optical input, to name only a few examples. User-interface devices 136 of data hub 114A, in one example, include a voice responsive system, video camera, buttons, control pad, microphone or any other type of device for detecting input from a human or machine. In some examples, UI device 136 may be a presence-sensitive input component, which may include a presence-sensitive screen, touch-sensitive screen, etc.

One or more output components of user-interface devices 136 may generate output. Examples of output are tactile, audio, and video output. Output components of user-interface devices 408, in some examples, include a presence-sensitive screen, sound card, video graphics adapter card, speaker, cathode ray tube (CRT) monitor, liquid crystal display (LCD), or any other type of device for generating output to a human or machine. Output components may include display components such as cathode ray tube (CRT) monitor, liquid crystal display (LCD), Light-Emitting Diode (LED) or any other type of device for generating tactile, audio, and/or visual output. Output components may be integrated with data hub 114A in some examples.

UI device 136 may include a display, lights, buttons, keys (such as arrow or other indicator keys), and may be able to provide alerts to the user in a variety of ways, such as by sounding an alarm or vibrating. The user interface can be used for a variety of functions. For example, a user may be able to acknowledge or snooze an alert through the user interface. The user interface may also be used to control settings for the head top and/or purified air powered respirator peripherals that are not immediately within the reach of the user. For example, a purified air powered respirator may be worn on the lower back where the wearer cannot access the controls without significant difficulty.

One or more communication units 132 of data hub 114A may communicate with external devices by transmitting and/or receiving data. For example, data hub 114A may use communication units 132 to transmit and/or receive radio signals on a radio network such as a cellular radio network. In some examples, communication units 132 may transmit and/or receive satellite signals on a satellite network such as a Global Positioning System (GPS) network. Examples of communication units 132 include a network interface card (e.g. such as an Ethernet card), an optical transceiver, a radio frequency transceiver, a GPS receiver, or any other type of device that can send and/or receive information. Other examples of communication units 132 may include Bluetooth®, GPS, 3G, 4G, and Wi-Fi® radios found in mobile devices as well as Universal Serial Bus (USB) controllers and the like.

One or more storage devices 134 within data hub 114A may store information for processing during operation of data hub 114A. In some examples, storage device 134 is a temporary memory, meaning that a primary purpose of storage device 134 is not long-term storage. Storage device 134 may configured for short-term storage of information as volatile memory and therefore not retain stored contents if deactivated. Examples of volatile memories include random access memories (RAM), dynamic random access memories (DRAM), static random access memories (SRAM), and other forms of volatile memories known in the art.

Storage device 134, in some examples, also include one or more computer-readable storage media. Storage device 134 may be configured to store larger amounts of information than volatile memory. Storage device 134 may further be configured for long-term storage of information as non-volatile memory space and retain information after activate/off cycles. Examples of non-volatile memories include magnetic hard discs, optical discs, floppy discs, flash memories, or forms of electrically programmable memories (EPROM) or electrically erasable and programmable (EEPROM) memories. Storage device 134 may store program instructions and/or data associated with components such as PPE component 138 and notification component 140.

Data hub 114A may also include a power source, such as a battery, to provide power to components shown in data hub 114A. A rechargeable battery, such as a Lithium Ion battery, can provide a compact and long-life source of power. Data hub 114A may be adapted to have electrical contacts exposed or accessible from the exterior of the hub to allow recharging the data hub 114A.

FIG. 1B illustrates PPE data 142 included in data hub 114A. PPE data 142 may include a list, set, or other structure data identifying each article of PPE that is communicatively coupled to data hub 114A. In some examples, PPE data may be unique device identifiers for each of PPE data 142. In some examples, PPE data 142 may also include operating data about or received from one or more articles of PPE in communication and/or proximity with PPE data 142. For instance, PPE data may indicate one or more metrics describing the operation or use of one or more of a powered air purifying respirator, fall protection equipment, hearing protector, protective garment, head/eye/face protection, or any other PPE.

In some examples, PPE component 138 may send and receive data between one or more articles of PPE, beacons, worksite computing devices, data centers or any other computing devices. In some examples, PPE component 138 may log data received from beacons, worksite computing devices, and one or more articles of PPE. PPE component 138 may send configuration data to articles of PPE, where the data was received from beacons, worksite computing devices, data centers or other remote computing devices. In this way, the operation of the articles of PPE may be changed based on data received by PPE component 138.

In some examples, PPE component 138 may cause UI device 136 to output a graphical user interface for display. The graphical user interface may include one or more input controls, graphics or any other visual components that display any data or information described in this disclosure. For instance, the graphical user interface may indicate a sound level to which the worker is exposed and/or whether the sound level exceeds a threshold. In some examples, the sound level may be with respect to a particular location within a work environment and/or a particular time that the sound level was detected in the work environment. In other examples, the graphical user interface may include visual components that indicate alerts, work environment hazards, operating data of personal protective equipment, or any other data relating to the worker, PPE or work environment.

Notification component 140 may generate one or more notification or alerts at data hub 114A and/or one or more articles of PPE. Example notifications may include visual, audio, or haptic alerts. As an example, notification component 140 may cause data hub 114A to generate a notification in response to receiving notification data from beacons, worksite computing devices, data centers or other remote computing devices.

Although various operations are described in this disclosure as being performed at particular computing devices, such as data hub 114A and application 228 (and other computing devices, such as worksite computing devices), any of the operations described in this disclosure may be performed at any of the computing devices. For instance, one or more sets of functionality described as being performed by application 228 may be performed at data hub 114A. Similarly, one or more sets of functionality described as being performed at data hub 114A may be performed at application 228. Such distribution, split, or allocation of functionality across any number of computing devices is possible, including personal protective equipment itself.

Figure 2:
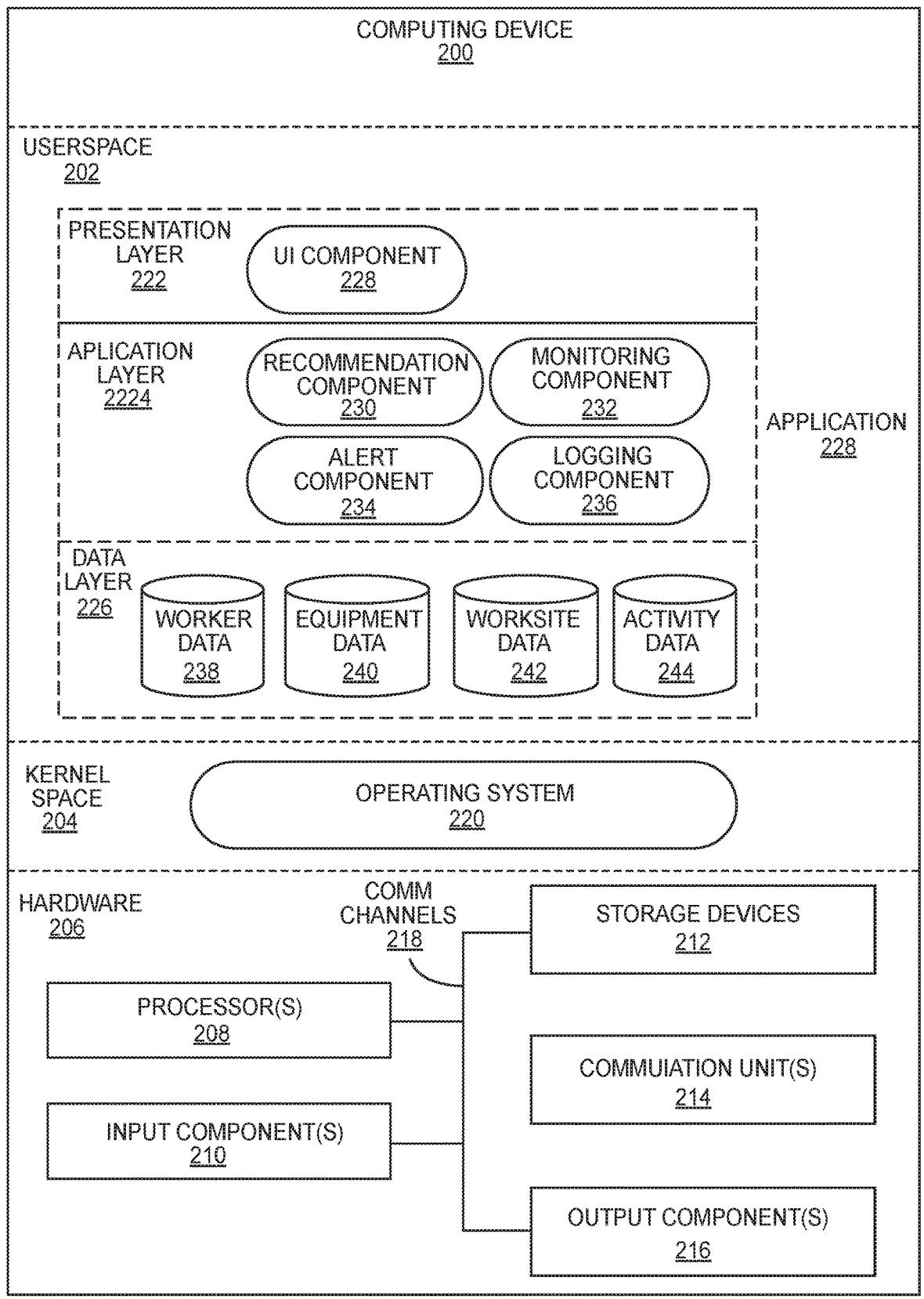
FIG. 2 is a block diagram illustrating an example computing device, in accordance with one or more aspects of the present disclosure.

FIG. 2 is a block diagram illustrating an example computing device, in accordance with one or more aspects of the present disclosure. FIG. 2 illustrates only one particular example of computing device 200. Many other examples of computing device 200 may be used in other instances and may include a subset of the components included in example computing device 200 or may include additional components not shown example computing device 200 in FIG. 2. In some examples, computing device 200 may be one of computing devices 106A-106C of FIG. 1A. In some examples, computing device 200 may be a tablet computing device, smartphone, wrist- or head-worn computing device, laptop, desktop computing device, or any other computing device that may run a set, subset, or superset of functionality included in application 228.

As shown in the example of FIG. 2, computing device 200 may be logically divided into user space 202, kernel space 204, and hardware 206. Hardware 206 may include one or more hardware components that provide an operating environment for components executing in user space 202 and kernel space 204. User space 202 and kernel space 204 may represent different sections or segmentations of memory, where kernel space 204 provides higher privileges to processes and threads than user space 202. For instance, kernel space 204 may include operating system 220, which operates with higher privileges than components executing in user space 202.

As shown in FIG. 2, hardware 206 includes one or more processors 208, input components 210, storage devices 212, communication units 214, and output components 216. Processors 208, input components 210, storage devices 212, communication units 214, and output components 216 may each be interconnected by one or more communication channels 218. Communication channels 218 may interconnect each of the components 208, 210, 212, 214, and 216 for inter-component communications (physically, communicatively, and/or operatively). In some examples, communication channels 218 may include a system bus, a network connection, one or more inter-process communication data structures, or any other components for communicating data between hardware and/or software.

One or more processors 208 may implement functionality and/or execute instructions within computing device 200. For example, processors 208 on computing device 200 may receive and execute instructions stored by storage devices 212 that provide the functionality of components included in kernel space 204 and user space 202. These instructions executed by processors 208 may cause computing device 200 to store and/or modify information, within storage devices 212 during program execution. Processors 208 may execute instructions of components in kernel space 204 and user space 202 to perform one or more operations in accordance with techniques of this disclosure. That is, components included in user space 202 and kernel space 204 may be operable by processors 208 to perform various functions described herein.

One or more input components 242 of computing device 200 may receive input. Examples of input are tactile, audio, kinetic, and optical input, to name only a few examples. Input components 242 of computing device 200, in one example, include a mouse, keyboard, voice responsive system, video camera, buttons, control pad, microphone or any other type of device for detecting input from a human or machine. In some examples, input component 242 may be a presence-sensitive input component, which may include a presence-sensitive screen, touch-sensitive screen, etc.

One or more output components 216 of computing device 200 may generate output. Examples of output are tactile, audio, and visual output. Output components 216 of computing device 200, in some examples, include a presence-sensitive screen, sound card, video graphics adapter card, speaker, cathode ray tube (CRT) monitor, liquid crystal display (LCD), or any other type of device for generating output to a human or machine. Output components may include display components such as cathode ray tube (CRT) monitor, liquid crystal display (LCD), Light-Emitting Diode (LED) or any other type of device for generating tactile, audio, and/or visual output. Output components 216 may be integrated with computing device 200 in some examples. In other examples, output components 216 may be physically external to and separate from computing device 200, but may be operably coupled to computing device 200 via wired or wireless communication. An output component may be a built-in component of computing device 200 located within and physically connected to the external packaging of computing device 200 (e.g., a screen on a mobile phone). In another example, presence-sensitive display 202 may be an external component of computing device 200 located outside and physically separated from the packaging of computing device 200 (e.g., a monitor, a projector, etc. that shares a wired and/or wireless data path with a tablet computer).

One or more communication units 214 of computing device 200 may communicate with external devices by transmitting and/or receiving data. For example, computing device 200 may use communication units 214 to transmit and/or receive radio signals on a radio network such as a cellular radio network. In some examples, communication units 214 may transmit and/or receive satellite signals on a satellite network such as a Global Positioning System (GPS) network. Examples of communication units 214 include a network interface card (e.g. such as an Ethernet card), an optical transceiver, a radio frequency transceiver, a GPS receiver, or any other type of device that can send and/or receive information. Other examples of communication units 214 may include Bluetooth®, GPS, 3G, 4G, and Wi-Fi® radios found in mobile devices as well as Universal Serial Bus (USB) controllers and the like.

One or more storage devices 212 within computing device 200 may store information for processing during operation of computing device 200. In some examples, storage device 212 is a temporary memory, meaning that a primary purpose of storage device 212 is not long-term storage. Storage devices 212 on computing device 200 may configured for short-term storage of information as volatile memory and therefore not retain stored contents if deactivated. Examples of volatile memories include random access memories (RAM), dynamic random access memories (DRAM), static random access memories (SRAM), and other forms of volatile memories known in the art.

Storage devices 212, in some examples, also include one or more computer-readable storage media. Storage devices 212 may be configured to store larger amounts of information than volatile memory. Storage devices 212 may further be configured for long-term storage of information as non-volatile memory space and retain information after activate/off cycles. Examples of non-volatile memories include magnetic hard discs, optical discs, floppy discs, flash memories, or forms of electrically programmable memories (EPROM) or electrically erasable and programmable (EEPROM) memories. Storage devices 212 may store program instructions and/or data associated with components included in user space 202 and/or kernel space 204.

As shown in FIG. 2, application 228 executes in userspace 202 of computing device 200. Application 228 may be logically divided into presentation layer 222, application layer 224, and data layer 226. Presentation layer 222 may include user interface (UI) component 228, which generates and renders user interfaces of application 228, such as user interfaces illustrated in FIGS. 3-20. Application layer 224 may include recommendation component 230, monitoring component 232, alert component 234, and logging component 236. Logging component 236 may receive various data from worksite computing devices (e.g., worksite computing device 104 of FIG. 1A), portable computing devices 114, and/or any other computing devices. Logging component 236 may store the data in one or more datastores comprising data, such as but not limited to: worker data 238, equipment data 240, worksite data 242, activity data 244, and/or any other data. Datastores for worker data 238, equipment data 240, worksite data 242, activity data 244 may be any one or more of a relational database management system, online analytical processing database, table, or any other suitable structure for storing data. Logging component 236 may generate and/or store metadata such as timestamp information, sender information, priority information, or any other information describing the data received by logging component 236.

Worker data 238 may include worker identification information, such as but not limited to: name, address, age, worker designation, company, fit-testing data, or any other data relating to a worker. In some examples, worker data 238 may include biometric information about workers including but not limited to: body temperature, heart rate, or any other biometric measure. Equipment data 240 may include equipment identification information, such as but not limited to: unique equipment identifier, equipment specifications, noise ratings, or any other data relating to a piece of equipment. Worksite data 242 may include worksite information, such as but not limited to: unique worksite identifier, worksite location, worksite working conditions (e.g., hazards, noise levels, climate, to name only a few examples). Activity data 244 may include activity information indicating a particular instance of worksite, worker, and equipment data. For instance, a particular worker, using a particular piece of equipment in a particular worksite. Logging component 236 may store activity information as application 228 receives data from worksite computing devices (e.g., worksite computing device 104 of FIG. 1A), portable computing devices 114, and/or any other computing devices.

Monitoring component 232 may perform various analytical and monitoring techniques as described in this disclosure. For instance, monitoring component 232 may monitor for outliers or other abnormal patterns in activity data 244 or any other data in data layer 226. In some examples, monitoring component 232 may determine whether a threshold has been satisfied when performing any of the techniques described in this disclosure. Recommendation component 230 of FIG. 2 may provide a recommendation in an alert, notification or via a user interface, to name only a few examples. The recommendation generated by recommendation component 230 may be based on a rule stored by application 228, where the rule comprises a condition and an action. Recommendation component 230 may execute the action when the condition is satisfied. Alert component 234 may generate and send alerts via any number of modes of communication. For instance, alert component 234 may generate and send one or more emails, phone calls, text messages, user interface notifications, or any other type of alert.

FIGS. 3-20 illustrate various user interfaces that may be generated for output and display by application 228. Each of the user interfaces shown FIGS. 3-20 may be generated based on data from data layer 226, including information received through communication unit 214 from other devices, such as portable computing devices 114A and 114B, environmental sensors 118A and 118B and other devices interacting with the intelligent safety system 100, such as a smart tag or other electronic or communication devices. Such data and information can be monitored, analyzed and displayed in a variety of ways, as discussed herein. Further, the user interfaces shown in FIGS. 3-20 may provide additional content for a user, including for example, information such as comparative data, historic data, training information, graphical information, and other information as may be useful to a user or manager of safety system 100. While FIGS. 3-20 display specific types of information, analysis, data, graphs, etc., they are only examples of user interfaces in a safety system consistent with the present disclosure. Other types of outputs for display in a user interface consistent with the present disclosure will be apparent to one of skill in the art upon reading the present disclosure.

As described in FIG. 1, in some instances, a worker may work longer than a standard, defined period of time (e.g., eight-hour workday), and as such, may be exposed to amounts of sound that exceed the maximum dosage for the defined period of time and/or for a particular type of hearing protection over the defined period of time. In some examples, monitoring component 232 may receive and store in worker data 238 first sound exposure data that indicates a first amount of sound that the worker was exposed to over a first period of time for a particular day in a first area of a work environment. Monitoring component 232 may receive such data from a portable computing device associated with the worker, a sound level monitor, dosimeter, or other computing device in the work environment.

At a later time, after the worker has moved to a second area of a work environment in the particular day, monitoring component 232 may receive second sound exposure data that indicates a second amount of noise that the worker has been exposed to over a second period of time for the particular day in the second area. In some instances, monitoring component 232 may store in worker data 238, the data indicating the first amount of sound that the worker was exposed to over the first period of time for the particular day in the first area of the work environment. Monitoring component 232 may determine, based on the first and second sound exposure data, that a cumulative amount of sound that the worker has been exposed to over the first and second periods of time exceeds a threshold or noise exposure limits for the particular day. In some examples, monitoring component 232 may cause alert component 234 to generate a notification for the portable computing device assigned to the worker that indicates the cumulative amount of sound that the worker has been exposed to over the first and second periods of time exceeds a threshold for the particular day. Although a day was used as a defined time duration in the aforementioned example, any time duration may be used including, but not limited to: minutes, hours, days, weeks, months or the like. In general, a defined time duration or any other time period described in this disclosure may be hard-coded by the provider of application 228, user-defined by input provided by a user to application 228, or machine generated by application 228.

In some examples, the threshold for the particular day is less than a maximum amount of allowable sound exposure for the defined time duration (e.g., day), so as to alert the worker to exit the work environment prior to exceeding the maximum allowable sound exposure. In some examples, monitoring component 232 receives the sound level data that indicates different sound levels at different, respective locations of a work environment from one or more portable sound level monitors worn by workers in the work environment. In some examples, monitoring component 232 may determine that the cumulative amount of sound exceeds the threshold based at least in part on an amount of sound attenuation provided by the article of hearing protection assigned to a worker. In some examples, the first sound level in the first area is different than the second sound level in the second area of the work environment. In some examples, the particular day is a defined time duration stored computing device 200, and a cumulative amount of time based on the first and second periods of time is greater than the defined time duration (e.g., day).

In some examples, monitoring component 232 may generate a risk score based on one or more parameters, such as but not limited to: worker exposure to hazards in the work environment, worker use of personal protective equipment, work time spent in work environment, or any other parameter that indicates risk to the user. If, for example, application 228 determines that a worker is within a threshold distance of a hazard and is not properly using/wearing certain personal protective equipment, application 228 may increase the risk score. Conversely, as a worker remains compliant with use of personal protective equipment while in a work environment and/or with respect to hazards located in the work environment, application 228 may decrease or hold the risk score constant. If a risk score exceeds a threshold, application 228 may send alerts to one or more of the worker and/or other users. As another example, application 228 may generate for display a risk score for a worker or work group that is based on a noise hazard to which the worker or work group was exposed (e.g., "Worker A exposed to high noise hazard, measured risk score 78%.") In some examples, application 228 may automatically send alerts that indicate required or recommended training for the worker based on the work environment, hazards, behavior of worker, and/or PPE used by the worker. In some examples, application 228 may determine if a worker's score is an anomaly or outlier with respect to other workers in the same population that work in the same work environment. In response to detecting such an anomaly, application 228 may generate an alert for the worker and/or one or more other users of application 228.

In some examples, recommendation component 230 may recommend additional or different hearing protection if the sound level in the second area is different than the first area. For instance, in response to determining that the worker has moved to the second area of the work environment in the particular day, recommendation component 230 may determine that a sound level in the second area is greater than a sound level in the first area. Recommendation component 230 may identify, based at least in part on the determination that the sound level in the second area is greater than the sound level in the first area a second article of hearing protection that attenuates sound more than the first article of hearing protection. The second article of hearing protection may be of a different type than the first article of hearing protection. For instance, the degree to which the second article of hearing protection attenuates or reduces sound may be greater than the first article of hearing protection. Recommendation component 230 may generate for output an indication of the second article of hearing protection. For instance, recommendation component 230 may cause alert component 234 and/or UI component 228 to output one or more visual, audio, or haptic alerts that indicate the second article of hearing protection is recommended for the sound level in the second environment, and in some examples, further based on the previous amount of sound exposure to the work in the first area of the work environment. The aforementioned techniques, although described with respect to two areas may be applied to any number of different areas that a worker may operate within during a defined time duration.

In some examples, a dosimeter may not accurately measure certain types of sound, such as impulses greater than or equal to a threshold value. In some examples, the threshold value may be 180 dBP SPL, 160 dBP SPL, 140 dBP SPL, or any other value. In any case, application 228 may be separately configured by user input to indicate the sound levels in such environments. For instance, in a firing range, dosimeters and conventional level meters may not accurately capture sound level data. As such, application 228 may generate a user interface for display in which a user can enter one or more values that represent sound levels or other sound data for the environment in which dosimeters and conventional level meters may not accurately capture sound level data. Application 228 may then use such values that represent sound levels or other sound data to determine the level of dosing a user or worker may be exposed to in the environment (e.g., based on determined location of user/worker), and provide alerts, logging, or automatic changes to the operation of PPE while operating in the environment. For instance, in some examples, application 228 may send a message to a variable sound attenuating hearing protector that causes the attenuation level of the protection device to change. If, for example, the sound level of an environment increases, application 228 may send one or more messages the variable sound attenuating hearing protector that increases the attenuation level, and conversely for decreases in sound levels in an environment, the attenuation level may decrease for variable sound attenuating hearing protector.

In some examples, application 228 may monitor workers not wearing PPE based on the such workers being detected (e.g., by a data hub worn by the worker, camera capturing worker in an image, or any other suitable technique for detecting a worker) by application 228. For instance, if a worker without PPE is operating an environment where due to sound level dosing the worker does not initially require hearing protection but after exposure for a period of time the worker does require hearing protection, application 228 may alert the worker requiring hearing protection and/or one or more other workers and/or users of application 228.

Figure 3B:
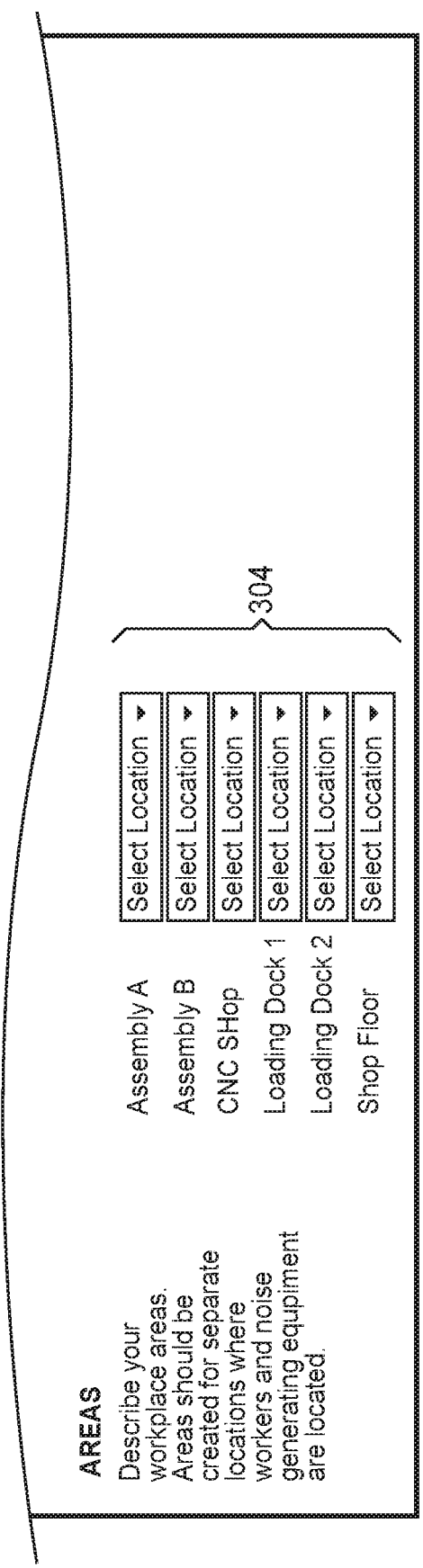

FIGS. 3A-3B illustrate a user interface 300 that may be generated and output for display by application 228, in accordance with one or more techniques of this disclosure. In particular, user interface 300 receives input information from a user corresponding to program goals for a safety program, such as a hearing conservation program. As shown in FIG. 3A, user interface 300 includes a set of one or more input controls (e.g., text boxes, dropdown menus, submit buttons, or any other controls for selecting, providing, and/or submitting input values). For instance, user interface 300 includes input controls 302, which allow a user to input a company name, program goals, country, regulatory body, and company exposure limit for the hearing conservation program. The exposure limit may include a maximum threshold of noise exposure (e.g., on a particular time interval) or time-weighted average (TWA) to which a worker may be exposed. Application 228 may use the configured threshold to determine whether noise exposure has exceeded the exposure limit and alert the worker and/or other users. User interface 300 may also include input controls 304 which allow a user to specify individuals in various roles for the safety program, such as program administrator, professional supervisor, audiometric technician, noise survey technician, and shop floor. Input controls 304 enable an administrator to provide user input that includes an authorization level (e.g., security level) associated with a particular user role (e.g., professional supervisor). In some examples, one or more individual users may be assigned to a role and therefore the one or more users may have the authorization level or permissions to administrate application 228 in accordance with techniques of this disclosure. FIG. 3B includes input controls 306 to associate different worksites with particular locations. For instance, the CNC shop may be associated with location data, where the location data may be geoposition data, relative location data (e.g., based on a beacon location), build data, or any other data indicating location. As described in this disclosure, application 228 may use location information for different worksites to proactively notify workers/users, provide recommendations, or perform other operations in view of hazards or data associated with the location information.

As described in FIGS. 1A-1B, safety system 100 may determine whether a particular article of machinery requires an inspection or maintenance based on sound levels that deviate from a baseline or normal level of sound during normal operation. For instance, an article of machinery may be any equipment in a work environment that emits sound. Examples of machinery may include mixers, packagers, fans, conveyors, ovens, machine tools, or any other suitable equipment used in a work environment. Worksite data 242 may include data describing articles of machinery, such as but not limited to: article identifier, article name, article operating parameters, article use time, article status, and article baseline sound data. Such data describing articles of machinery may be entered via a graphical user interface by a user or may be machine generated. Worksite data 242 may include baseline sound data that indicates a baseline sound level generated by the article of machinery while in operation. The baseline sound data may indicate a sound level generated by the machine when in normal operation (e.g., no errors, exceptions, or problems with the operation of the machine).

Monitoring component 232 may receive from a sound level monitor assigned to a worker, sound data that corresponds to a location of the article of machinery. Monitoring component 232 may determine that baseline sound data for the article of machinery included in worksite data 242 is exceeded by the sound data that corresponds to a location of the article of machinery. That is, recommendation component may compare the location (or machine identifier) associated with the sound data from the sound level monitor to the location (or machine identifier) included in worksite data 242. In this way, recommendation component 230 can select baseline sound data that correspond to the article of machinery. Monitoring component 230 may cause alert component 234 to generate a notification that the sound data that corresponds to a location of the article of machinery exceeds the baseline sound data by a threshold amount. In some examples, the notification may be output for display by UI component 228. In other examples, the notification may be sent by computing device 220 to one or more of a worker within a threshold distance of the article of machinery or one or more other persons in the work environment and/or responsible for the article of machinery and/or the safety of workers in the work environment.

In some examples, the notification indicates that the article of machinery requires at least one of an inspection or maintenance. The notification may include an identifier of the article of machinery and/or a location of the article of machinery. In some examples, alert component 234 may send, in response to a determination that the baseline sound data is exceeded by the sound data that corresponds to the location of the article of machinery, a message to the article of machinery that causes the operation of the machinery to change. For instance, the message may cause the article of machinery to stop, lower its operating rate or intensity, or output one or more alerts or other indications at the article of machinery.

In some examples, the baseline sound data is based on at least one of (i) sound data from one or more sound level monitors assigned to one or more workers or (ii) sound data from a set of one or more other articles of machinery in different work environments, the one or more other articles of machinery being of the same type as the article of machinery. In some examples, the baseline sound data indicates a first sound level and the sound data that corresponds to the location of the article of machinery represents a second sound level. In some examples, the threshold amount by which the sound data that corresponds to a location of the article of machinery exceeds the baseline sound data may be greater than zero.

FIG. 4 illustrates a user interface 400 that may be generated and output for display by application 228, in accordance with one or more techniques of this disclosure. User interface 400 includes one or more input controls to set up additional options in accordance with one or more techniques of this disclosure. For instance, section 402 allows a user to create and manage groups of workers. By configuring groups of workers, application 228 may perform comparisons, alerting, or other processing of hazards or data associated with a common location and/or time period. Workers may be configured into groups based on shifts, locations in which they are working, or any other useful grouping technique. In section 404, a user can assign a particular worker to both location(s) and worker group(s). For example, as illustrated, worker B, Able, is configured in the CNC Shop area and is configured in the Shift A worker group. Section 406 shows input controls that allow a user to enter and manage types of PPE used by one or more companies. Types of PPE entered into section 406 via user input may be specifically related to hearing as shown, or may be any other type of PPE as discussed throughout the present disclosure or as known in the industry.

In some examples, a subset of workers, each assigned to a work group (e.g., "welders") in application 228 may don a sound level monitor or dosimeter, while the remaining workers also assigned to the work group may not don a sound level monitor or dosimeter. When all of the workers are operating in the particular work environment, application 228 may determine that workers not donning a sound level monitor or dosimeter are exposed to the same hazards (e.g., noise) as other workers in proximity or within a threshold distance of such workers not donning a sound level monitor or dosimeter. In this way, application 228 may determine from locations of the various workers, the level of sound exposure for each worker, although not all workers are wearing a sound level monitor or dosimeter. In this way, application 228 may measure sound measurements from one worker and apply them as proxy sound measurements for another worker. For example, if application 228 defines a "worker function" to be "welders," application 228 may determine that because all "welders" are working in a similar environment, with similar equipment, that the sound measurements from one, would also apply to the rest of the workers in the "welders" group.

FIGS. 5A-5B illustrate a user interface 500 that may be generated and output for display by application 228 and includes set up options related to noise information in accordance with one or more techniques of this disclosure. Section 502 allows a user to configure in application 228 specific noise sources, such as pieces of equipment (e.g., CNC Mulberry 8200 and Conveyor System) and to designate the location of the equipment in a work environment (e.g., CNC Shop). The location may be a work area, as shown, or may be more specific, such as a subsection of a work area. In some instances, the location may be designated by coordinates, addresses, or other location designation methods. Section 504 allows a user to input information related to area noise evaluations. Such information may include an area or location, the frequency with which noise is measured in that area, the last date it was measured along with measurement results, and the measurement tool used. In some examples, application 228 may receive this information (e.g., an area or location, the frequency with which noise is measured in that area, the last date it was measured along with measurement results, and the measurement tool used) from one or more portable computing devices, worksite computing devices, and the like that are associated various workers and/or worksites. In such examples, information included in section 504 may be automatically collected by application 228 and populated in user interface 500. Section 504 may also include other types of area evaluations such as fall hazards, heat hazards, welding hazards, temperature hazards, respiratory hazards, or any other types of hazards, along with each hazards corresponding measurement goals, measurement values, and collecting instruments.

Section 506 of FIG. 5B allows a user to enter noise exposure evaluations. Evaluations may be based on individuals or groups as shown. Evaluation information may include an indication of whether the individual or set of individuals of a group experienced an STS hearing shift, when the last noise measurement was made, the noise dose (e.g., raw or as a percentage of allowable dosage), the results of the noise measurement, and the tool or equipment used for measurement. In some examples, application 228 may receive this information (e.g., whether the individual or group experienced an STS hearing shift, when the last noise measurement was made, the noise dose (e.g., raw or as a percentage of allowable dosage), the results of the noise measurement, and the tool or equipment used for measurement) from one or more portable computing devices, worksite computing devices, and the like that are associated various workers and/or worksites. In such examples, information included in section 506 may be automatically collected by application 228 and populated in user interface 500. Section 506 may also include other types of area evaluations such as fall hazards, heat hazards, welding hazards, temperature hazards, respiratory hazards, or any other types of hazards, along with each hazards corresponding measurement goals, measurement values, and collecting instruments.

FIG. 6 illustrates a user interface 600 that may be generated and output for display by application 228 and includes noise measurement information related to an area in accordance with one or more techniques of this disclosure. FIG. 6 includes various types of area measurement history and related information that can be tracked as part of a safety program, such as a hearing conservation program. User interface 600 may represent data for a particularly defined area of worksite, such as a "CNC Shop" as previously configured by a user. For example, section 602 includes measurements of noise levels at various dates as compared to a baseline noise level measurement of 80 dBA. Section 602 may include information that indicates the device that captured the sound level or noise dosage (e.g., Noise Pro, Smart Phone, etc.), the person associated with the device that captured the sound level or noise dosage, one or more noise readings (e.g., Smith, J., Mark Mueller, etc.), and the sound level or noise dosage (e.g., 76 dBA, 79 dBA, etc.). In some examples, the measurements may visually distinguish outliers, anomalies, or values exceeding a threshold, such as outlier 606 that exceeds the baseline 608. In some examples, baseline 608 may be user-configured or generated by a computing device in application 228 or another application. In some examples, if application 228 detects an outlier, anomaly, or value exceeding a threshold, application 228 may generate alerts, re-configure PPE, or perform one or more additional operations. In some examples, section 602 may also include area measurements for one or more other metrics related to different types of PPE, such as fall protection hazards, respiratory hazards, welding hazards, and the like. Section 604 includes maintenance activity that occurred in the area to which the noise history measurement relate. Maintenance history can include what activity was taken, more detailed information regarding the action or equipment, the date the action was taken and the individual or entity that performed the action.

Figure 7:
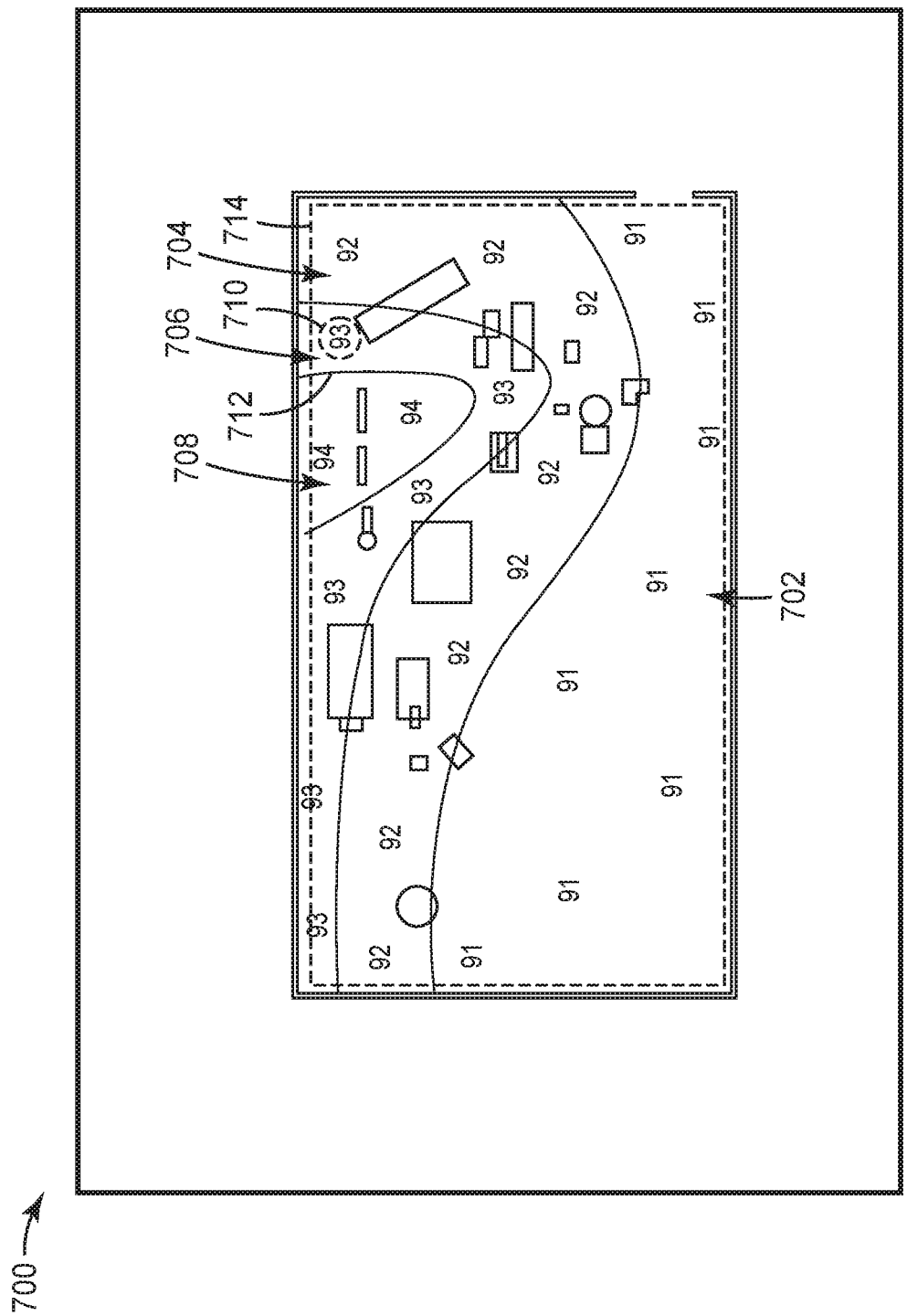
FIG. 7 illustrates a user interface that may be generated and output for display by application and that includes a measurement sound map for an area in accordance with one or more techniques of this disclosure.

FIG. 7 illustrates a user interface 700 that may be generated and output for display by application 228 and includes a measurement sound map for an area in accordance with one or more techniques of this disclosure. Measurement sound map 700 shows the levels of sound in various areas within a designated measurement area 714. Designated measurement area 714 in FIG. 7 is represented by an area that includes sound levels (e.g., sound level 710) and sound bars (e.g., sound bar 712). In region 702, the measured sound level is 91 dBA. In regions 704, the measured sound level is 92 dBA. In regions 706 the measured sound level is 93 dBA. And in regions 708, the measured sound level is 94 dBA. Measurement sound map 700 may be created using data from a variety of sources, such as dosimeters or sound level monitors worn by workers or positioned in designed measurement area 714 and used in combination with location information, environmental sensors located throughout the area, measurements taken by an auditor or other individual performing an assessment, or other noise measurement devices. Measurement sound map 700 may illustrate sound levels in an area at a particular point in time, or may update in real time, depending on the source of noise level data available. In some examples, application 228 may store data that defines an association between a particular location or sound region and a sound level for the location or region. In this way, if a worker is operating at a particular location or region, application 228 may determine or store data that indicates the sound level for the worker (and in some examples in association with a time and/or location).

In some examples, monitoring component 232 of computing device 200 may receive sound level data that indicates different sound levels at different, respective locations of a work environment represented by sound map 700. Monitoring component 232 may store the sound level data (which may be decibel values associated with locations, and in some examples times at which the decibel values were measured) in worksite data 242. Monitoring component 232 may also receive location data that indicates the respective locations of a worker within the work environment over time. Such data may be used to create a sound map 700. A portable computing device worn or otherwise associated with the worker may send location data to computing device 200, which is stored by monitoring component 232 in worker data 238. The location data may be GPS coordinates or other identifiers of locations within a work environment, such as but not limited to a beacon identifier at a particular location or other relative location.

Monitoring component 232 may determine, based on the location data received from the portable computing device, an amount of sound received by the worker over a period of time. For instance, monitoring component 232 may determine that for a portion of eight hours (e.g., a standard workday or other defined duration), the worker's activity was located at a set of particular locations and the sound levels at those particular locations for the respective times. In some examples, monitoring component 232 may select, based on an identifier of the worker, sound exposure data in worker data 238 associated with the worker for the period of time. Monitoring component 232 may sum the sound levels to a cumulative amount of sound to which the worker was exposed over the portion of the eight hours. Monitoring component 232 may determine how much remaining time the worker has in the work environment over the eight hour period before the worker will exit the environment.

Monitoring component 232 may identify one or more updated locations in the work environment having sound levels that are different from a current location of the worker. For instance, monitoring component 232 may determine, for other locations of the work environment having different sound levels, whether the worker would exceed a maximum allowable amount of sound exposure for the eight hour period if the worker moved to the respective updated location. Monitoring component 232 determine, for one or more locations the amount of sound exposure to the user if the user remained at the respective location for the remaining portion of the eight hours. For one or more of the updated locations, monitoring component 232 may select those updated locations for which the total sound exposure would not exceed a threshold maximum allowable amount of sound exposure for the eight hour period based on the sound attenuation provided by the article of hearing protection assigned to the worker. For instance, the total sound exposure for the worker may be computed based on (i) the amount of sound received by the worker over a period of time in a defined period of time prior to computing the total sound exposure and (ii) an amount of sound the worker would receive at the respective location for a remaining portion of the defined period of time that excludes the period of time. In some examples, monitoring component 232 may select or identify the updated location with the lowest amount of total sound exposure for the eight-hour period, while in other examples monitoring component 232 may select or identify any updated location with an amount of total sound exposure that amounts to less than an allowable dose in an eight-hour period (in some examples accounting for existing exposure of a worker to sound during the eight-hour period). In any case, monitoring component 232 may cause alert component 234 to generate and send a notification for the portable computing device that instructs the worker to move from the current location to the updated location. In this way, monitoring component 232 may cause the worker to move to different locations in the work environment so as to remain below the maximum allowable amount of sound exposure over the eight-hour period. Although an eight hour period has been used for example purposes, any defined duration specified in minutes, hours, days, weeks, or other intervals may be used.

In some examples, techniques of FIG. 7 may be extended to other types of PPE. For instance, application 228 may generate fall hazard map, respiratory map, heat map, or combination of different hazards in a work environment. In some examples, the application 228 may store data that defines associations between the locations of the hazards and the hazard. Application 228 may monitor the locations of a worker in the work environment in real-time and in some examples, determine that the worker is within a threshold distance of the hazard. In other examples, application 228 may determine that PPE data generated by one or more of the PPE with respect to a hazard indicates that a unsafe event may occur. Based on one or more of such determinations by application 228, application 228 may send alerts to the worker and/or other users, and/or send messages to one or more articles of PPE or articles of equipment in the work environment that cause the PPE or articles of equipment to change its respective operation. In some examples, the messages may configure the PPE or articles of machinery, but the messages may require a triggering condition to occur before the operation of the PPE or articles of machinery changes. For instance, if a worker is approaching a fall hazard with a certain clearance, application 228 may send a message that the self-retracting line in the fall protection harness lock up at a distance less than the clearance. The self-retracting line may not retract, though, until fall is detected that triggers the lock up.

In some examples, application 228 may receive real-time information about respiratory hazards such as particulate concentrations, particulate types and the like. Application 228 may determine, for a particular type of respiratory protection assigned to the worker, whether the worker will be at higher risk for exposure to respiratory hazards based on real-time measurements of the respiratory hazards. In some examples, application 228 may determine that if one user in a population of users is experiencing filter consumption at greater rate than others in the population, and the population works in the same work environment. If the filter consumption rate for the particular user is greater than threshold difference from a baseline consumption rate, then application 228 may generate an alert to the worker and/or one or more other users. In some examples, the alert may indicate that the work environment must be re-evaluated.

Figure 8A:
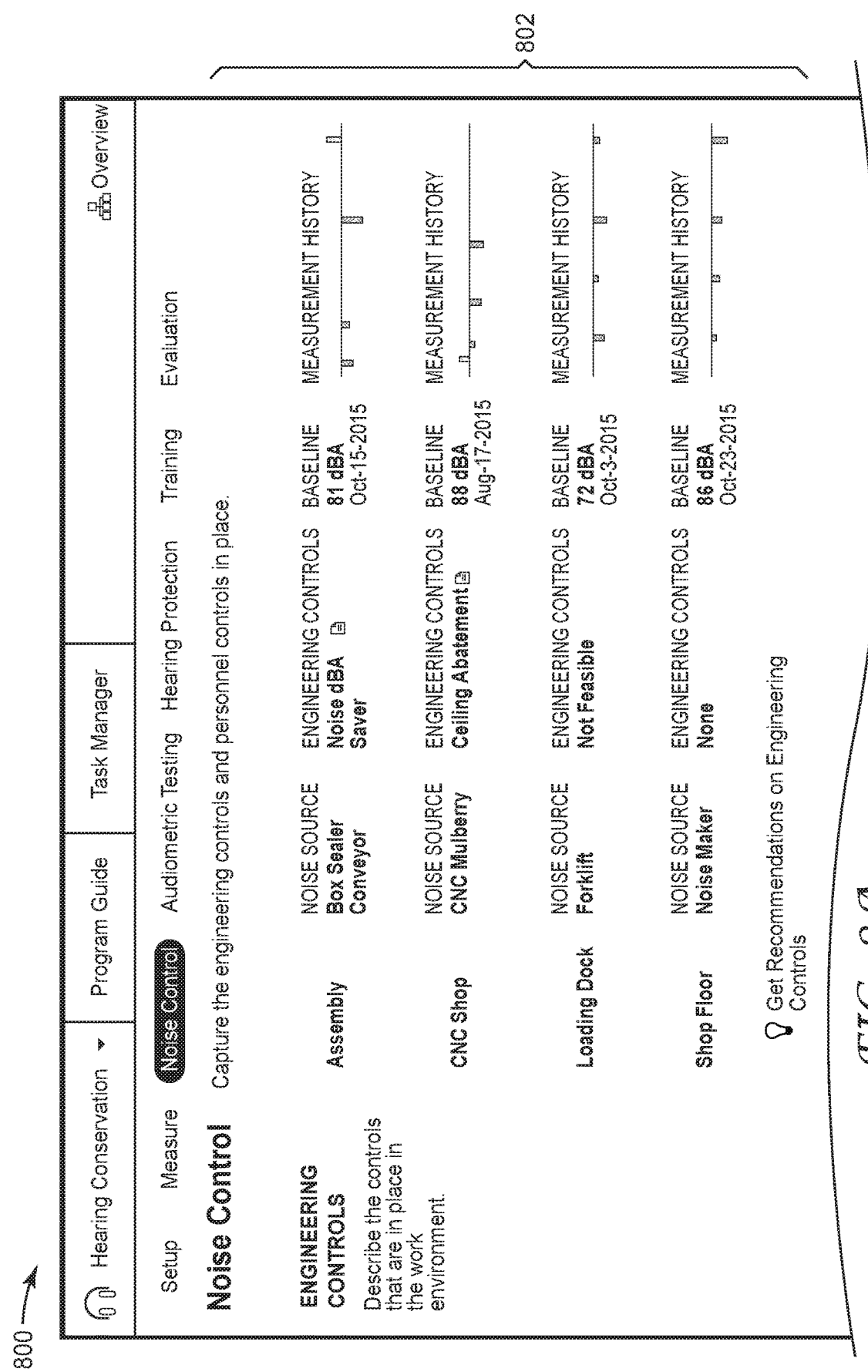

FIGS. 8A-8B illustrate a user interface 800 that may be generated and output for display by application 228 that includes noise controls and administrative controls for various areas in accordance with one or more techniques of this disclosure. FIG. 8A includes additional fields that display information related to noise controls and area administrative controls associated with a safety program, such as a hearing conservation program. Section 802 shows information related to controls that are in place in various areas. For example, in the Assembly area, the Box Sealer Conveyor is a source of noise. To reduce the level of noise, the control put in place is the Noise dBA Saver. The baseline noise level for this area recorded on Oct. 15, 2015, is 81 dBA. The last section ("measurement history") in this row shows a graphical representation of noise measurements taken in the Assembly area as compared to the baseline for the Assembly area. The other rows in section 802 show parallel information for other areas. Section 804 of FIG. 8B includes fields and other input controls related to administrative controls and policy information for various areas. For example, the first line indicates that in the CNC shop, work groups have time/date limits of being present in the CNC shop for a maximum of two hours per day. The following rows show parallel types of information for other areas. FIGS. 8A and 8B may also be extended to other types of PPE. For instance engineering controls placed in the environment may also control or mitigate fall protection hazards (e.g., implementing anchors), welding hazards (e.g., curtains or movable barriers), respiratory hazards (e.g., ventilation devices), or any other types of engineering controls.

Figure 9A:
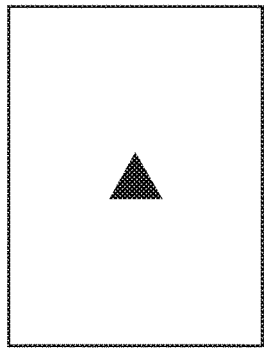

FIGS. 9A-9B illustrate user interface 900 that may be generated and output for display by application 228 that includes worker administrative controls, training materials and equipment history in accordance with one or more techniques of this disclosure. The fields shown on this user interface can be edited or simply viewed. Section 902 includes various worker administrative controls that are in place for workers who have experienced over exposure. For example, as shown in the first row, a worker named T. Bartsal is limited to a maximum of four hours per day in the CNC shop. Worker T. Bartsal has experienced a hearing shift as a result of over-exposure as indicated by the corresponding checkbox. The lines below show administrative controls for other workers, D. Falway and S. Miller. Section 904 shows links to training materials. Training materials may include videos, documents, work sheets and other materials that would be useful to a safety manager or a worker in learning about or improving hearing conservation. In some examples, a notification to view training materials may be sent by application 228 to a computing device of a worker with overexposure. Section 906 of FIG. 9B includes equipment history, and more specifically, maintenance history for equipment. The first line shows that an activity of equipment installation was completed on Jan. 22, 2015 by Bart Randolf. The following lines show additional types of maintenance activities and information associated with those activities. FIGS. 9A-9B may also be extended to any other types of PPE.

FIG. 10 illustrates a user interface 1000 that may be generated and output for display by application 228 and that includes maintenance records in accordance with one or more techniques of this disclosure. Specifically, user interface 1000 illustrates maintenance history for the Noise dBA Saver piece of equipment. The table 1002 included in user interface 1000 shows the date activity was performed, what activity was performed, notes related to the activity and the individual or entity that performed the activity. FIG. 10 may also be extended to any other types of PPE.

FIGS. 11A-11B illustrate a user interface 1100 that may be generated and output for display by application 228 and that includes information related to audiometric testing in accordance with one or more techniques of this disclosure. Section 1102 includes a schedule for audiometric testing based on area. For example, as shown in the first line, workers in the CNC show are tested on a monthly basis, and the last hearing measurement for the group was taken four days ago. A user can input information into this section to create additional schedules. Section 1104 lists workers who have experienced an STS hearing shift. For example, worker Z. Outlander has experienced a hearing shift. Outlander does not have assigned hearing protection, and the last hearing measurement was taken 94 days ago. Section 1106 provides additional training materials related to audiometric testing. Training materials may include videos, documents, work sheets and other materials that would be useful to a safety manager or a worker in learning about audiometric testing. Section 1108 indicates audiometric tests that are approaching in time based on area in a work environment. Section 1110 indicates audiometric re-tests that approaching in time based on area in a work environment. FIGS. 11A-11B may also be extended to other health measurements for a worker such as vision, breathing health, or any other types of health measurements for worker biological faculties.

Figure 12:
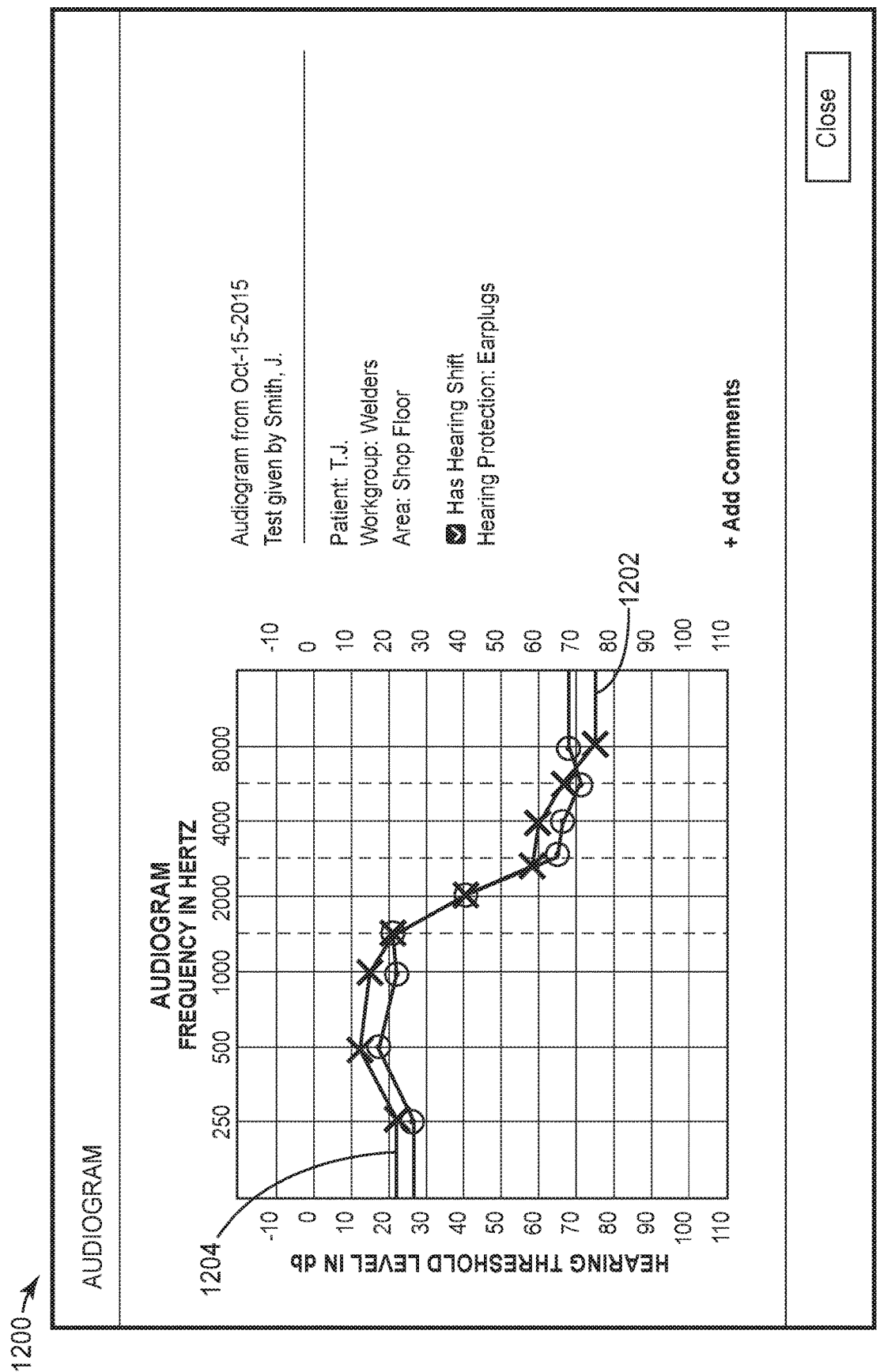
FIG. 12 illustrates a user interface that may be generated and output for display by application and that includes audiogram results for a particular worker in accordance with one or more techniques of this disclosure.

FIG. 12 illustrates a user interface 1200 that may be generated and output for display by application 228 and that includes audiogram results for a particular worker in accordance with one or more techniques of this disclosure. The results are graphed on a chart where the vertical axis is the hearing threshold level in dB. The horizontal axis is the audiogram frequency in hertz. Line 1202 shows audiogram results for a single worker's left ear. Line 1204 shows audiogram results for audiogram results for a single worker's right ear. User interface 1200 includes additional information, such as the date the audiogram was administered, the name of the individual administering the audiogram, the area the individual and group work in, whether or not the individual has experienced a hearing shift and what type of hearing protection the individual uses.

Figure 13A:
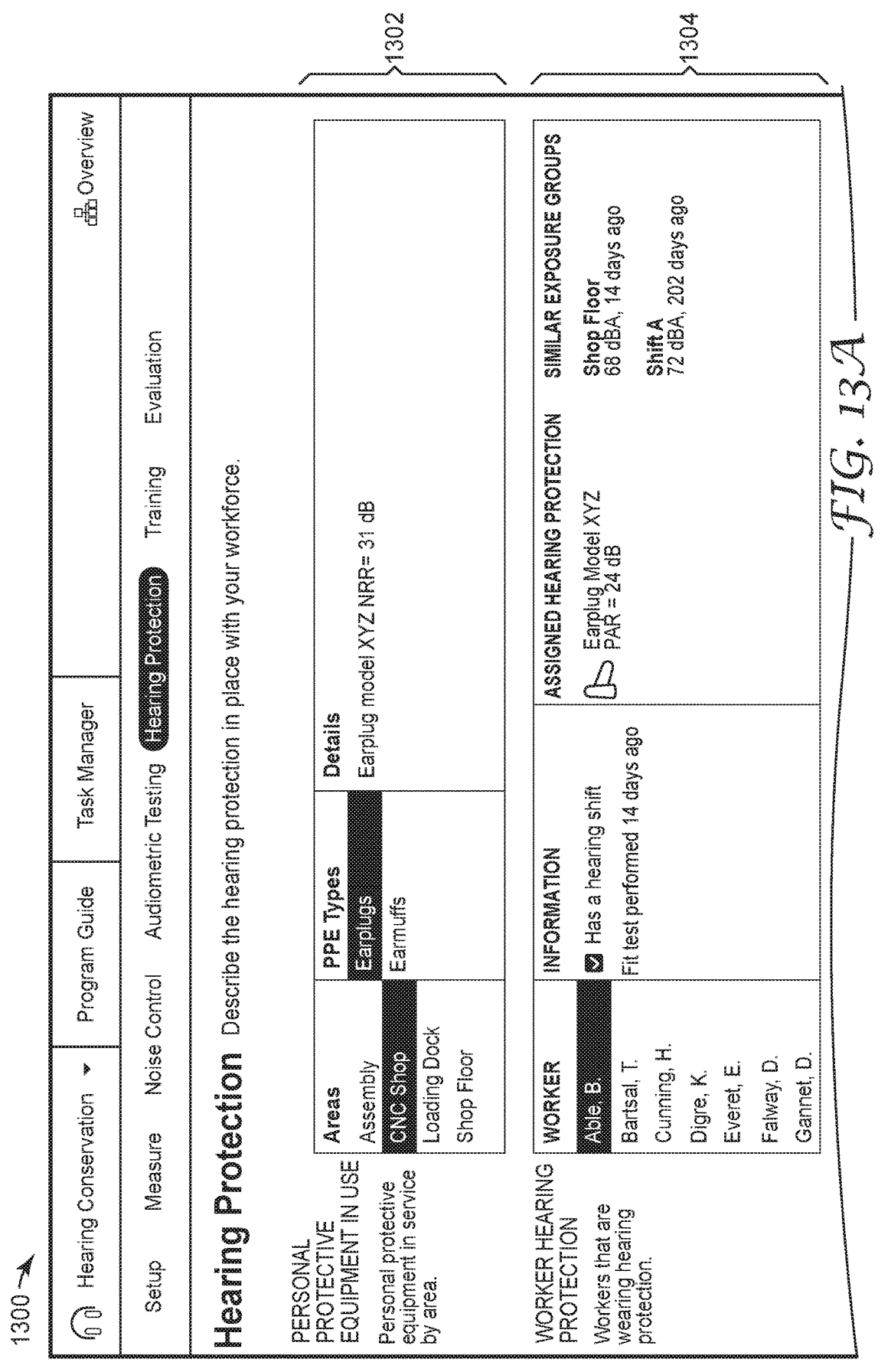

FIGS. 13A-13B illustrate a user interface 1300 that may be generated and output for display by application 228 and that includes information related to hearing protection products and workers using hearing protection in accordance with one or more techniques of this disclosure. Section 1302 includes what type of personal protective equipment is in use in various areas of a worksite or workplace. For example, in section 1302, the CNC shop is selected. When the CNC shop is selected, "earplugs" are highlighted, indicating that earplugs are used in the CNC shop. The third column indicates the standard noise reduction for the type of PPE in use. Section 1304 shows hearing protection equipment information for particular workers. For example, when worker B. Able is selected, the user interface 1300 shows that B. Able has a hearing shift and the most recent fit test was performed 14 days ago. B. Able is assigned to use earplugs Model XYZ. The last column ("similar exposure groups") includes the noise exposure group to which this particular worker is assigned. Section 1306 shows hearing protection products that could be used in the workplace, and the noise reduction rating associated with the pictured products.

In some examples, computing device 200 may recommend hearing protection or other PPE based on the types of available hearing protection or other PPE, fit-testing data, and characteristics of the work environment, such as the hazards or other conditions in the work environment. As an example, recommendation component 230 of computing device 200 may receive fit-testing data for a worker. The fit-testing data comprises a value indicating a noise level attenuation to the worker for a first type of article of hearing protection worn by the worker. As such fit testing data enables recommendation component 230 to determine the amount of sound attenuation provided by one or more different types of hearing protection, including at least the particular type of hearing protection worn by the worker when the hearing test was administered. As described in this disclosure, fit-testing may be a procedure performed for a worker in which a worker wearing a particular type of hearing protection is exposed to sounds to determine the level of protection or attenuation provided by the particular form of hearing protection. In the example of FIGS. 13A-13B, upon administering a fit-test to the worker, the fit test data may be manually input through a graphical user interface provided by UI component 228 and stored with worker data 238, or it may be automatically populated by recommendation component 230 in response to computing device 200 or any other computing device executing the fit test for the worker.

Recommendation component 230 may determine, based at least in part on the fit-testing data and sound level data of a work environment, whether sound attenuation provided by the first type of article of hearing protection satisfies a threshold for the work environment. For instance, Monitoring component 232 may receive sound level data of a work environment and store the sound level data in worksite data 242. The sound level data may indicate different sound levels at different locations of the work environment. In some instances, the different sound levels may be associated with timestamps. Although the following example is provided with respect to first and second types of hearing protection, any number of different types of hearing protection may be used in accordance with the techniques. In any case, recommendation component 230 may select the sound level data from worksite data 242 and determine whether the level of sound attenuation provided by the particular type of hearing protection for which the worker was fit-tested satisfies a threshold for the work environment. In some examples, the threshold is hard-coded by a provider of application 228 while in other examples, the threshold is machine-generated by application 228 or other computing device. In some examples of this disclosure, a threshold may be satisfied if a value compared to the threshold is greater than or equal to the threshold. In other examples a threshold may be satisfied if the value compared to the threshold is less than or equal to the threshold. In the example of FIGS. 13A-13B, if the level of sound attenuation is not greater than or equal to the threshold for the work environment, then the threshold is not satisfied. The threshold for the work environment may be based on sound level data entered manually by a user, captured by one or more portable sound level devices worn by workers, hard-coded, or provided to application 228 in any other manner.

In response to the determination by recommendation component 230 whether the sound attenuation provided by the first type of article of hearing protection satisfies the threshold, recommendation component 230 may cause UI component 228 to generate for display, a recommendation that indicates a second, different type of article of hearing protection for the work environment. For instance, UI component 228 may generate graphical user interfaces 13A-13B, which include section 1306 that indicate different types of recommended hearing protection for the work environment. Recommendation component 230 may select one or more different types of recommended hearing protection from equipment data 240 that provide sound attenuation greater than or equal to the threshold for the work environment.

In some examples, recommendation component 230 may select, in response to a determination that the threshold is not satisfied, a second type of article of hearing protection from equipment data 240, based at least in part on the second type of article of hearing protection providing sound attention that satisfies the threshold for the work environment. That is, if recommendation component 230 determines that the sound attention for the first type of hearing protection satisfies the threshold, recommendation component 230 will select at least the different, second type of hearing protection that provides sound attenuation satisfying the threshold for the environment. To identify one or more alternative types of hearing protection to the first type of hearing protection when the sound attenuation for the first type of hearing protection does not satisfy the threshold for the environment, recommendation component 230 may compare the sound level data of the work environment to the sound attenuation levels for a plurality of different types of articles of hearing protection included in equipment data 240. Recommendation component 230 may select a set of the plurality of articles of hearing protection that provide sound attenuation that satisfies the threshold, wherein the second, different type of hearing protection is included in the set of plurality of articles of hearing protection.

In another example, recommendation component 230 may cause UI component 238 to generate for display, in response to a determination that the threshold is satisfied, a graphical user interface that contemporaneously indicates the first type of article of hearing protection and the second type of article of hearing protection. That is, recommendation component 230 may generate a graphical user interface that includes both the first type of hearing protection which satisfies the threshold for the work environment and a second type of hearing protection that also satisfies the threshold and which may be an alternative or substitute to the first type of hearing protection.

In some examples, recommendation component 230 may exclude types of hearing protection from a recommendation if the hearing protection is incompatible with other types of PPE assigned to the worker. For instance, one or more ear-muff style hearing protectors may not be compatible with a protective helmet assigned to the worker or a headtop article worn on the head of a user that delivers purified air from a powered air purifying respirator. Equipment data 240 may include data defining one or more compatibility rules between different types of PPE, such as hearing protection and head protection. Recommendation component 230 may determine at least one type of personal protective equipment (PPE) assigned to the worker (e.g., based on data defining an association between the worker and equipment in worker data 238 and/or equipment data 240) other than hearing protection. Recommendation component 230 may determine whether a type of hearing protection is compatible with the at least one other type of PPE. Recommendation component 230 may select the type of hearing protection based on the determination that the second type of hearing protection is compatible with the at least one other type of PPE, for example, by determining whether a compatibility rule in equipment data 240 indicates that the type of hearing protection is compatible with the type of PPE. Recommendation component 230 may only select and include in FIG. 13A-13B types of hearing protection that are compatible with the other PPE assigned to the worker.

The aforementioned techniques for recommending hearing protection may also be extended to any other type of PPE. Application 228 may store information about different fall hazards in a work environment. Such fall hazards may include work platforms, ladders, mobile elevated equipment, drop-offs, or any other fall hazards. Based on locations associated with the hazards in the work environment, application 228 may generated recommendations for different types of fall protection equipment. For instance, application 228 may determine a set of fall protection hazards in a work environment based on fall hazard data stored by application 228. Application 228 may also be configured with one or more rules that map different fall hazards to different types of PPE. Based on the type of hazards, application 228 may select fall protection equipment that satisfies one or more rules and recommend the fall protection equipment to the user.

Such techniques may be similarly applied to respiratory equipment. For instance, based on respiratory hazards such as particulate concentration in the atmosphere, particulate type, and the like. Application 228 may store information about respiratory hazards in a work environment. Based on locations or overall environment conditions associated with the hazards in the work environment, application 228 may generate recommendations for different types of respiratory equipment. For instance, application 228 may determine a set of respiratory hazards in a work environment based on respiratory hazard data stored by application 228. Application 228 may also be configured with one or more rules that map different respiratory hazards to different types of PPE. Based on the type of hazards, application 228 may select respiratory equipment that satisfies one or more rules and recommend the respiratory equipment to the user.

In some examples, application 228 may provide a particular type of recommendation for one or more different types of PPE based on the type of work environment. For instance application 228 may store pre-configured sets of PPE, training, or other workflows for different types of work environment. Upon determining the type of work environment, application 228 may automatically output a recommendation of the pre-configured set of PPE, training, and workflow requirements for the type of work environment identified by application 228.

In some examples, application 228, and in particular, recommendation component 230 may a personal attenuation rating (PAR) and/or octoband rating (OR) separately or in conjunction with worksite environment sound measurements to recommend hearing protection. Whereas a PAR value may measure and weight an entire frequency range of sound, an octoband rating may divide such frequency in to sub-ranges (or octaves) and weight the respective octaves according the relative influence of that octave on human hearing. Recommendation component 230 may use an octoband measurement of attenuation for fit-testing of a user, and based on the measured sound levels in an environment, may recommend hearing protection based on the octoband measurement and the environment sound levels. In this way, rather than using a PAR value, techniques of the disclosure may provide a more accurate recommendation of hearing protection based on octoband values for attenuation and sound levels in the work environment.

In some examples, application 228 may receive, from a remote computing device (e.g., smartphone, desktop computer, tablet computer, etc.), PPE data and worker data based on indications of user input provided to a set of input controls included in at least one user interface generated by application 228 for display at the remote computing device, wherein the input controls receive at least PPE data that describes each of the set of articles of PPE and worker data that describes the worker. In response to selecting a prescribed set of the articles of PPE that satisfy one or more constraints imposed by a work environment of the worker and the set of articles of PPE, application 228 may generate for display at least one graphical user interface that includes respective graphical representations of the prescribed set of the articles of PPE, such as shown in FIG. 13A.

In response to receiving at least one indication of user input that selects one or more of the prescribed set of the articles of PPE for the worker, application 228 may store, based on the PPE data and the worker data, association data that defines an association between the worker and the selected one or more prescribed articles of PPE. Association data may be a record in a database with keys that identify the worker and one or more prescribed articles of PPE. After the worker has begun operating in the work environment with the selected one or more prescribed articles of PPE, application 228 may generate for output an indication of worker health (e.g., "has a hearing shift" in FIG. 13A or any other suitable message) for the worker that is based at least in part on each of: work environment data that describes the work environment during worker operation in the work environment and the association data between the worker and the selected one or more prescribed articles of PPE.

In some examples, the indication of worker health comprises a risk score based at least in part on a workers usage of PPE in the work environment. For instance, if the worker is unsafely or inconsistently using PPE in the work environment, the risk score may increase. If the worker is operating near a hazard in the work environment without the required PPE or using the PPE unsafely or inconsistently, then the risk score may increase. In some examples, if the worker is operating in the work environment with one or more biometric conditions that raise the risk the worker may suffer an adverse health effect (e.g., heat stroke, faint, etc.), then the risk score may increase. The risk score may be based one or more of the aforementioned metrics, each of which may be weighted. In some examples, the weights may be user-defined, machine-defined, or hard coded. In some examples, the risk score may be a sum of weighted products computed by application 228. Although the aforementioned example metrics have been described, many other metrics are possible. Moreover, where the risk score was described as increasing with the risk associated with a metric, the risk score may decrease with a decreasing risk in a metric.

In some examples, the output for indication may be a report and the indication of worker health as part of an aggregate population of workers health. In some examples, the report indicates a trend or anomaly in aggregate health of worker population. In some examples, application 228 generates a recommendation for training in response to the risk score satisfying a threshold. In some examples, application 228 may generate a task or a survey as shown in FIGS. 19A-20B.

FIG. 14 illustrates a user interface 1400 that may be generated and output for display by application 228 and that includes information relating to training schedules and training history in accordance with one or more techniques of this disclosure. Section 1402 includes scheduled training sessions. The top row in section 1402 indicates that there is an Employee Hearing Protection training section to be instructed by J. Smith on Nov. 12, 2015, with 146 individuals invited. The lower rows show additional upcoming training events. Section 1404 shows training session history. The top row in section 1404 shows that a Hearing Protection Refresher Course was presented on Jul. 15, 2015. There were 152 individuals present and no individuals absent. The user can choose the "View" link to see results related to the course. The lower rows show information related to other training events that have occurred. In some examples, application 228 may restrict a worker from checking out equipment from a designated area such as a tool locker unless application 228 determines that the worker identifier is associated with data that indicates the worker has completed all training required to use the equipment. FIG. 14 may be extended to training for any type of PPE.

Figure 15A:
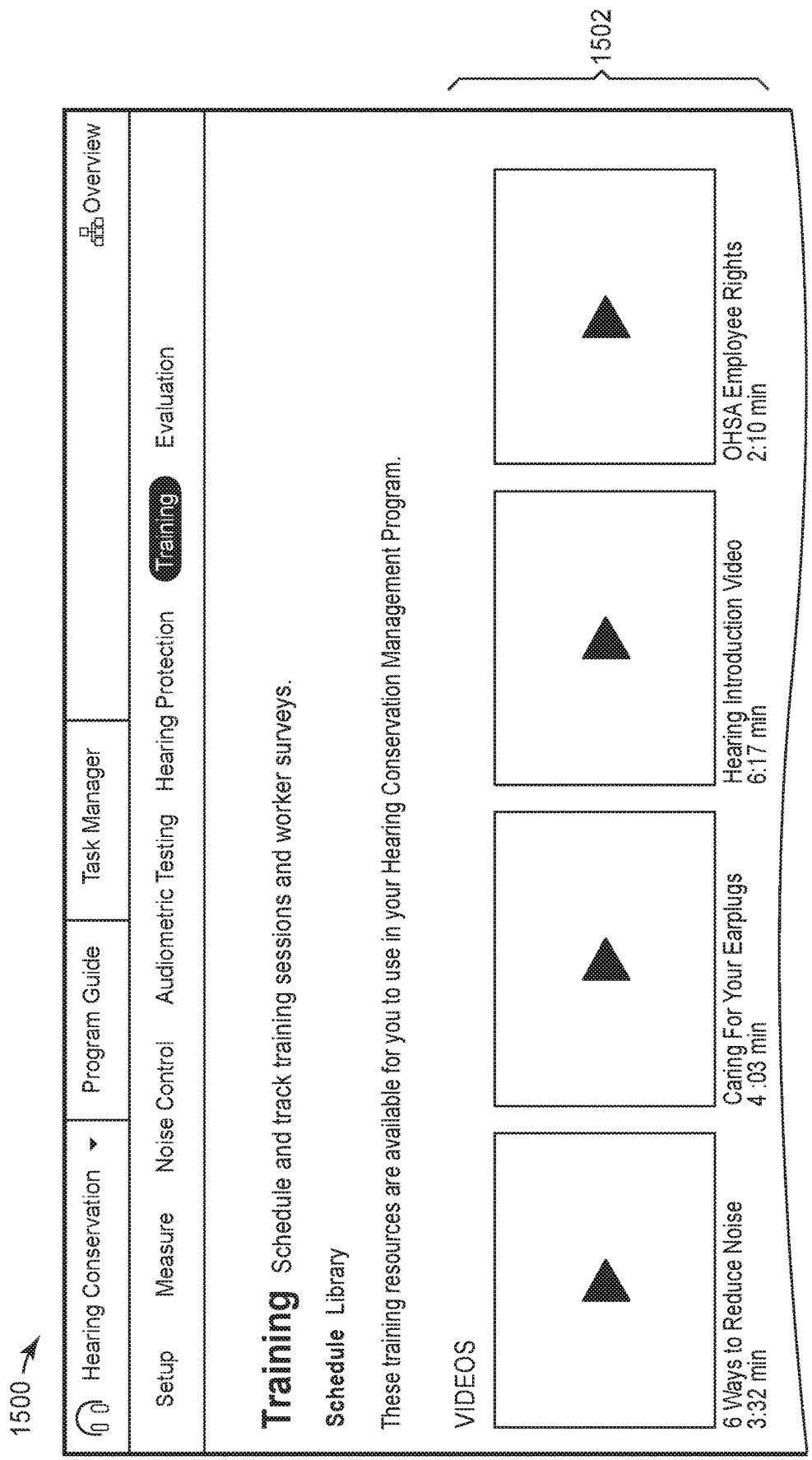
FIGS. 15A-15B illustrate a user interface that may be generated and output for display by an application and that includes information relating to training videos and documents in accordance with one or more techniques of this disclosure.
Figure 15B:
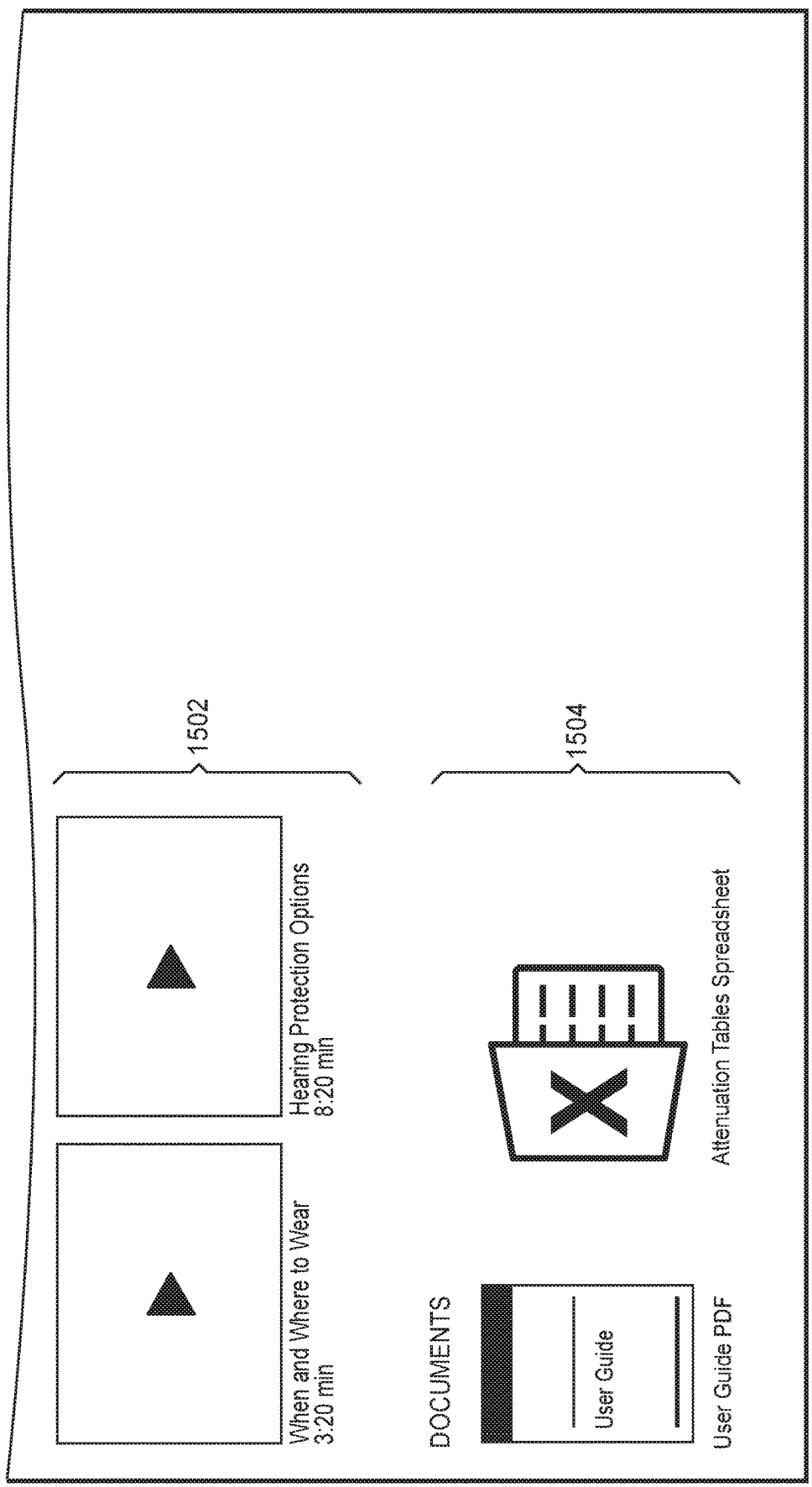

FIGS. 15A-15B illustrate a user interface 1500 that may be generated and output for display by application 228 and that includes information relating to training videos and documents in accordance with one or more techniques of this disclosure. In FIG. 15A, section 1502 includes links to a variety of videos that can be used in a Hearing Conservation Program. The videos may be viewed by a safety manager or by individual workers. In FIG. 15B, section 1504 includes documents useful in training, including a user guide for a hearing conservation program and an excel spreadsheet including tables and formulas for calculating attenuation. FIGS. 15A-15B may be extended to training for any type of PPE.

FIG. 16 illustrates a user interface 1600 that may be generated and output for display by application 228 and that includes training results in accordance with one or more techniques of this disclosure. Section 1602 includes training results. A user can enter a variety of information into this section, and it can be later viewed through the training history section 1404. Section 106 includes the title of the course, the date the course was taught, the number of attendees and individuals absent, and any other comments input by the instructor or safety manager. There is also an option for a user to schedule follow-up training on a selected date. FIG. 16 may be extended to training for any type of PPE.

Figure 17A:
FIGS. 17A-17B illustrate a user interface that may be generated and output for display by application and that includes evaluation information such as default reports, hearing trends and measurement comparisons in accordance with one or more techniques of this disclosure.
Figure 17B:
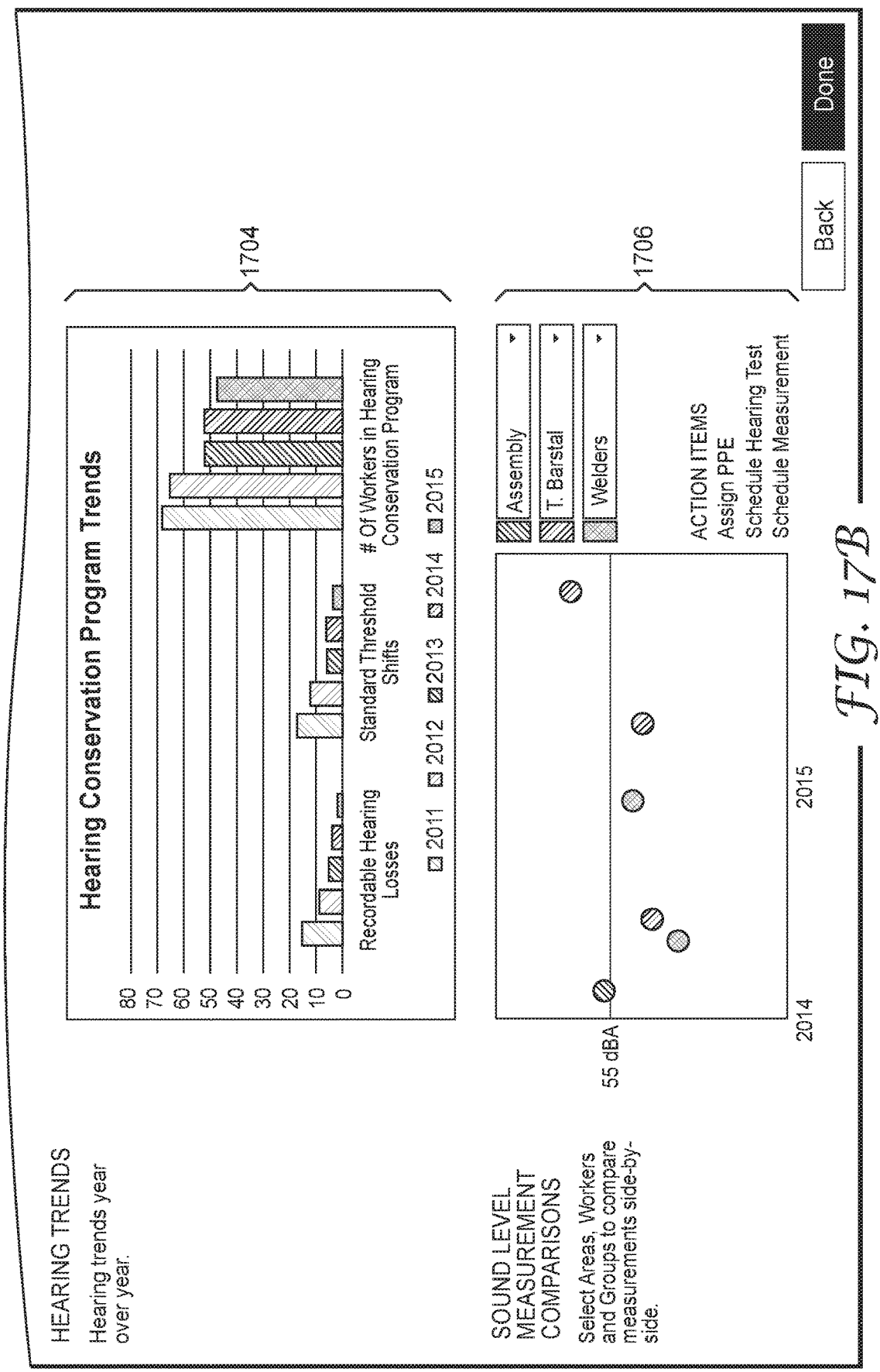

FIGS. 17A-17B illustrate a user interface 1700 that may be generated and output for display by application 228 and that includes evaluation information such as default reports, hearing trends and measurement comparisons in accordance with one or more techniques of this disclosure. Section 1702 includes a variety of default reports that a safety manager can access. Examples of default reports include a Worker Training Summary, Fit Testing Summary, Work Areas+dBA, Hearing Protection by Areas and Workers, Audiometric Tests Summary, and Noise Control Summary. Section 1702 may also include custom reports that may be generated by a user of application 228 in contrast to default reports which may be preloaded, prepackaged, hard-coded, or otherwise provided by the developer or seller of application 228. Section 1702 also includes trends, such as an indication that 8% of audiograms are worse than the previous set, and that there are 4 additional STS cases since a previous baseline was taken. Section 1704 shows hearing trends. The bar charts can indicate results for various hearing tests based on, for example, worker groups or work areas. They may also include, for example, what portion of workers in various work groups or work areas complete the required or recommended training. Section 1704 also includes some high-level statistics, such as the number of workers who have experienced a hearing shift, and the percentage of workers that have completed their required training. Section 1706 of FIG. 17B shows a comparison of hearing measurements for an individual, as compared to each of the individuals work group and those in the individual's work area. FIGS. 17A-17B may also be extended to other health measurements for a worker such as vision, breathing health, or any other types of health measurements for worker biological faculties.

FIG. 18 illustrates a user interface 1800 that may be generated and output for display by application 228 and that includes evaluation information such as active surveys and survey history in accordance with one or more techniques of this disclosure. Section 1802 includes survey results related to whether or not workers have taken training related to their specific administrative controls in place. It also includes what portion of audiograms indicate reduced hearing and how many new STS cases have been identified since a previous baseline was taken. Section 1804 includes survey history, with information such as the type of survey, the completion date and how many individuals participated in the survey. Section 1804 further includes information on how many workers have experienced a hearing shift and what percentage of workers have completed their training. FIG. 18 may also be extended to any types of surveys.

FIGS. 19A-19B illustrate a user interface 1900 that may be generated and output for display by application 228 and that includes survey results in accordance with one or more techniques of this disclosure. Section 1902 includes information related to a specific Hearing Protection Survey. It includes information such as the number of surveys completed and how many surveys remain pending, the actual questions included in the survey, and preliminary survey results. It also includes a field for entering survey results and comments, and for scheduling follow-up training as desired. Section 1904 may further include comments that may be input by a user for a survey as well as scheduling any follow-up training that may be required. FIGS. 19A-19B may also be extended to any types of surveys.

FIGS. 20A-20B illustrate a user interface 2000 that may be generated and output for display by application 228 and includes task manager information in accordance with one or more techniques of this disclosure. The task manager highlights program tasks and trends. For example, section 2002 illustrates what tasks are due in the present week. Section 2004 illustrates what tasks are due in the present month. And section 2006 illustrates tasks due in the present quarter. Tasks can include audiometric testing tasks, equipment maintenance tasks, workplace inspection tasks, or any other tasks associated with a work environment. FIGS. 21A-21B may also be extended to any types of surveys.

Figure 21:
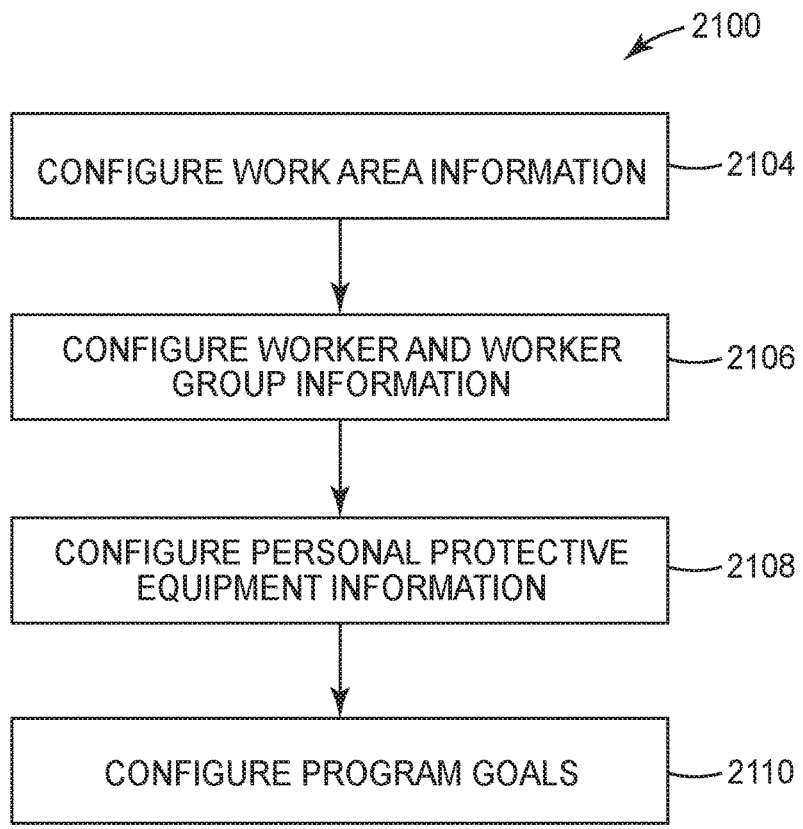
FIG. 21 illustrates a flow diagram including example operations of a computing device configured to perform program set up, in accordance with one or more techniques of this disclosure.

FIG. 21 illustrates a flow diagram 2100 including example operations of a computing device configured to perform program set up, in accordance with one or more techniques of this disclosure. For purposes of illustration only, the example operations are described below as being performed by application 228 executing at computing device 200. Application 228 may output for display a graphical user interface to configure a safety program. Configuration of the safety program may occur by one or more users of application 228 once in a given location, or may occur on an ongoing basis if a safety program such as a hearing conservation program is modified, or the location in which the program is implemented is modified. Application 228 may output for display a graphical user interface that includes one or more input controls to configure work area information such as in FIGS. 3A-3B (2104). Work area information can include a variety of pieces of information, such as the baseline noise level in the work area, any noise sources in the work area, what types of PPE are required for the work area, which individuals or work groups area allowed in the work area, and other information that may be helpful. Application 228 may receive data indicating user input values for the input controls in the graphical user interface for work area information. Such data may be stored at computing device 200 in worksite data 242.

Application 228 may output for display a graphical user interface that includes input controls to configure worker and worker group information (2106). Worker information can include basic identifying information, such as name, employee identification number, or a randomly assigned number for purposes of tracking and maintaining anonymity within the safety program. Worker information can include information related to whether the worker has completed a fit test for a particular item of PPE, and the date on which the test was completed, the date the worker last had an audiogram, worker training history, any PPE assigned to the worker, any portable computing devices assigned to the worker, and any smart tags or other communication or identification items assigned to the worker and enabling the worker to interact with the safety program. Worker group information can include names of worker groups, such as "Welders" or "Shift A". Worker group information may also include group statistics, such as what portion of a group has completed required training or has experienced an STS. Worker group information may further include restrictions or requirements for a particular group. For example, the "Welder" worker group may have a restriction of only being able to be in the CNC shop for four hours. Application 228 may receive data indicating user input values for the input controls in the graphical user interface for worker and worker group information. Such data may be stored at computing device 200 in worker data 238.

Application 228 may output for display a graphical user interface that includes input controls to configure PPE information (2108). PPE information may include information about hearing protection PPE or any type of PPE as discussed herein. PPE information may include identifying information for the PPE, age of PPE, worker to whom the PPE is assigned, PPE service information, rating or other standard-compliant information for the PPE, information regarding any smart tags, beacons or other electronic or communication devices attached to or associated with the PPE or that allows the PPE to interact with the safety program. Application 228 may receive data indicating user input values for the input controls in the graphical user interface for PPE information. Such data may be stored at computing device 200 in equipment data 240.

Application 228 may output for display a graphical user interface that includes input controls to configure safety program goals (2110). Examples of such graphical user interfaces may include FIGS. 3A-3B Program goals may include compliance goals, such as a certain percentage of workers or worker groups being fit tested or up to date on training Goals may also be results related, such as decreasing the number of STS cases among workers or work groups. Setting up program goals allows a safety manager to automatically and easily evaluate whether the safety program has aided in progressing toward the set goals for the program. Application 228 may receive data indicating user input values for the input controls in the graphical user interface for safety program goals. Such data may be stored at computing device 200 in worksite state 242.

Figure 22:
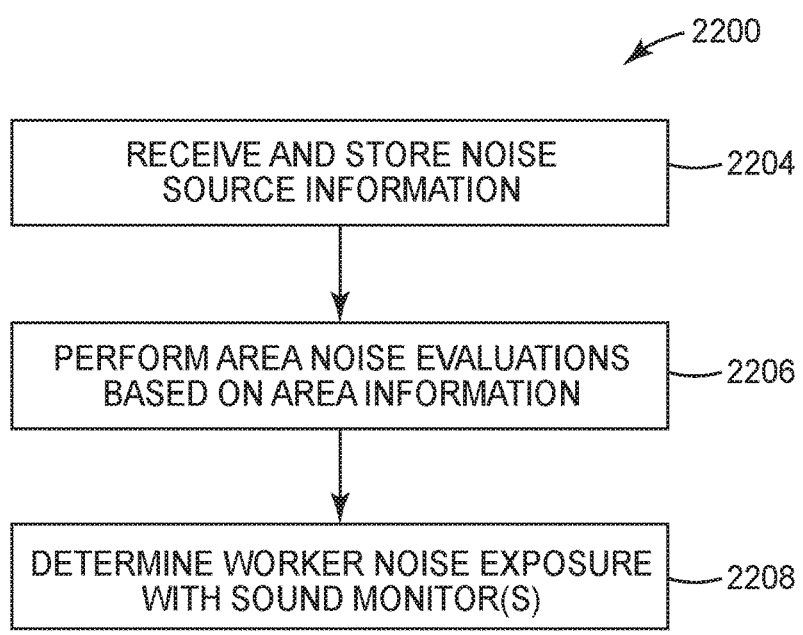
FIG. 22 illustrates a flow diagram including example operations of a computing device configured to perform measurement processes, in accordance with one or more techniques of this disclosure.

FIG. 22 illustrates a flow diagram 2200 including example operations of a computing device configured to perform measurement processes, in accordance with one or more techniques of this disclosure. For purposes of illustration only, the example operations are described below as being performed by application 228 executing at computing device 200. Operations 2204, 2206 and 2208 performed by application 228 may be recurring tasks that are repeated in and of itself before or after performing any other operations shown in flow chart 2200. Additionally, each of operations 2204, 2206 and 2208 may be performed outside of a measurement process. For example, each operation may be conducted on a periodic basis based on regulatory requirements, best practice and goals of the safety program.

Application 228 may collect and store information one or more sources of noise or sound (2204). This may include information such as the name of the noise source (e.g., the machine, device or other type of noise source), the location of the noise source, including which work area the noise source is located in, a noise level baseline associated with the particular noise source or the area that the noise source is in, and maintenance information related to the noise source. Such noise source information may be stored in worksite data 242.

Application 228 may receive data indicating area noise evaluations per area and storing historical data in worksite data 242 (2206). Noise area evaluations can include a sound level monitor performing repeated noise level measurements throughout the desired area to measure and identify the variation of noise levels within a given work area. Such noise level information may be sent to application 228. Storing the measurement results enables application 228 to identify trends, such as increased noise in the proximity of a particular noise source, or identify anomalies with respect to a baseline value. Application 228 may also determine worker noise exposure measurement with dosimeters (2208). For instance, application 228 may receive data from sound level monitors worn by a worker during a work shift and tracking level of noise to which the worker is exposed during the shift. Application 228 may store sound or noise levels in worker data 238 and/or worksite data 242. Dosimeter information may also be paired with location information, such as GPS coordinates, work area location or any other form of location information.

Figure 23:
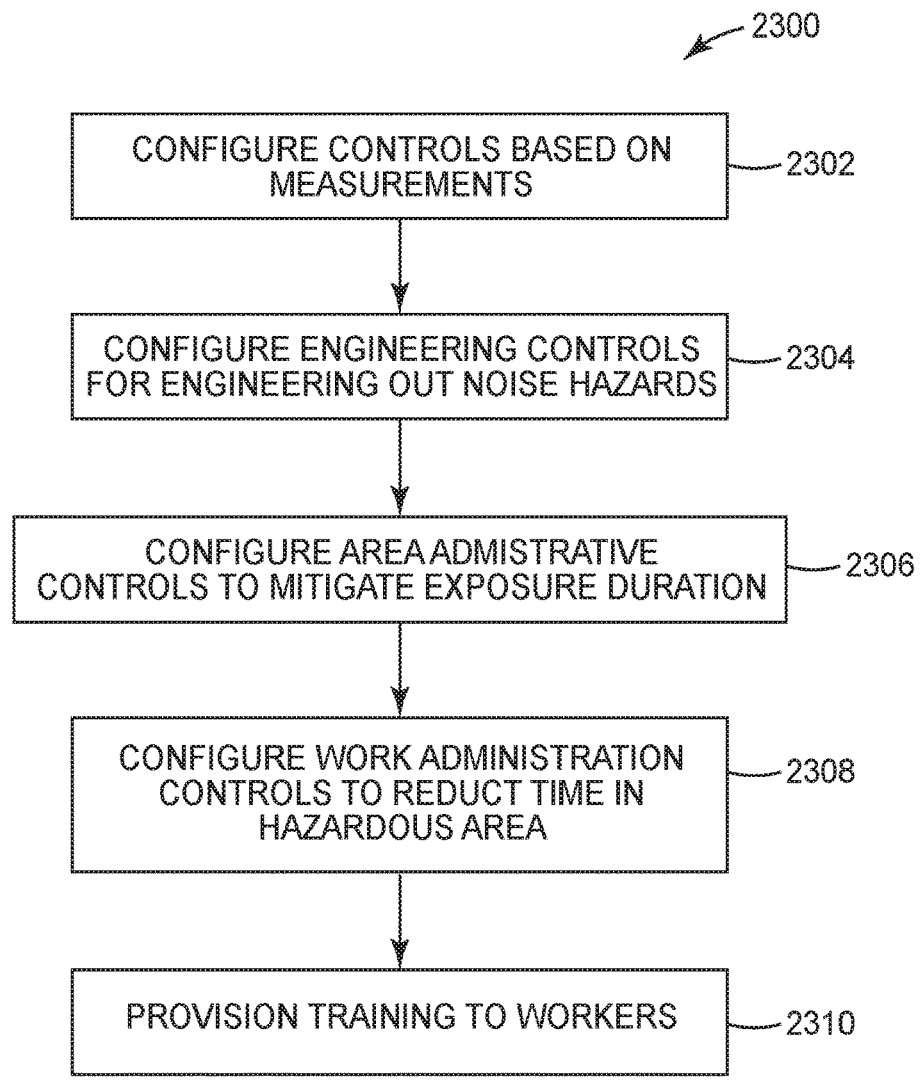
FIG. 23 illustrates a flow diagram including example operations of a computing device configured to set up controls in a safety system such as a hearing conservation system, in accordance with one or more techniques of this disclosure.

FIG. 23 illustrates a flow diagram 2300 including example operations of a computing device configured to set up controls in a safety system such as a hearing conservation system, in accordance with one or more techniques of this disclosure. For purposes of illustration only, the example operations are described below as being performed by application 228 executing at computing device 200. In some examples, operation 2302 may be a recurring operation. For instance, application 228 may repeatedly execute in and of itself before or after performing any other operations shown in flow chart 2302. Additionally, operation 2302 may be performed by application 228 outside of a control setting process. In the example of FIG. 23, application 228 configures controls based on measurements and may include setting up any type of controls based on measurements (2302). In some instances, application 228 may output a graphical user interface for display that enables a user to set up controls based on measurements. Controls may include restrictions on the operation of certain machinery or equipment, modifications or adaptations made to various noise sources, or engineering modifications or restrictions to the area or environment that a noise source is in that help to reduce the noise level. Application 228 may configure engineering controls if the noise hazard can be engineered out of a work environment (2304). In some instances, application 228 may output a graphical user interface for display that enables a user to set up controls that engineer noise hazards out of a work environment. For instance if the graphical user interface indicates an source of noise, the user may provide user input to add noise attenuating structures or changes to the work environment that eliminate or reduce the noise from the noise source. In some examples, the graphical user interface may allow the user to simulate the change in noise in the work environment based on adding or changing noise sources or noise attenuating structures or other modifications. This operation may be conducted in an instance where a particular noise source is creating an unusually high level of noise. This operation may also be conducted when noise generally in an area, such as a work area, can be decreased by controls such as sound damping techniques. In some examples, application 228 may automatically simulate multiple different locations for multiple different changes to noise sources or attenuating changes (e.g., adding barriers, turning off or changing machine operations, etc.), and determine which combination of changes to noise sources or attenuating changes will provide an optimal reduction in noise or a reduction in noise that satisfies a threshold value. Upon determining the combination of changes to noise sources or attenuating change, the changes to noise sources and/or attenuating change may be output for display as a recommendation of changes for the work environment.

In some examples, recommendation component 228 may determine one or more noise control priority factors (NCPF) for one or more noise sources in a work environment. A NCPF is described in Chapter 9 entitled "Noise Control Engineering," The Noise Manual, 2003, which is hereby incorporated by reference herein in its entirety. The NCPF may be calculated in the following way:

$$NCPF = \frac{NE \times LD \times EC \times SF \times PF}{CK}$$

where:
NE: Number of employees affected b source(s).
LD: Potential for noise to produce significant damage.
EC: Environmental characteristics factor.
SF: Problem solution potential success factor.
PF: Productivity factor.
CK: Estimated cost of controls (per thousand dollars).

In some examples, recommendation component 228 may calculate a NCPF for each noise source in an environment. Recommendation component 228 may identify or rank the noise sources in descending order. In some instances, recommendation component 228 may select or otherwise implement one or more changes to noise sources or attenuating changes (e.g., adding barriers, turning off or changing machine operations, etc.) to a subset of noise sources that have NCPF values that are greater than a threshold value. In some examples the threshold value may be user-defined, hard-coded by the provider of recommendation component 228 or machine generated. In some examples, recommendation component 228 may output for display or send one or more alerts to one or more users. The output or alerts may indicate which particular noise sources in the environment have an NCPF value that satisfies a threshold (e.g., greater than or equal to the threshold). In some examples, multiple NCPF values may be computed over time for a particular noise source to identify a trend or anomaly in the set of NCPF values. In some examples, a multiple sets of different NCPF values for difference noise sources may be compared to determine which particular noise source should be evaluated by a worksite manager.

Application 228 may configure area administrative controls to mitigate exposure duration (2306). A user may configure area administration controls that set limits on how long any individual may be present in the restricted area, work area, or work environment. In instances where the noise level in the area is increased above a threshold, the time an individual is allowed to be present in a work area may be decreased by application 228 in view of the increased noise level to limit the overall dose. As such, application 228 may alert the worker in the work environment and/or alert one or more other persons.

Application 228 may configure worker administrative controls to reduce time in a hazardous area (2308). For instance application 228 may output a graphical user interface to configure controls that apply to individual workers or to worker groups. For example, a particular worker who has experienced an STS may have a restriction on the number of hours the worker can be present in a particular work area, for example, the CNC shop. Application 228 may enforce the restriction by sending alerts to the worker and/or one or more other persons. Administrative controls may also generally apply to work groups, such as the Welders work group. Administrative controls may cause application 228 to limit the amount of time (by alerts, physical access, or other suitable techniques) an individual or a work group are exposed to a particular threshold noise level or the amount of time they are present in a given area.

Application 228 may also provision the delivery of training to workers (2310). Training may be required for individual workers or for worker groups. Training may relate to specific administrative controls, to ensure workers and worker groups understand what controls are in place, the reason for controls, and the impact of not complying with administrative controls. Training may also relate to other topics, such as what PPE is required for various work areas, training related to proper PPE selection and usage, training related to audiograms and the audiometric process, and training related to potential dangers of noise over-exposure without proper PPE. Application 228 may automatically notify workers of required training by sending messages to one or more computing devices, which may be associated with the workers or others responsible for the safety of the workers.

Figure 24:
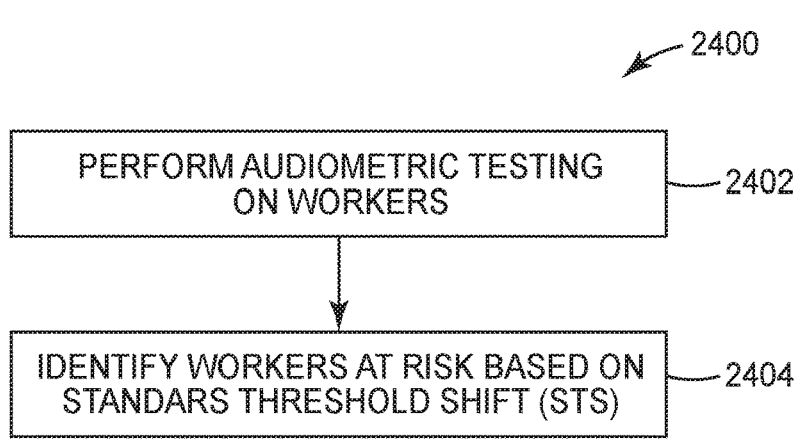
FIG. 24 illustrates a flow diagram including example operations of a computing device configured to analyze worker audiometric data, in accordance with one or more techniques of this disclosure.

FIG. 24 illustrates a flow diagram 2400 including example operations of a computing device configured to analyze worker audiometric data, in accordance with one or more techniques of this disclosure. For purposes of illustration only, the example operations are described below as being performed by application 228 executing at computing device 200. Application 228 may perform operation 2402 as a recurring task and may be repeated in and of itself before or after performing any other steps shown in flow chart 2400. Application 228 may conduct audiometric testing on workers and store historical data (2402). Testing may be conducted by a medical professional or other individual not associated with an employer or particular work environment while interoperating with a graphical user interface provided by application 228 that guides the professional or individual through the testing. Application 228 may receive data from one or more audio devices (noise source and/or hearing protection) used during the testing process. Application 228 may store historical data in the safety system as set forth herein, or may be stored in a separate location or database depending on the relevant data and personal information restrictions in the respective geography.

Application 228 may determine or otherwise identify whether workers are at risk based on standard threshold shift (STS) (2404). A standard threshold shift can be identified by application 228 by comparing the most recent audiogram results of a worker to the previous set of audiogram results and identifying differences. Further, application 228 may identify workers as being at risk by comparing an individual worker result to average results for the worker group that the worker is part of.

Figure 25:
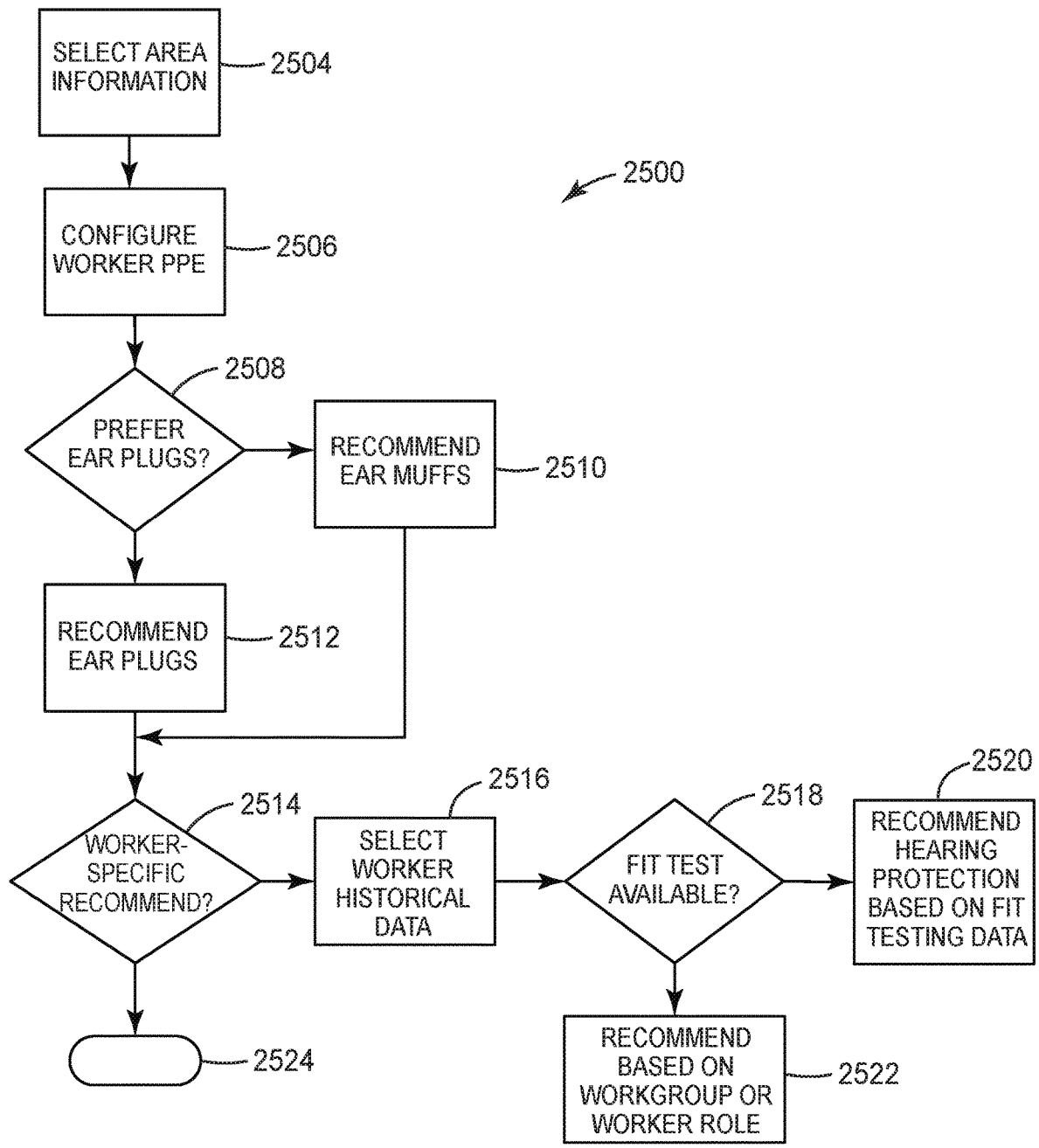
FIG. 25 illustrates a flow diagram including example operations of a computing device configured to recommend types of hearing protection based on known data, in accordance with one or more techniques of this disclosure.

FIG. 25 illustrates a flow diagram 2500 including example operations of a computing device configured to recommend types of hearing protection based on known data, in accordance with one or more techniques of this disclosure. For purposes of illustration only, the example operations are described below as being performed by application 228 executing at computing device 200. Application 228 may select information associated with a work area, which may be retrieved from worksite data 242 and/or worker data 238 (2504). The retrieved information may be historical data or data received by the system in real time from environmental sensors in the work area. Information may include a threshold noise level in the area, noise sources in the area, contaminant or other information in the area that may require a user to wear other types of PPE that would impact the type of hearing protection a worker would be able to wear. For example, if a worker is required to wear a respirator with a full face mask, it may be physically difficult for the user to also wear protective earmuffs.

Application 228 may configure different types of types of PPE that may be used for a work area (2506). In some examples, application 228 may output for a display a graphical user interface that enables worker or safety manager to input various types of PPE for the work area. In this step, a worker may enter any additional factors related to the work area that may not already be included in the information retrieved in operation 2504.

Application 228 may provide a graphical user interface in which a worker may indicate if the worker is interested in earplugs (2598). If the worker provides user input that she is not interested in earplugs, then application 228 may generate a recommendation for display that includes any earmuffs that meet the requirements for the particular work area assigned to the worker (2510). Application 228 generate a recommendation for a single set of earmuffs or multiple different types that the user can then choose from, depending on which earmuffs meet the requirements associated with the particular work area.

If application 228 determines that the user indicated that they were interested in earplugs, the application 228 recommends any earplugs that meet the requirements for the particular work area assigned to the worker (2512). Application 228 generate a recommendation for a single set of earplugs or multiple different types of earplugs that the user can choose from, depending on which earplugs meet the requirements associated with the particular work area.

Application 228 queries whether the user has requested PPE for a particular worker (2514). If user has requested for a PPE recommendation for a particular worker, the user may input to application 228 identifying information for the worker into application 228, and application 228 retrieves the worker's historical data (2516). Application 228 may determine whether fit test data is available for the worker for particular types of PPE (2518). If fit test data available, application 228 generates a specific recommendations based on the worker's past fit test data (2520). The recommendations can be based on information both related to the workers preferences (of earplugs or earmuffs) and data indicating which particular types of earplugs or earmuffs will provide the worker with the protection required for the particular area, based on the fit test data for that worker for the PPE. If there is not fit test data available for the worker, application 228 may generate a PPE recommendation based on pattern data (2522). Pattern data may include what type of PPE has offered appropriate levels of protection for individuals in similar the same or similar worker group, with the same or similar worker role, and based on physical similarities, such as height, weight, age and other factors that may impact the performance of the PPE for the particular worker. If application 228 receives input that the user indicates that they are not seeking a recommendation for a specific worker, the system skips selecting working specific information (2524), and provides the earmuff or earplug recommendations determined in operations 2510 and 2512 respectively.

Figure 26:
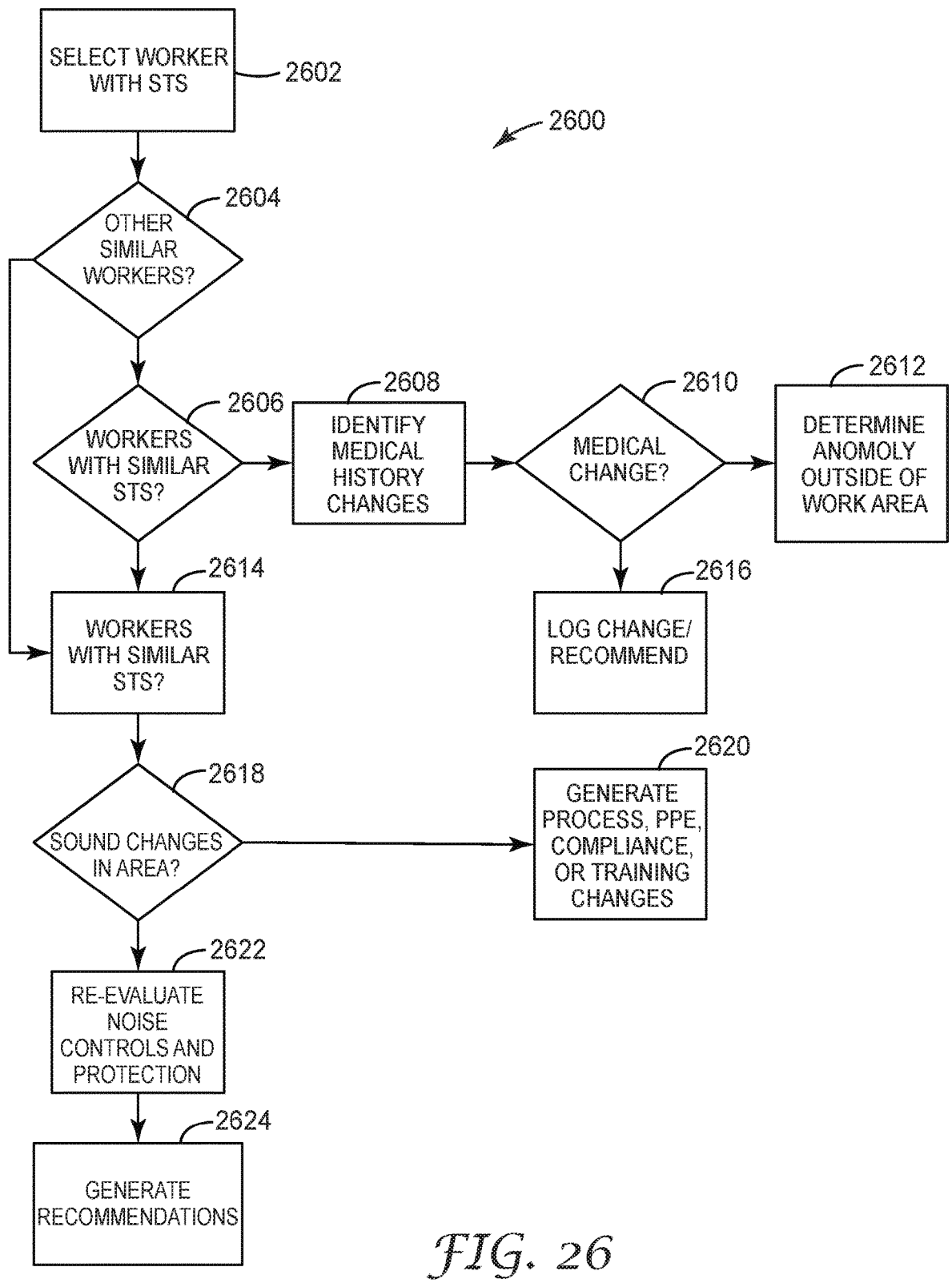
FIG. 26 illustrates a flow diagram including example operations of a computing device configured to analyze an occurrence of a worker exhibiting a standard threshold shift (STS), in accordance with one or more techniques of this disclosure.

FIG. 26 illustrates a flow diagram 2600 including example operations of a computing device configured to analyze an occurrence of a worker exhibiting a standard threshold shift (STS), in accordance with one or more techniques of this disclosure. For purposes of illustration only, the example operations are described below as being performed by application 228 executing at computing device 200. Application 228 may initially select data identifying a worker exhibiting an STS (2602). Application 228 may determine whether there are other workers in similar workgroups, worker areas, or worker roles as the selected worker (2604). If there are other workers in similar work groups, worker areas or worker roles, application 228 determines whether other workers in the workgroups, worker areas, or worker roles have exhibited similar STS trends (2606). If there are no other workers with similar STS trends, application 228 may retrieve medical data for the worker, and/or initiate a medical assessment for the worker to determine whether there are any changes in the worker medical history that have the potential to cause hearing damage or loss (2608). Application 228 may determine whether there are any such medical changes in the worker medical history (2610). If there are no such medical changes, in application 228 may determine that the hearing loss is an anomaly and/or that outside-of-work factors are most likely causing or affecting hearing loss or damage (2612). If there are medical history changes that could cause hearing damage or loss, application 228 logs the changes and/or generates a recommendation (2616), which may include different types of hearing protection, time in the work area, or activities performed in the work area. Other recommendations may include instituting administrative controls for the worker to provide proper limitations on the exposure the worker has to a certain noise threshold to prevent further STS. Other recommendations may also include generating a recommendation for further medical follow up.

If application 228 determines that there are other workers that exhibit similar STS trends, application 228 generates a recommendation and/or performs area monitoring for the area that the worker, or the other workers exhibiting similar STS trends, are present in (2614). In some instances, application 228 may perform such monitoring using real time data from environmental sensors. In some instances, application 228 may perform analysis using updated noise measurements taken in the area to recommend different worker activity in the work area and/or different types of hearing protection.

Application 228 may analyze whether there have been changes in the noise in the area or in the noise dose history associated with the area (2618). If there have been no changes in the noise in the area or the noise dose history associated with the area, application 228 may generate a recommendation for reassessment of one or more of several other potential factors, including any process changes, use of PPE and compliance to safety policies (2620). Application 228 may also recommend retraining employees and workers on safety inside work and outside of work.

If application 228 determines that the results of operation 2616 indicate that there have been changes in the noise level in the area or in the dose history associated with the area, application 228 generates a recommendation to reassess noise controls and the level of protection required for the area (2622). In some instances, application 228 may recommend specific additional noise controls for consideration and recommend specific increased levels of protection for the area, and what types of PPE may be able to provide those levels of protection, based either on PPE ratings or fit test data for workers assigned to work in the area. Application 228 may implement one or more recommendation selected by the user, for example by automatically initiating a training process notify workers of training on the new processes and requirements associated with the changes made to the safety program (2624). In the example of FIG. 26, various instances of application 228 generating a recommendation have been described. In some instances, generating a recommendation may further include outputting for display and/or sending the recommendation to one or more other computing devices. In some instances, generating a recommendation may further include logging or otherwise storing such recommendations.

Figure 27:
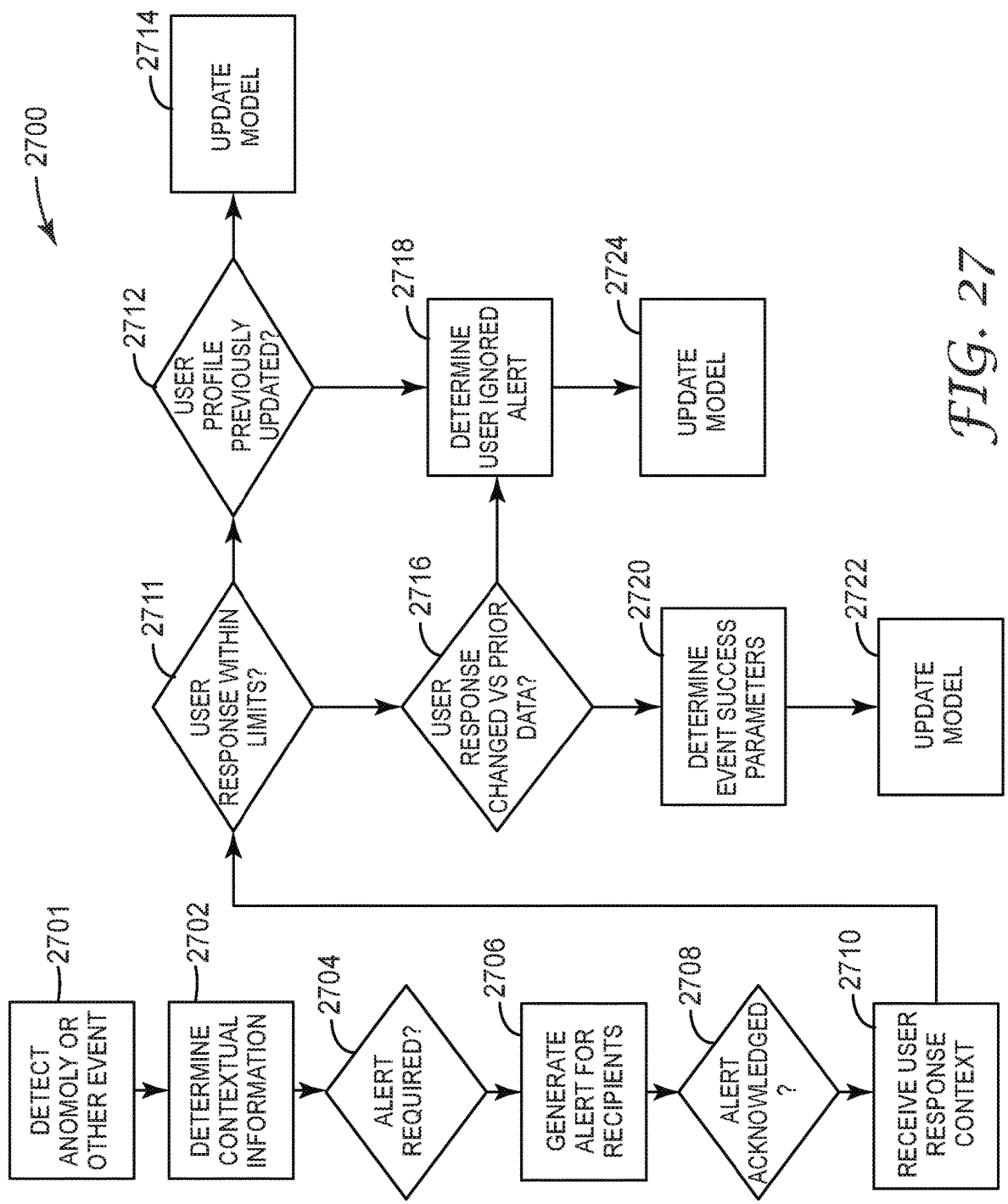
FIG. 27 illustrates a flow diagram including example operations of a computing device configured to perform machine learning for alerting workers or other users, in accordance with one or more techniques of this disclosure.

FIG. 27 illustrates a flow diagram 2700 including example operations of a computing device configured to perform machine learning for alerting workers or other users, in accordance with one or more techniques of this disclosure. For purposes of illustration only, the example operations are described below as being performed by application 228 executing at computing device 200. In this disclosure, in instances where a decision block (e.g., 2704) does not specify multiple alternative operations, application 228 may, when a condition of the decision block is not satisfied, proceed to terminate or switch to another flow of control comprising operations not included in the FIG.

Initially, application 228 may detect an anomaly event, abnormal event, or other notification event, such as a noise level satisfying a threshold or as otherwise described in this disclosure (2701). Upon detecting or determining the event, application 228 may determine contextual information, such as determining the worksite, worker identity, hearing protection, noise levels, duration of the noise levels, or any other information associated with the event (2702). In some examples, application 228 may compare or otherwise lookup safety and/or business rules that correspond to the contextual data to determine whether to generate an alert (2704). For instance, if a noise level satisfies a threshold (e.g., is greater than or equal to the threshold), application 228 may generate an alert (2706). Application 228 may send one or more alerts to one or more workers or other users associated with application 228. For instance, the alert may be based on a specific user profile, or a "standard" or template worker profile that may be generalized to any worker. Application 228 may send the alert to the worker and/or user(s).

Application 228 may determine whether the worker and/or user(s) acknowledged the alert (2708). In some examples, acknowledging the alert may include, viewing the alert, selecting the alert, dismissing and/or deleting the alert, and/or responding to the alert with some further action. Application 228 may receive data from a remote computing device of the worker and/or user(s) that indicates metadata associated with the acknowledgement of the user (2710). For instance, the metadata may include how much time elapsed before the user acknowledged the alert, the particular form of acknowledgment, timestamp information for when the user acknowledged the alert, the device and/or type of device on which the user acknowledged the alert, the activity the user was engaged in at the time that the alert was acknowledged.

Application 228, upon determining that the user has acknowledged the alert, may determine whether the user reaction is within pre-defined limits and/or within the specific user's usual limits (2711). For instance, a limit may be a duration of time, a particular set of one or more conditions, and/or one or more thresholds. If the user did not acknowledge the alert within a defined limit, then application 228 may determine whether the user's profile has been previously updated based on previously determining that the user did not acknowledge the alert within a defined limit (2712). If the user's profile has not been updated based on previously determining that the user did not acknowledge the alert within a defined limit, application 228 may update the user's profile to indicate the user did not acknowledge the alert within the defined time limit (2714). For instance, the user-profile may be a model having one or more weighted variables that represent different characteristics or limits themselves. The model may be modified by application 228 based on positive or negative reinforcement corresponding to the user acknowledging or ignoring a notification. If the user's acknowledgement is outside user-specific and/or pre-defined limits, application 228 may modify one or more of the weights the variables. In some examples, no weights may be used and the variable itself may be modified. For instance, first and second variables may be lower time threshold duration and upper time threshold duration. If the time duration for a user to acknowledge an alert is less than the lower time threshold duration, application 228 may decrease the lower time threshold duration.

If application 228 determines that the user's profile has been previously updated based on previously determining that the user did not acknowledge the alert within a defined limit, application 228 may determine that the user has been de-sensitized to the alerts or consistently receives such alerts because the user consistently engages in activities that trigger anomalies or abnormal events (2718). As such, application 228 may use contextual information at alert time, along with user actions to define a new or updated alert notification profile (2724). For instance, the new or updated alert notification profile may use a different form of notification, different time for notifying, or may utilize any other change in notification to improve the likelihood of a user viewing the alert.

Returning to operation 2716, if application 228 determines that a user's reaction time has improved compared to prior data, application 228 may determine that the learning technique applied in FIG. 27 was effective in causing the user to acknowledge an alert. Accordingly, application 228 may capture event parameters from the alert, and update baseline data in the learning model and/or in the user profile based on the event parameters (2720). Event parameters may include but are not limited to: type of alert, time of alert, type of acknowledgement to the alert, or any other information associated with the alert. By storing the capture event parameters from the alert, application 228 may update the model (e.g., baseline data) by which application 228 determines whether a user's reaction is within pre-defined and/or user specific limits (2722). As described above the user profile or baseline data may refer to the model that is updated by application 228.

Figure 28:
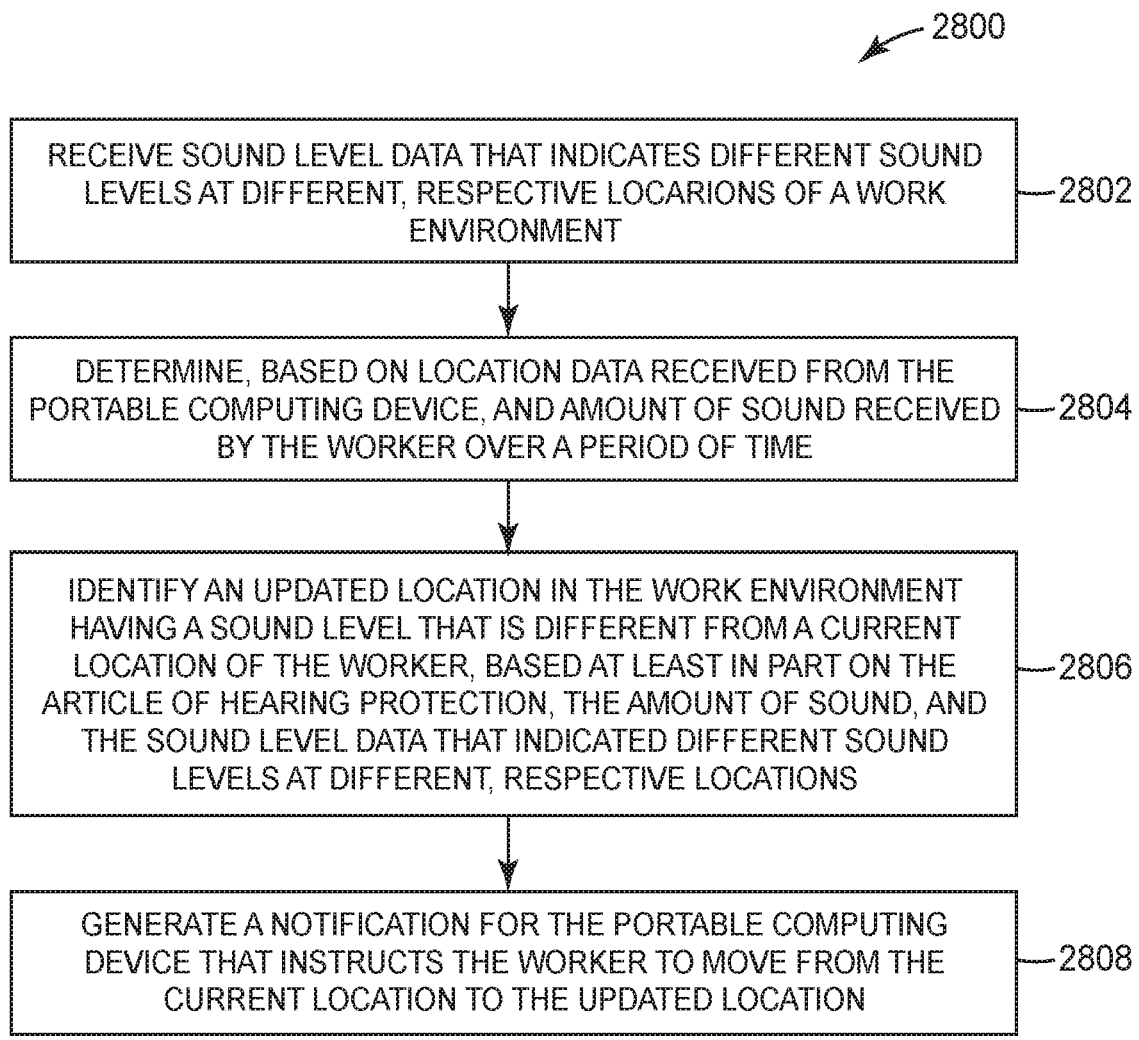
FIG. 28 illustrates a flow diagram including example operations of a computing device, in accordance with one or more techniques of this disclosure.

FIG. 28 illustrates a flow diagram 2800 including example operations of a computing device, in accordance with one or more techniques of this disclosure. For purposes of illustration only, the example operations are described below as being performed by application 228 executing at computing device 200. In some examples, application 228 may receive sound level data that indicates different sound levels at different, respective locations of a work environment (2802). Application 228 may determine, based on location data received from the portable computing device, an amount of sound received by the worker over a period of time (2804). In some examples, application 228 may identify an updated location in the work environment having a sound level that is different from a current location of the worker, based at least in part on the article of hearing protection, the amount of sound, and the sound level data that indicates different sound levels at different, respective locations (2806). In some examples, application 228 may generate a notification for the portable computing device that instructs the worker to move from the current location to the updated location (2808).

Figure 29:
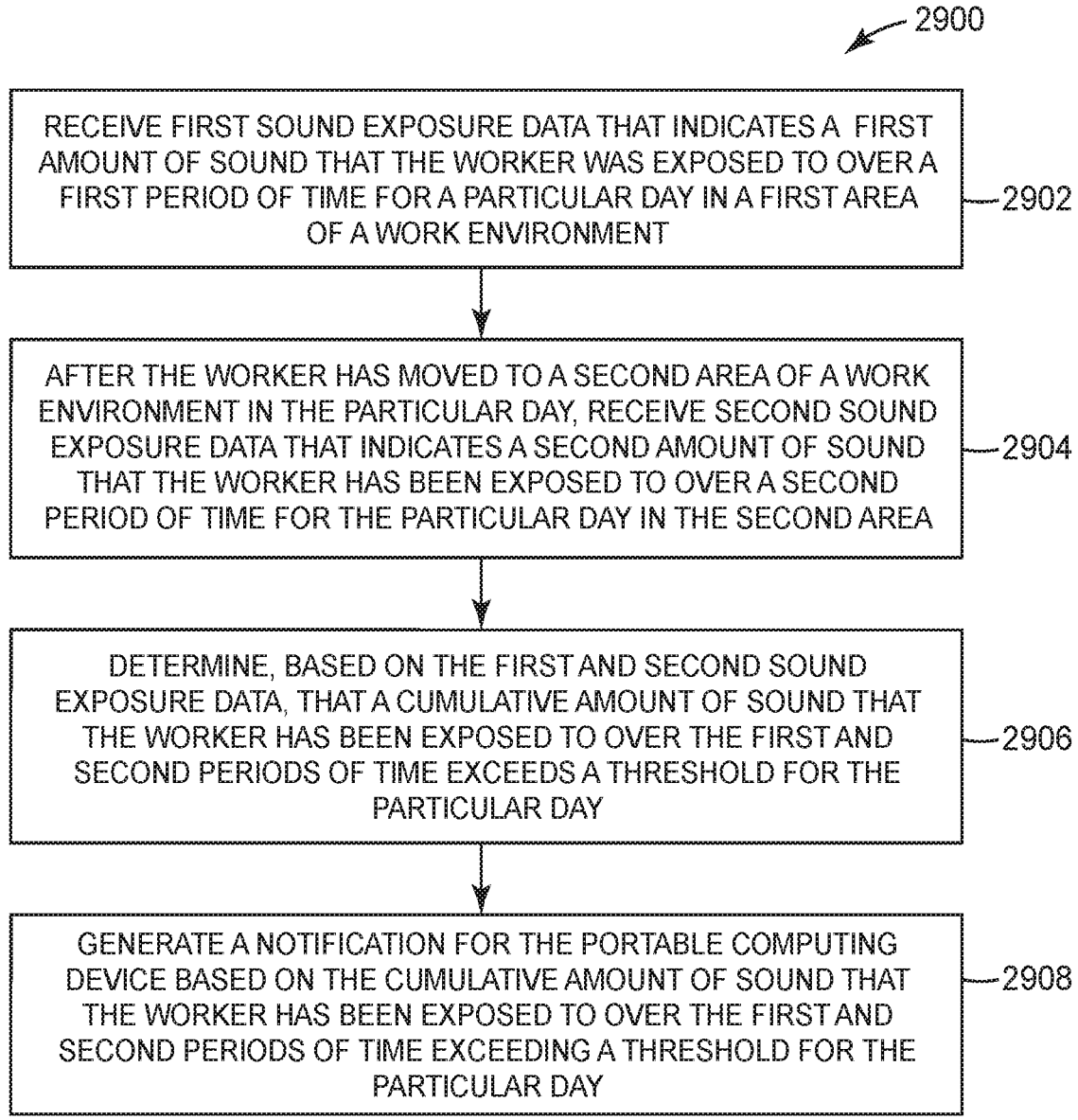
FIG. 29 illustrates a flow diagram including example operations of a computing device, in accordance with one or more techniques of this disclosure.

FIG. 29 illustrates a flow diagram 2900 including example operations of a computing device, in accordance with one or more techniques of this disclosure. For purposes of illustration only, the example operations are described below as being performed by application 228 executing at computing device 200. In some examples, application 228 may receive first sound exposure data that indicates a first amount of sound that the worker was exposed to over a first period of time for a particular day in a first area of a work environment (2902). After the worker has moved to a second area of a work environment in the particular day, application 228 may receive second sound exposure data that indicates a second amount of sound that the worker has been exposed to over a second period of time for the particular day in the second area (2904). In some examples, application 228 may determine, based on the first and second sound exposure data, that a cumulative amount of sound that the worker has been exposed to over the first and second periods of time exceeds a threshold for the particular day. Application 228 may generate a notification for the portable computing device based on the cumulative amount of sound that the worker has been exposed to over the first and second periods of time exceeding a threshold for the particular day (2908).

Figure 30:
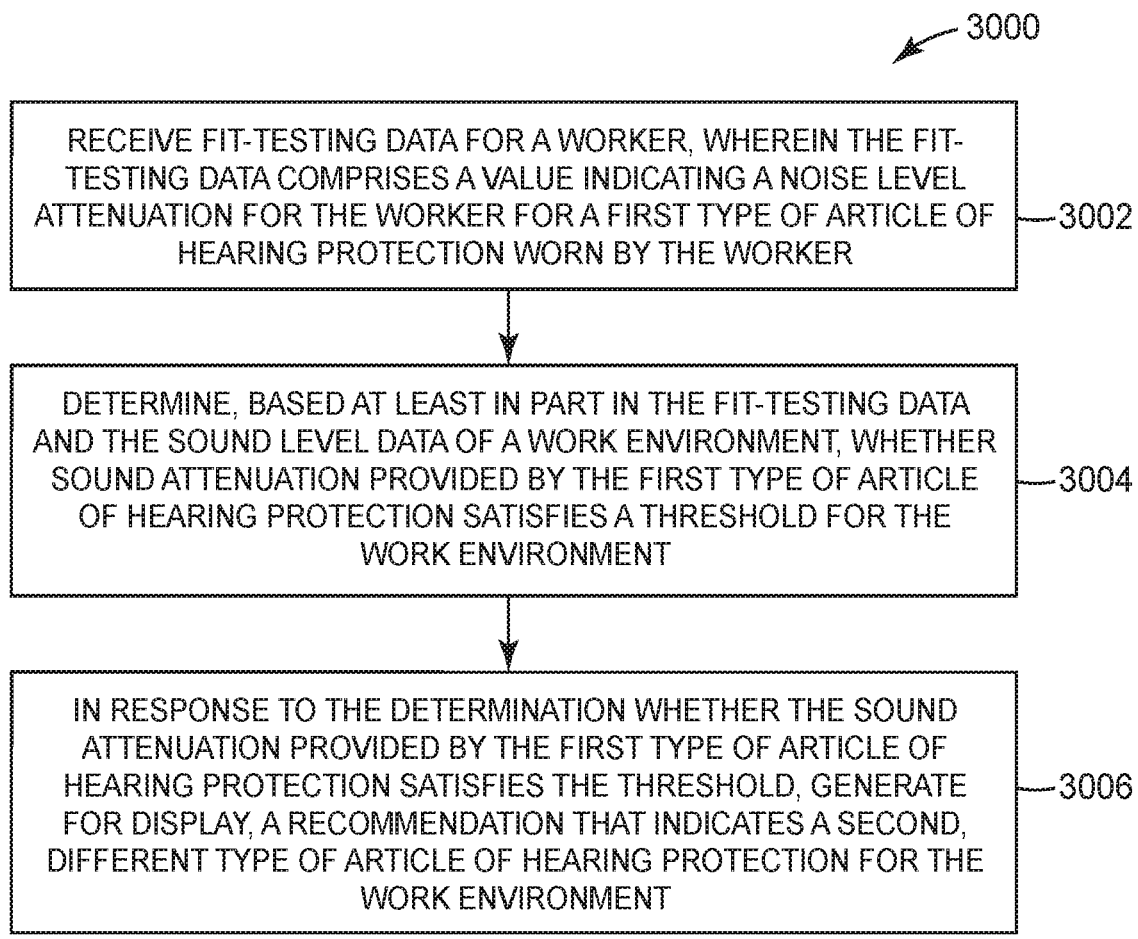
FIG. 30 illustrates a flow diagram including example operations of a computing device, in accordance with one or more techniques of this disclosure.

FIG. 30 illustrates a flow diagram 3000 including example operations of a computing device, in accordance with one or more techniques of this disclosure. For purposes of illustration only, the example operations are described below as being performed by application 228 executing at computing device 200. Application 228 may receive fit-testing data for a worker, wherein the fit-testing data comprises a value indicating a noise level attenuation for the worker for a first type of article of hearing protection worn by the worker (3002). In some examples, application 228 may determine, based at least in part on the fit-testing data and sound level data of a work environment, whether sound attenuation provided by the first type of article of hearing protection satisfies a threshold for the work environment (3004). Application 228 may in response to the determination whether the sound attenuation provided by the first type of article of hearing protection satisfies the threshold, generate for display, a recommendation that indicates a second, different type of article of hearing protection for the work environment (3006).

Figure 31:
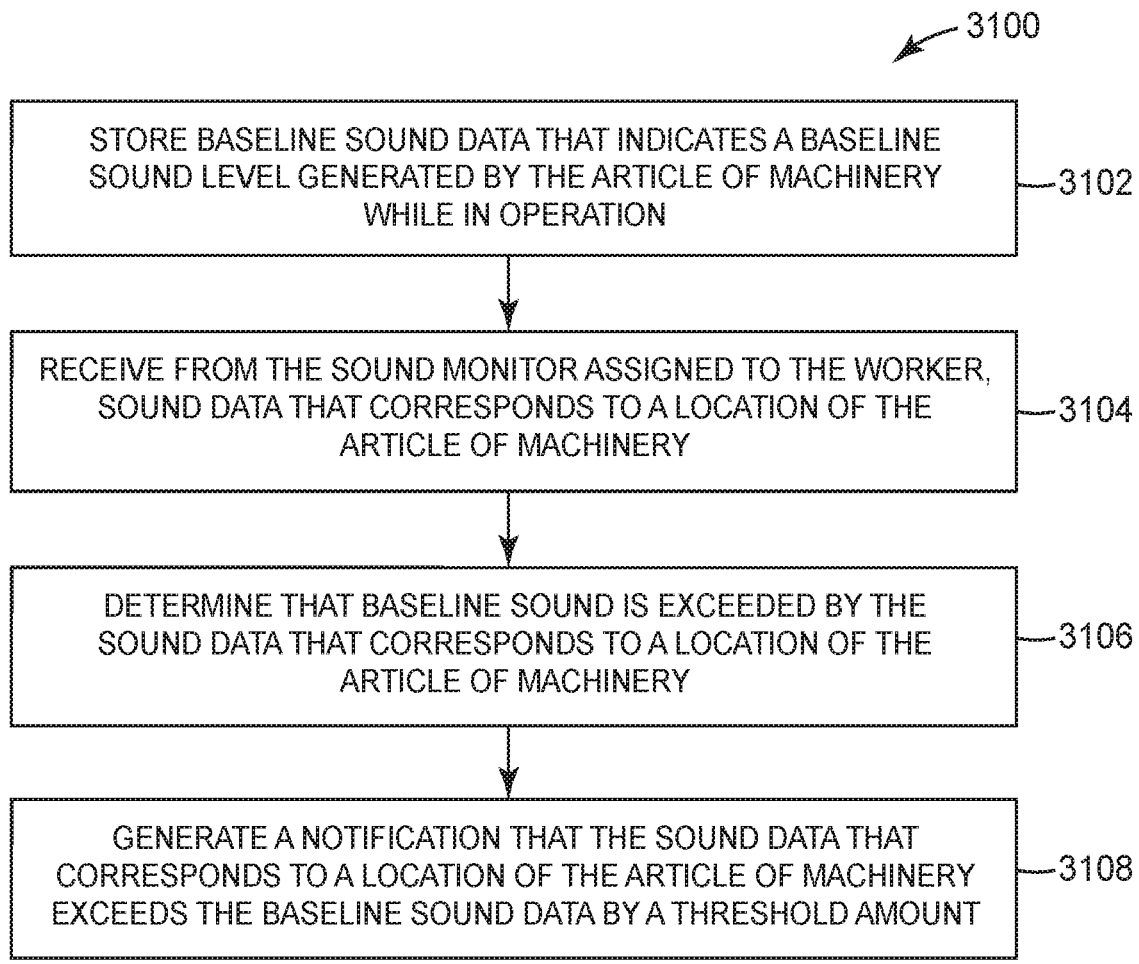
FIG. 31 illustrates a flow diagram including example operations of a computing device, in accordance with one or more techniques of this disclosure.

FIG. 31 illustrates a flow diagram 3100 including example operations of a computing device, in accordance with one or more techniques of this disclosure. For purposes of illustration only, the example operations are described below as being performed by application 228 executing at computing device 200. Application 228 may store baseline sound data that indicates a baseline sound level generated by the article of machinery while in operation (3102). In some examples, application 228 may receive from the sound level monitor assigned to the worker, sound data that corresponds to a location of the article of machinery (3104). Application 228 may determine that baseline sound data is exceeded by the sound data that corresponds to a location of the article of machinery (3106). In some examples, application 228 may generate a notification that the sound data that corresponds to a location of the article of machinery exceeds the baseline sound data by a threshold amount (3108).

Figure 32:
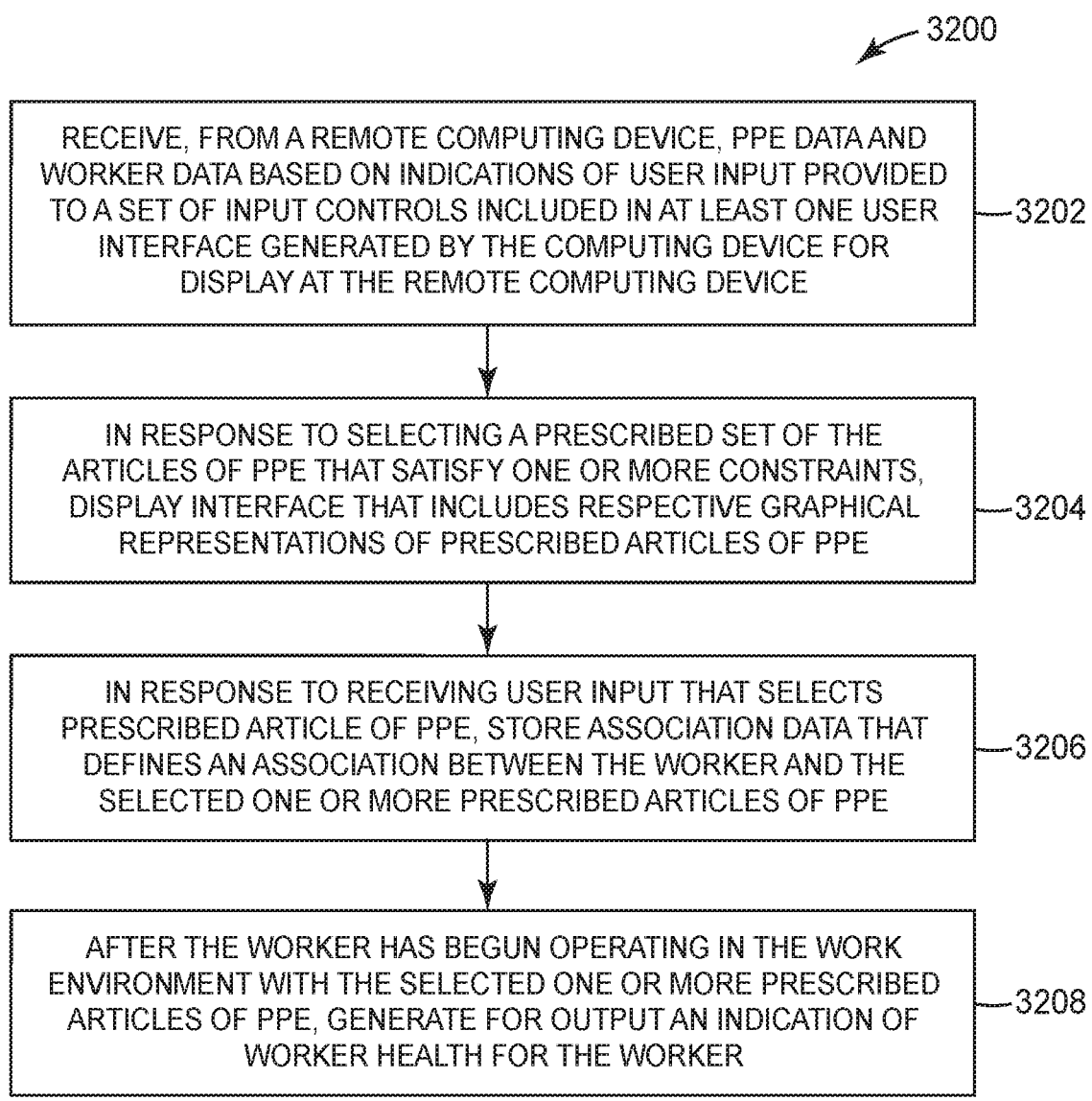
FIG. 32 illustrates a flow diagram including example operations of a computing device, in accordance with one or more techniques of this disclosure.

FIG. 32 illustrates a flow diagram 3200 including example operations of a computing device, in accordance with one or more techniques of this disclosure. For purposes of illustration only, the example operations are described below as being performed by application 228 executing at computing device 200. Application 228 may receive, from a remote computing device, PPE data and worker data based on indications of user input provided to a set of input controls included in at least one user interface generated by the computing device for display at the remote computing device, wherein the input controls receive at least: PPE data that describes each of the set of articles of PPE and worker data that describes the worker (3202). In some examples, application 228 may, in response to selecting a prescribed set of the articles of PPE that satisfy one or more constraints imposed by a work environment of the worker and the set of articles of PPE, generate for display at least one graphical user interface that includes respective graphical representations of the prescribed set of the articles of PPE (3204). Application 228 may, in response to receiving at least one indication of user input that selects one or more of the prescribed set of the articles of PPE for the worker, store, based on the PPE data and the worker data, association data that defines an association between the worker and the selected one or more prescribed articles of PPE (3206). In some examples, application 228 may, after the worker has begun operating in the work environment with the selected one or more prescribed articles of PPE, generate for output an indication of worker health for the worker that is based at least in part on each of: work environment data that describes the work environment during worker operation in the work environment and the association data between the worker and the selected one or more prescribed articles of PPE (3208).

Example 1

A method comprising: receiving, by a computing device, fit-testing data for a worker, wherein the fit-testing data comprises a value indicating a noise level attenuation for the worker for a particular form of hearing protection worn by the worker; determining, based at least in part on the fit-testing data and noise level information associated with a worksite, whether the particular form of hearing protection satisfies a threshold for the worksite; and in response to determining that the particular form of hearing protection satisfies the threshold, generating for display, a recommendation to use the particular form of hearing protection for the worksite.

Example 2

The method of Example 1, wherein determining, based at least in part on the fit-testing data and the noise level information associated with a worksite, whether the particular form of hearing protection satisfies the threshold for the worksite, further comprises: selecting noise level information associated with the worksite; comparing the noise level information associated with the worksite to noise level information specified by the value in the fit-testing data; and determining whether the noise level information associated with the worksite indicates a first noise level is less than a second noise level of the noise level information included in the fit-testing data.

Example 3

The method of any of Examples 1-2, wherein the recommendation is a first recommendation and the form of hearing protection is a first form of hearing protection, the method further comprising: in response to determining that the particular form of hearing protection does not satisfy the threshold, generating for display, a second recommendation to use a second form of hearing protection for the worksite, wherein the second form of hearing protection reduces noise levels by a greater amount than the first form of hearing protection.

Example 4

A computing device comprising: one or more computer processors; and a memory comprising instructions that when executed by the one or more computer processors cause the one or more computer processors to perform any of the method of Examples 1-3.

Example 5

A method comprising: receiving, by a computing device, first and second sets of noise level data that correspond to first and second workers; determining that, for the first and second sets of noise level data, the first and second workers are within a threshold distance of one another in a worksite; and in response to determining that a noise level difference between the first and second sets of noise level data satisfy a threshold, generating an alert.

Example 6

The method of Example 5, further comprising: in response to determining that a noise level difference between the first and second sets of noise level data satisfy a threshold, identifying at least one machine within a threshold distance of at least one of the first or second workers; and wherein the alert indicates a recommendation to perform maintenance on the machine.

Example 7

The method of any of examples 5-6, further comprising: in response to determining that a noise level difference between the first and second sets of noise level data satisfy a threshold, generating a recommendation to wear hearing protection; and wherein the alert indicates a recommendation to wear the hearing protection.

Example 8

A computing device comprising: one or more computer processors; and a memory comprising instructions that when executed by the one or more computer processors cause the one or more computer processors to perform any of the method of any of Examples 4-7.

Example 9

A method comprising: receiving, by a computing device, a set of noise level data for a worker, wherein the set of noise level data indicates multiple instances of noise levels over a time duration; determining whether the multiple instances of noise levels over the time duration exceed a noise level threshold over the time duration; and in response to determining that the multiple instances of noise levels over the time duration exceed the noise level threshold over the time duration, generating an alert.

Example 10

The method of Example 9, wherein the noise level data over the time duration is based on at least two different worksites.

Example 11

The method of any of Examples 9-10, wherein the alert includes a recommendation to wear a particular form of hearing protection that provides greater protection for the worker.

Example 12

A computing device comprising: one or more computer processors; and a memory comprising instructions that when executed by the one or more computer processors cause the one or more computer processors to perform any of the method of any of Examples 9-11.

Example 13

A method comprising: receiving, by a computing device, wear-time data that indicates one or more instances of a worker wearing personal protective equipment; correlating the wear-time data to one or more Standard Threshold Shifts (STSs); and generating, based at least in part on a correlation between the one or more STSs and the wear-time data, an alert.

Example 14

The method of Example 13, wherein the alert includes a recommendation to wear a particular form of hearing protection that provides greater protection for the worker.

Example 15

The method of any of Examples 13-14, wherein the alert is based at least in part on compliance to a hearing conservation program.

Example 16

A computing device comprising: one or more computer processors; and a memory comprising instructions that when executed by the one or more computer processors cause the one or more computer processors to perform any of the method of Examples 13-15.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media, which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor", as used may refer to any of the foregoing structure or any other structure suitable for implementation of the techniques described. In addition, in some aspects, the functionality described may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

It is to be recognized that depending on the embodiment, certain acts or events of any of the methods described herein can be performed in a different sequence, may be added, merged, or left out all together (e.g., not all described acts or events are necessary for the practice of the method). Moreover, in certain embodiments, acts or events may be performed concurrently, e.g., through multi-threaded processing, interrupt processing, or multiple processors, rather than sequentially.

In some examples, a computer-readable storage medium includes a non-transitory medium. The term "non-transitory" indicates, in some examples, that the storage medium is not embodied in a carrier wave or a propagated signal. In certain examples, a non-transitory storage medium stores data that can, over time, change (e.g., in RAM or cache).

Various examples have been described. These and other examples are within the scope of the following claims.

What is claimed is:

1. A system comprising:
   a first article of hearing protection assigned to a worker, and a portable computing device assigned to the worker; and
   a remote computing device communicatively coupled to the portable computing device, the remote computing device comprising one or more computer processors and a memory comprising instructions that when executed by the one or more computer processors cause the one or more computer processors to:
      receive first work site sound exposure data that indicates a first amount of work site sound that the worker was exposed to over a first period of time for a particular day in a first area of a work environment;
      after the worker has moved to a second area of a work environment in the particular day, receive second work site sound exposure data that indicates a second amount of work site sound that the worker has been exposed to over a second period of time for the particular day in the second area of the work environment;
      in response to determining that the worker has moved to the second area of the work environment in the particular day, determine that a work site sound level in the second area is greater than a work site sound level in the first area;
      identify, based at least in part on the determination that the work site sound level in the second area is greater than the work site sound level in the first area, a second article of hearing protection that attenuates sound more than the first article of hearing protection; and
      generate for output an indication of the second article of hearing protection;
      determine, based on the first and second work site sound exposure data in the first area of the work environment and in the second area of a work environment and based at least in part on an amount of sound attenuation provided by the article of hearing protection assigned to the worker, that a cumulative amount of work site sound that the worker has been exposed to over the first and second periods of time in the first area of the work environment and in the second area of a work environment exceeds a threshold for the particular day; and
      generate a notification for the portable computing device based on the cumulative amount of work site sound that the worker has been exposed to over the first and second periods of time in the first area of the work environment and in the second area of a work environment exceeding a threshold for the particular day.

2. The system of claim 1, wherein the threshold for the particular day is less than a maximum amount of allowable sound exposure for the particular day.

3. The system of claim 1, wherein the remote computing device receives at least the first or second sound exposure data from one or more portable sound level monitors worn by one or more workers in the work environment.

4. The system of claim 1, wherein a first work site sound level in the first area is different than a second work site sound level in the second area.

5. The system of claim 1, wherein the particular day is a defined time duration stored in the computing device, and wherein a cumulative amount of time based on the first and second periods of time is greater than the defined time duration.

6. The system of claim 1, wherein the remote computing device further stores data that defines associations between different respective workers and different types of personal protective equipment (PPE) assigned to the respective workers, and wherein the different types of PPE include one or more of fall protection PPE, respiratory PPE, head-eye-face PPE, welding PPE, or hearing protection PPE.

7. The system of claim 1, wherein to generate the notification for the portable computing device based on the cumulative amount of sound that the worker has been exposed to over the first and second periods of time the memory comprises instructions that when executed by the one or more computer processors cause the one or more computer processors to:
   generate a risk score based at least in part on the worker's usage of at least one article of PPE in the work environment.

8. A computing device comprising:
   one or more computer processors; and
   a memory comprising instructions that when executed by the one or more computer processors cause the one or more computer processors to:
   receive, by a remote computing device, first work site sound exposure data that indicates a first amount of work site sound that a worker was exposed to over a first period of time for a particular day in a first area of a work environment, wherein a first article of hearing protection is assigned to the worker, and a portable computing device is assigned to the worker;
   after the worker has moved to a second area of a work environment in the particular day, receive second work site sound exposure data that indicates a second amount of work site sound that the worker has been exposed to over a second period of time for the particular day in the second area of the work environment;
   in response to determining that the worker has moved to the second area of the work environment in the particular day, determine that a work site sound level in the second area is greater than a work site sound level in the first area;
   identify, based at least in part on the determination that the work site sound level in the second area is greater than the work site sound level in the first area, a second article of hearing protection that attenuates sound more than the first article of hearing protection; and generate for output an indication of the second article of hearing protection;

determine, based on the first and second work site sound exposure data in the first area of the work environment and in the second area of a work environment and based at least in part on an amount of sound attenuation provided by the article of hearing protection assigned to the worker, that a cumulative amount of work site sound that the worker has been exposed to over the first and second periods of time in the first area of the work environment and in the second area of a work environment exceeds a threshold for the particular day; and generate, a notification for the portable computing device based on the cumulative amount of work site sound that the worker has been exposed to over the first and second periods of time in the first area of the work environment and in the second area of a work environment exceeding a threshold for the particular day.

9. The computing device of claim 8, wherein the threshold for the particular day is less than a maximum amount of allowable sound exposure for the particular day.

10. The computing device of claim 8, wherein to receive the first or second work site sound exposure data the memory comprises instructions that when executed cause the one or more processors to receive at least the first or second sound exposure data from one or more portable sound level monitors worn by one or more workers in the work environment.

11. The computing device of claim 8, wherein a first sound level in the first area is different than a second sound level in the second area.

12. The computing device of claim 8, wherein the particular day is a defined time duration stored in the computing device, and wherein a cumulative amount of time based on the first and second periods of time is greater than the defined time duration.

13. The computing device of claim 8, wherein the remote computing device further stores data that defines associations between different respective workers and different types of personal protective equipment (PPE) assigned to the respective workers, and wherein the different types of PPE include one or more of fall protection PPE, respiratory PPE, head-eye-face PPE, welding PPE, or hearing protection PPE.

14. A non-transitory computer-readable storage medium encoded with instructions that, when executed, cause at least one processor of a computing device to: receive first work site sound exposure data that indicates a first amount of work site sound that a worker was exposed to over a first period of time for a particular day in a first area of a work environment;

after the worker has moved to a second area of a work environment in the particular day, receive second work site sound exposure data that indicates a second amount of work site sound that the worker has been exposed to over a second period of time for the particular day in the second area of the work environment;

determine, based on the first and second sound work site exposure data in the first area of the work environment and in the second area of a work environment and based at least in part on an amount of sound attenuation provided by the article of hearing protection assigned to the worker, that a cumulative amount of work site sound that the worker has been exposed to over the first and second periods of time in the first area of the work environment and in the second area of a work environment exceeds a threshold for the particular day; and generate a notification for the portable computing device based on the cumulative amount of work site sound that the worker has been exposed to over the first and second periods of time in the first area of the work environment and in the second area of a work environment exceeding a threshold for the particular day.

* * * * *